US012698494B2

(12) United States Patent
Voorberg et al.

(10) Patent No.: US 12,698,494 B2
(45) Date of Patent: Aug. 4, 2026

(54) ADAMTS13 PROTEIN VARIANTS AND USES THEREOF

(71) Applicant: Sanquin IP B.V., Amsterdam (NL)

(72) Inventors: Johannes Jacobus Voorberg, Wormer (NL); Nuno Alexandre Gomes Graça, Amsterdam (NL); Boğaç Erçiğ, Amsterdam (NL)

(73) Assignee: SANQUIN IP B.V., Amsterdam (NL)

( * ) Notice: Subject to any disclaimer, the term of this patent is extended or adjusted under 35 U.S.C. 154(b) by 630 days.

(21) Appl. No.: 17/927,474

(22) PCT Filed: May 25, 2021

(86) PCT No.: PCT/NL2021/050325
§ 371 (c)(1),
(2) Date: Nov. 23, 2022

(87) PCT Pub. No.: WO2021/242092
PCT Pub. Date: Dec. 2, 2021

(65) Prior Publication Data
US 2023/0242896 A1 Aug. 3, 2023

(30) Foreign Application Priority Data
May 25, 2020 (EP) ..................................... 20176333

(51) Int. Cl.
*C12N 9/64* (2006.01)
*A61P 7/02* (2006.01)

(52) U.S. Cl.
CPC .............. *C12N 9/6489* (2013.01); *A61P 7/02* (2018.01); *C12Y 304/24087* (2013.01)

(58) Field of Classification Search
CPC . C12N 9/6489; A61P 7/02; C12Y 304/24087; A61K 38/00
See application file for complete search history.

(56) References Cited

U.S. PATENT DOCUMENTS

| | | | |
|---|---|---|---|
| 10,413,600 B2 | 9/2019 | Kopic et al. | |
| 11,567,080 B2 | 1/2023 | Hata et al. | |

FOREIGN PATENT DOCUMENTS

| | | | |
|---|---|---|---|
| JP | 2019142850 A | 8/2019 | |
| WO | 03016492 A2 | 2/2003 | |
| WO | 2013096793 A1 | 6/2013 | |
| WO | 2017119498 A1 | 7/2017 | |

OTHER PUBLICATIONS

Singh RK et al. Protein Engineering Approaches in the Post-Genomic Era. 2017. Current Protein and Peptide Science. 18, 1-11. (Year: 2017).*
Zhang M et al. Propagated Perturbations from a Peripheral Mutation Show Interactions Showing WW Domain Thermostability. 2018 . Structure. 26, 1474-1485. (Year: 2018).*
Ercig Bogac et al., "N-glycan-mediated shielding of ADAMTS13 prevents binding of pathogenic autoantibodies in immune-mediated TTP", 2021, Thrombosis and Haemostasis, pp. 2694-2698, vol. 137, No. 19.
Nuno A.G. Graca et al., "Modifying ADAMTS13 to modulate binding of pathogenic autoantibodies of patients with acquired thrombotic thrombocytopeniaurpura", 2020, Haematologica , pp. 2619-2630, vol. 105(11).
Ercig Bogac et al., "Insights into 3D Structure of ADAMTS13: A stepping Stone towards Novel Therapeutic Treatment of Thrombotic Thrombocytopenic Purpura" 2018, Thrombosis and Haemostasis, pp. 28-41, vol. 118.
Wenhua Zhou et al., "N-Glycans of ADAMTS13 modulate its secretion and von Willebrand factor cleaving activity", Jan. 22, 2009, Blood, The American Society of Hematology, US—ISSN 0006-4971, pp. 929-935, vol. 113, Nr:4.
Eric M Ostertag et al., "ADAMTS13 autoantibodies cloned from patients with acquired thrombotic thrombocytopeni purpura: 2. Pathogenicity in an animal model", Jul. 2016, Transfusion, American Association of Blood Banks, Bethesda, MD, US—ISSN 0041-1132, Nr:7, pp. 1775-1785, vol. 56.
Brenda Luken et al, "The Spacer Domain of ADAMTS13 Contains a Major Binding Site for Antibodies in Patients with Thrombotic Thrombocytopenic Purpura", Thrombosis and Haemostasis, Jan. 7, 2005, DE—ISSN 0340-6245, vol. 93, pp. 267-274.
Cui Jian et al., "Gain-of-function ADAMTS13 variants that are resistant to autoantibodies against ADAMTS13 in patients with acquired thrombotic thrombocytopenic purpura", Blood, No. 16, Apr. 19, 2012, pp. 3836-3843, vol. 119.
International Search Report for corresponding International Application No. PCT/NL2021/050325, dated Sep. 24, 2021.

* cited by examiner

*Primary Examiner* — Paul J Holland
(74) *Attorney, Agent, or Firm* — Leason Ellis LLP

(57) ABSTRACT

The invention relates to ADAMTS13 protein variants comprising residues 1 to 685 of ADAMTS13 and wherein one or more N-linked glycosylation sites are added as compared to wild-type ADAMTS13 and/or one or more existing N-linked glycosylation sites are shifted as compared to wild-type ADAMTS13. The invention further relates to compositions comprising such ADAMTS13 variants, methods for their preparation and uses thereof, in particular as an antithrombotic agent, and in the treatment of thrombotic disease, thrombotic microangiopathy, thrombotic thrombocytopeniaurpura (TTP), hemolytic-uremic syndrome (HUS), ischemic stroke, systemic thrombosis, COVID19, antiphospholipid syndrome, pre-eclampsia/HELLP syndrome, sepsis and sickle cell disease.

20 Claims, 15 Drawing Sheets

Specification includes a Sequence Listing.

```
   1   mhqrhprarc pplcvagila cgfllgcwgp shfqqsclqa lepqavssyl spgaplkgrp
  61   pspgfqrqrq rqrraaggil hlellvavgp dvfqahqedt eryvltnlni gaellrdpsl
 121   gaqfrvhlvk mviltepega pnitanltss llsvcgwsqt inpeddtdpg hadlvlyitr
 181   fdlelpdgnr qvrgvtqlgg acsptwscli tedtgfdlgv tiaheighsf glehdgapgs
 241   gcgpsghvma sdgaapragl awspcsrrql lsllsagrar cvwdpprpqp gsaghppdaq
 301   pglyysaneq crvafgpkav actfarehld mcqalschtd pldqsscsrl lvplldgtec
 361   gvekwcskgr crslveltpi aavhgrwssw gprspcsrsc gggvvtrrrq cnnprpafgg
 421   racvgadlqa emcntqacek tqlefmsqqc artdgqplrs spggasfyhw gaavphsqgd
 481   alcrhmcrai gesfimkrgd sfldgtrcmp sgpredgtls lcvsgscrtf gcdgrmdsqq
 541   vwdrcqvcgg dnstcsprkg sftagrarey vtfltvtpnl tsvyianhrp lfthlavrig
 601   gryvvagkms ispnttypsl ledgrveyrv altedrlprl eeiriwgplq edadiqvyrr
 661   ygeeygnltr pditftyfqp kprqawvwaa vrgpcsvscg aglrwvnysc ldqarkelve
 721   tvqcqgsqqp pawpeacvle pcppywavgd fgpcsascgg glrerpvrcv eaqgsllktl
 781   pparcragaq qpavaletcn pqpcparwev sepssctsag gaglalenet cvpgadglea
 841   pvtegpgsvd eklpapepcv gmscppgwgh ldatsageka pspwgsirtg aqaahvwtpa
 901   agscsvscgr glmelrflcm dsalrpvqe elcglaskpg srrevcqavp cparwqykla
 961   acsvscgrgv vrrilycara hgeddgeeil ldtqcqglpr pepqeacsle pcpprwkvms
1021   lgpcsascgl gtarrsvacv qldqgqdvev deaacaalvr peasvpclia dctyrwhvgt
1081   wmecsvscgd giqrrrdtcl gpqaqapvpa dfcqhlpkpv tvrgcwagpc vgqgtpslvp
1141   heeaaapgrt tatpagasle wsqargllfs papqprrllp gpqensvqss acgrqhlept
1201   gtidmrgpgq adcavaigrp lgevvtlrvl esslncsagd mlllwgrltw rkmcrklldm
1261   tfssktntlv vrqrcgrpgg gvllrygsql apetfyrecd mqlfgpwgei vspslspats
1321   naggcrlfin vaphariaih alatnmgagt eganasyili rdthslrtta fhgqqvlywe
1381   sessqaemef segflkaqas lrgqywtlqs wvpemqdpqs wkgkegt
```

Relative Activity of NGLY mutants (vs WT) FRETS, pH = 6.0 (n = 1)

| Original Epitope | New Epitope | Variant |
|---|---|---|
| $_{568}REY_{570}$ | $_{568}NET_{570}$ | NGLY1 |
| $_{591}LFT_{593}$ | $_{591}NFT_{593}$ | NGLY2 |
| $_{608}KMSI_{611}$ | $_{608}NMSI_{611}$ | NGLY3 |
| $_{608}KMSI_{611}$ | $_{608}KNST_{611}$ | NGLY4 |
| $_{636}RLPR_{639}$ | $_{636}NLSR_{639}$ | NGLY5 |
| $_{636}RLPR_{639}$ | $_{636}RNAS_{639}$ | NGLY6 |

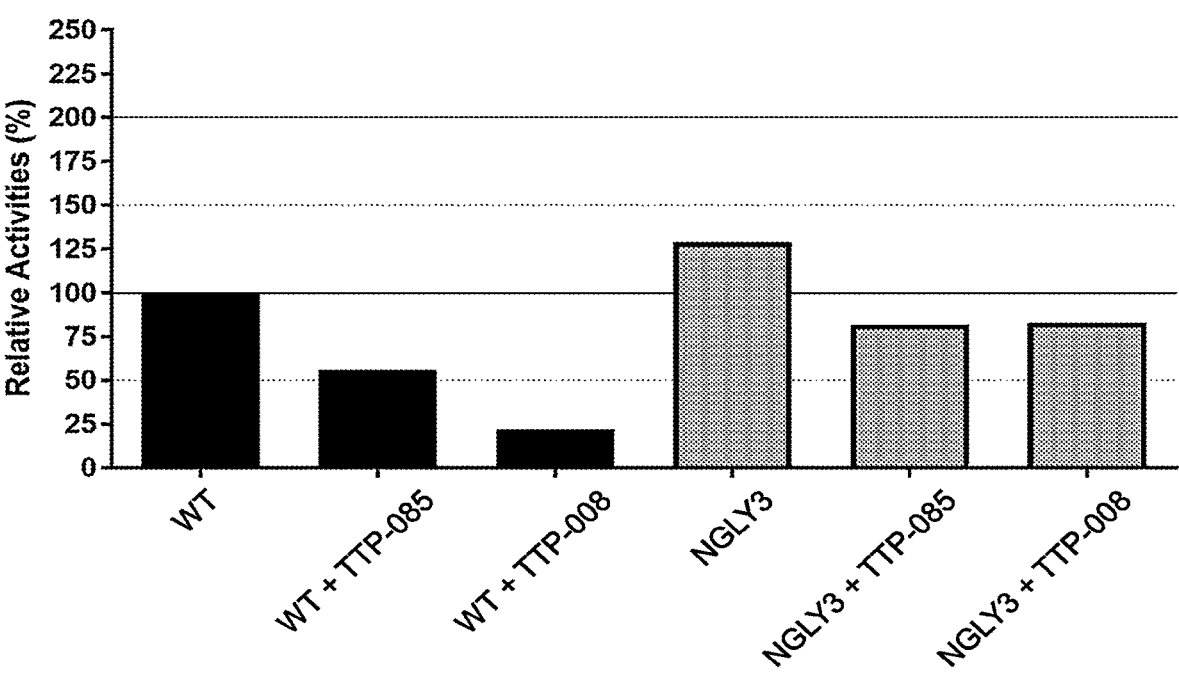
ADAMTS13 Variants and patient sample
Fig. 7
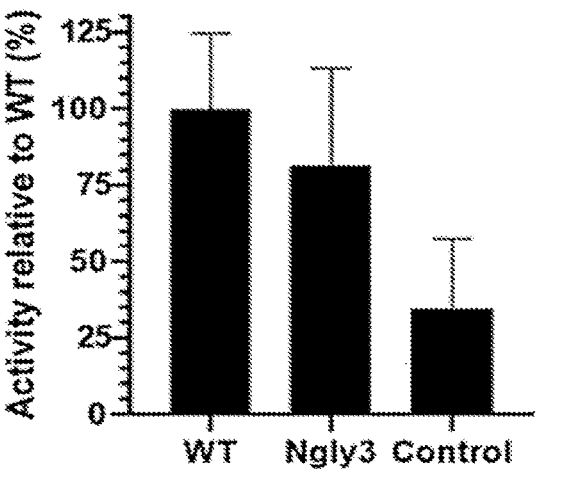 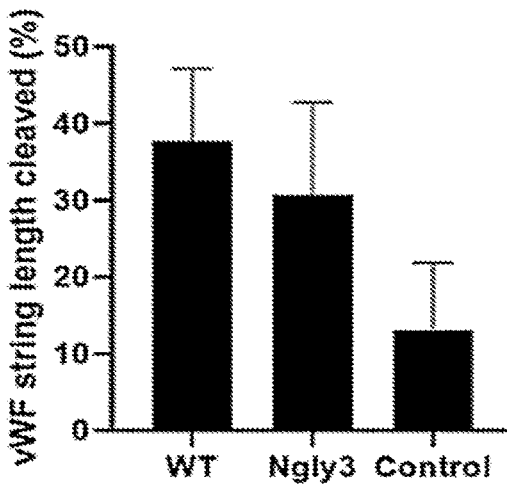
Fig. 8

SEQUENCE LISTING

<160> NUMBER OF SEQ ID NOS: 122

<210> SEQ ID NO 1
<211> LENGTH: 1427
<212> TYPE: PRT
<213> ORGANISM: Homo sapiens

<400> SEQUENCE: 1

```
Met His Gln Arg His Pro Arg Ala Arg Cys Pro Pro Leu Cys Val Ala
1               5                   10                  15

Gly Ile Leu Ala Cys Gly Phe Leu Leu Gly Cys Trp Gly Pro Ser His
                20                  25                  30

Phe Gln Gln Ser Cys Leu Gln Ala Leu Glu Pro Gln Ala Val Ser Ser
            35                  40                  45

Tyr Leu Ser Pro Gly Ala Pro Leu Lys Gly Arg Pro Pro Ser Pro Gly
        50                  55                  60

Phe Gln Arg Gln Arg Gln Arg Arg Ala Ala Gly Gly Ile Leu
65                  70                  75                  80

His Leu Glu Leu Leu Val Ala Val Gly Pro Asp Val Phe Gln Ala His
                85                  90                  95

Gln Glu Asp Thr Glu Arg Tyr Val Leu Thr Asn Leu Asn Ile Gly Ala
            100                 105                 110

Glu Leu Leu Arg Asp Pro Ser Leu Gly Ala Gln Phe Arg Val His Leu
        115                 120                 125

Val Lys Met Val Ile Leu Thr Glu Pro Glu Gly Ala Pro Asn Ile Thr
    130                 135                 140

Ala Asn Leu Thr Ser Ser Leu Leu Ser Val Cys Gly Trp Ser Gln Thr
145                 150                 155                 160

Ile Asn Pro Glu Asp Asp Thr Asp Pro Gly His Ala Asp Leu Val Leu
                165                 170                 175

Tyr Ile Thr Arg Phe Asp Leu Glu Leu Pro Asp Gly Asn Arg Gln Val
                180                 185                 190

Arg Gly Val Thr Gln Leu Gly Gly Ala Cys Ser Pro Thr Trp Ser Cys
            195                 200                 205

Leu Ile Thr Glu Asp Thr Gly Phe Asp Leu Gly Val Thr Ile Ala His
    210                 215                 220

Glu Ile Gly His Ser Phe Gly Leu Glu His Asp Gly Ala Pro Gly Ser
225                 230                 235                 240

Gly Cys Gly Pro Ser Gly His Val Met Ala Ser Asp Gly Ala Ala Pro
                245                 250                 255

Arg Ala Gly Leu Ala Trp Ser Pro Cys Ser Arg Arg Gln Leu Leu Ser
            260                 265                 270

Leu Leu Ser Ala Gly Arg Ala Arg Cys Val Trp Asp Pro Pro Arg Pro
        275                 280                 285

Gln Pro Gly Ser Ala Gly His Pro Pro Asp Ala Gln Pro Gly Leu Tyr
    290                 295                 300

Tyr Ser Ala Asn Glu Gln Cys Arg Val Ala Phe Gly Pro Lys Ala Val
305                 310                 315                 320

Ala Cys Thr Phe Ala Arg Glu His Leu Asp Met Cys Gln Ala Leu Ser
                325                 330                 335

Cys His Thr Asp Pro Leu Asp Gln Ser Ser Cys Ser Arg Leu Leu Val
                340                 345                 350

Pro Leu Leu Asp Gly Thr Glu Cys Gly Val Glu Lys Trp Cys Ser Lys
        355                 360                 365
```

```
Gly Arg Cys Arg Ser Leu Val Glu Leu Thr Pro Ile Ala Ala Val His
    370             375             380

Gly Arg Trp Ser Ser Trp Gly Pro Arg Ser Pro Cys Ser Arg Ser Cys
385             390             395             400

Gly Gly Gly Val Val Thr Arg Arg Gln Cys Asn Asn Pro Arg Pro
                405             410             415

Ala Phe Gly Gly Arg Ala Cys Val Gly Ala Asp Leu Gln Ala Glu Met
            420             425             430

Cys Asn Thr Gln Ala Cys Glu Lys Thr Gln Leu Glu Phe Met Ser Gln
        435             440             445

Gln Cys Ala Arg Thr Asp Gly Gln Pro Leu Arg Ser Ser Pro Gly Gly
        450             455             460

Ala Ser Phe Tyr His Trp Gly Ala Ala Val Pro His Ser Gln Gly Asp
465             470             475             480

Ala Leu Cys Arg His Met Cys Arg Ala Ile Gly Glu Ser Phe Ile Met
                485             490             495

Lys Arg Gly Asp Ser Phe Leu Asp Gly Thr Arg Cys Met Pro Ser Gly
            500             505             510

Pro Arg Glu Asp Gly Thr Leu Ser Leu Cys Val Ser Gly Ser Cys Arg
            515             520             525

Thr Phe Gly Cys Asp Gly Arg Met Asp Ser Gln Gln Val Trp Asp Arg
        530             535             540

Cys Gln Val Cys Gly Gly Asp Asn Ser Thr Cys Ser Pro Arg Lys Gly
545             550             555             560

Ser Phe Thr Ala Gly Arg Ala Arg Glu Tyr Val Thr Phe Leu Thr Val
            565             570             575

Thr Pro Asn Leu Thr Ser Val Tyr Ile Ala Asn His Arg Pro Leu Phe
            580             585             590

Thr His Leu Ala Val Arg Ile Gly Gly Arg Tyr Val Val Ala Gly Lys
        595             600             605

Met Ser Ile Ser Pro Asn Thr Thr Tyr Pro Ser Leu Leu Glu Asp Gly
    610             615             620

Arg Val Glu Tyr Arg Val Ala Leu Thr Glu Asp Arg Leu Pro Arg Leu
625             630             635             640

Glu Glu Ile Arg Ile Trp Gly Pro Leu Gln Glu Asp Ala Asp Ile Gln
            645             650             655

Val Tyr Arg Arg Tyr Gly Glu Glu Tyr Gly Asn Leu Thr Arg Pro Asp
            660             665             670

Ile Thr Phe Thr Tyr Phe Gln Pro Lys Pro Arg Gln Ala Trp Val Trp
        675             680             685

Ala Ala Val Arg Gly Pro Cys Ser Val Ser Cys Gly Ala Gly Leu Arg
        690             695             700

Trp Val Asn Tyr Ser Cys Leu Asp Gln Ala Arg Lys Glu Leu Val Glu
705             710             715             720

Thr Val Gln Cys Gln Gly Ser Gln Gln Pro Pro Ala Trp Pro Glu Ala
            725             730             735

Cys Val Leu Glu Pro Cys Pro Pro Tyr Trp Ala Val Gly Asp Phe Gly
            740             745             750

Pro Cys Ser Ala Ser Cys Gly Gly Gly Leu Arg Glu Arg Pro Val Arg
            755             760             765

Cys Val Glu Ala Gln Gly Ser Leu Leu Lys Thr Leu Pro Pro Ala Arg
            770             775             780

Cys Arg Ala Gly Ala Gln Gln Pro Ala Val Ala Leu Glu Thr Cys Asn
```

-continued

```
785                790                795                800

Pro Gln Pro Cys Pro Ala Arg Trp Glu Val Ser Glu Pro Ser Ser Cys
              805                810                815

Thr Ser Ala Gly Gly Ala Gly Leu Ala Leu Glu Asn Glu Thr Cys Val
              820                825                830

Pro Gly Ala Asp Gly Leu Glu Ala Pro Val Thr Glu Gly Pro Gly Ser
              835                840                845

Val Asp Glu Lys Leu Pro Ala Pro Glu Pro Cys Val Gly Met Ser Cys
      850                855                860

Pro Pro Gly Trp Gly His Leu Asp Ala Thr Ser Ala Gly Glu Lys Ala
865                870                875                880

Pro Ser Pro Trp Gly Ser Ile Arg Thr Gly Ala Gln Ala Ala His Val
              885                890                895

Trp Thr Pro Ala Ala Gly Ser Cys Ser Val Ser Cys Gly Arg Gly Leu
              900                905                910

Met Glu Leu Arg Phe Leu Cys Met Asp Ser Ala Leu Arg Val Pro Val
              915                920                925

Gln Glu Glu Leu Cys Gly Leu Ala Ser Lys Pro Gly Ser Arg Arg Glu
      930                935                940

Val Cys Gln Ala Val Pro Cys Pro Ala Arg Trp Gln Tyr Lys Leu Ala
945                950                955                960

Ala Cys Ser Val Ser Cys Gly Arg Gly Val Val Arg Arg Ile Leu Tyr
              965                970                975

Cys Ala Arg Ala His Gly Glu Asp Asp Gly Glu Glu Ile Leu Leu Asp
              980                985                990

Thr Gln Cys Gln Gly Leu Pro Arg  Pro Glu Pro Gln Glu  Ala Cys Ser
          995                1000                1005

Leu Glu  Pro Cys Pro Pro Arg  Trp Lys Val Met Ser  Leu Gly Pro
    1010                1015                1020

Cys Ser  Ala Ser Cys Gly Leu  Gly Thr Ala Arg Arg  Ser Val Ala
    1025                1030                1035

Cys Val  Gln Leu Asp Gln Gly  Gln Asp Val Glu Val  Asp Glu Ala
    1040                1045                1050

Ala Cys  Ala Ala Leu Val Arg  Pro Glu Ala Ser Val  Pro Cys Leu
    1055                1060                1065

Ile Ala  Asp Cys Thr Tyr Arg  Trp His Val Gly Thr  Trp Met Glu
    1070                1075                1080

Cys Ser  Val Ser Cys Gly Asp  Gly Ile Gln Arg Arg  Arg Asp Thr
    1085                1090                1095

Cys Leu  Gly Pro Gln Ala Gln  Ala Pro Val Pro Ala  Asp Phe Cys
    1100                1105                1110

Gln His  Leu Pro Lys Pro Val  Thr Val Arg Gly Cys  Trp Ala Gly
    1115                1120                1125

Pro Cys  Val Gly Gln Gly Thr  Pro Ser Leu Val Pro  His Glu Glu
    1130                1135                1140

Ala Ala  Ala Pro Gly Arg Thr  Thr Ala Thr Pro Ala  Gly Ala Ser
    1145                1150                1155

Leu Glu  Trp Ser Gln Ala Arg  Gly Leu Leu Phe Ser  Pro Ala Pro
    1160                1165                1170

Gln Pro  Arg Arg Leu Leu Pro  Gly Pro Gln Glu Asn  Ser Val Gln
    1175                1180                1185

Ser Ser  Ala Cys Gly Arg Gln  His Leu Glu Pro Thr  Gly Thr Ile
    1190                1195                1200
```

-continued

```
Asp Met Arg Gly Pro Gly Gln  Ala Asp Cys Ala Val  Ala Ile Gly
    1205              1210              1215

Arg Pro Leu Gly Glu Val Val  Thr Leu Arg Val Leu  Glu Ser Ser
    1220              1225              1230

Leu Asn Cys Ser Ala Gly Asp  Met Leu Leu Leu Trp  Gly Arg Leu
    1235              1240              1245

Thr Trp Arg Lys Met Cys Arg  Lys Leu Leu Asp Met  Thr Phe Ser
    1250              1255              1260

Ser Lys Thr Asn Thr Leu Val  Val Arg Gln Arg Cys  Gly Arg Pro
    1265              1270              1275

Gly Gly Gly Val Leu Leu Arg  Tyr Gly Ser Gln Leu  Ala Pro Glu
    1280              1285              1290

Thr Phe Tyr Arg Glu Cys Asp  Met Gln Leu Phe Gly  Pro Trp Gly
    1295              1300              1305

Glu Ile Val Ser Pro Ser Leu  Ser Pro Ala Thr Ser  Asn Ala Gly
    1310              1315              1320

Gly Cys Arg Leu Phe Ile Asn  Val Ala Pro His Ala  Arg Ile Ala
    1325              1330              1335

Ile His Ala Leu Ala Thr Asn  Met Gly Ala Gly Thr  Glu Gly Ala
    1340              1345              1350

Asn Ala Ser Tyr Ile Leu Ile  Arg Asp Thr His Ser  Leu Arg Thr
    1355              1360              1365

Thr Ala Phe His Gly Gln Gln  Val Leu Tyr Trp Glu  Ser Glu Ser
    1370              1375              1380

Ser Gln Ala Glu Met Glu Phe  Ser Glu Gly Phe Leu  Lys Ala Gln
    1385              1390              1395

Ala Ser Leu Arg Gly Gln Tyr  Trp Thr Leu Gln Ser  Trp Val Pro
    1400              1405              1410

Glu Met Gln Asp Pro Gln Ser  Trp Lys Gly Lys Glu  Gly Thr
    1415              1420              1425
```

```
<210> SEQ ID NO 2
<211> LENGTH: 4
<212> TYPE: PRT
<213> ORGANISM: Homo sapiens

<400> SEQUENCE: 2

Lys Met Ser Ile
1

<210> SEQ ID NO 3
<211> LENGTH: 4
<212> TYPE: PRT
<213> ORGANISM: Artificial Sequence
<220> FEATURE:
<223> OTHER INFORMATION: ADAMTS13 variant NGLY3

<400> SEQUENCE: 3

Asn Met Ser Ile
1

<210> SEQ ID NO 4
<211> LENGTH: 4
<212> TYPE: PRT
<213> ORGANISM: Artificial Sequence
<220> FEATURE:
<223> OTHER INFORMATION: ADAMTS13 variant NGLY4

<400> SEQUENCE: 4
```

-continued

```
Lys Asn Ser Thr
1

<210> SEQ ID NO 5
<211> LENGTH: 4
<212> TYPE: PRT
<213> ORGANISM: Homo sapiens

<400> SEQUENCE: 5

Arg Leu Pro Arg
1

<210> SEQ ID NO 6
<211> LENGTH: 4
<212> TYPE: PRT
<213> ORGANISM: Artificial Sequence
<220> FEATURE:
<223> OTHER INFORMATION: ADAMTS13 variant NGLY5

<400> SEQUENCE: 6

Asn Leu Ser Arg
1

<210> SEQ ID NO 7
<211> LENGTH: 4
<212> TYPE: PRT
<213> ORGANISM: Artificial Sequence
<220> FEATURE:
<223> OTHER INFORMATION: ADAMTS13 variant NGLY6

<400> SEQUENCE: 7

Arg Asn Ala Ser
1

<210> SEQ ID NO 8
<211> LENGTH: 10
<212> TYPE: PRT
<213> ORGANISM: Homo sapiens

<400> SEQUENCE: 8

Ile Gly Gly Arg Tyr Val Val Ala Gly Lys
1               5                   10

<210> SEQ ID NO 9
<211> LENGTH: 21
<212> TYPE: PRT
<213> ORGANISM: Homo sapiens

<400> SEQUENCE: 9

Met Ser Ile Ser Pro Asn Thr Thr Tyr Pro Ser Leu Leu Glu Asp Gly
1               5                   10                  15

Arg Val Glu Tyr Arg
            20

<210> SEQ ID NO 10
<211> LENGTH: 31
<212> TYPE: PRT
<213> ORGANISM: Homo sapiens

<400> SEQUENCE: 10

Ile Gly Gly Arg Tyr Val Val Ala Gly Lys Met Ser Ile Ser Pro Asn
1               5                   10                  15

Thr Thr Tyr Pro Ser Leu Leu Glu Asp Gly Arg Val Glu Tyr Arg
            20                  25                  30
```

```
<210> SEQ ID NO 11
<211> LENGTH: 27
<212> TYPE: PRT
<213> ORGANISM: Artificial Sequence
<220> FEATURE:
<223> OTHER INFORMATION: peptide 3 NGLY3

<400> SEQUENCE: 11

Tyr Val Val Ala Gly Asn Met Ser Ile Ser Pro Asn Thr Thr Tyr Pro
1               5                   10                  15

Ser Leu Leu Glu Asp Gly Arg Val Glu Tyr Arg
            20                  25

<210> SEQ ID NO 12
<211> LENGTH: 31
<212> TYPE: PRT
<213> ORGANISM: Artificial Sequence
<220> FEATURE:
<223> OTHER INFORMATION: NGLY3 599-629

<400> SEQUENCE: 12

Ile Gly Gly Arg Tyr Val Val Ala Gly Asn Met Ser Ile Ser Pro Asn
1               5                   10                  15

Thr Thr Tyr Pro Ser Leu Leu Glu Asp Gly Arg Val Glu Tyr Arg
            20                  25                  30

<210> SEQ ID NO 13
<211> LENGTH: 27
<212> TYPE: PRT
<213> ORGANISM: Artificial Sequence
<220> FEATURE:
<223> OTHER INFORMATION: K608A peptide 3

<400> SEQUENCE: 13

Tyr Val Val Ala Gly Ala Met Ser Ile Ser Pro Asn Thr Thr Tyr Pro
1               5                   10                  15

Ser Leu Leu Glu Asp Gly Arg Val Glu Tyr Arg
            20                  25

<210> SEQ ID NO 14
<211> LENGTH: 31
<212> TYPE: PRT
<213> ORGANISM: Artificial Sequence
<220> FEATURE:
<223> OTHER INFORMATION: K608A aa599-629

<400> SEQUENCE: 14

Ile Gly Gly Arg Tyr Val Val Ala Gly Ala Met Ser Ile Ser Pro Asn
1               5                   10                  15

Thr Thr Tyr Pro Ser Leu Leu Glu Asp Gly Arg Val Glu Tyr Arg
            20                  25                  30

<210> SEQ ID NO 15
<211> LENGTH: 5
<212> TYPE: PRT
<213> ORGANISM: Homo sapiens

<400> SEQUENCE: 15

Arg Phe Arg Tyr Tyr
1               5

<210> SEQ ID NO 16
<211> LENGTH: 5
```

```
<212> TYPE: PRT
<213> ORGANISM: Artificial Sequence
<220> FEATURE:
<223> OTHER INFORMATION: gain of function variant

<400> SEQUENCE: 16

Lys Tyr Lys Phe Phe
1               5

<210> SEQ ID NO 17
<211> LENGTH: 5
<212> TYPE: PRT
<213> ORGANISM: Homo sapiens

<400> SEQUENCE: 17

Ala Arg Glu Tyr Val
1               5

<210> SEQ ID NO 18
<211> LENGTH: 5
<212> TYPE: PRT
<213> ORGANISM: Artificial Sequence
<220> FEATURE:
<223> OTHER INFORMATION: NGLY1

<400> SEQUENCE: 18

Ala Asn Glu Thr Val
1               5

<210> SEQ ID NO 19
<211> LENGTH: 5
<212> TYPE: PRT
<213> ORGANISM: Homo sapiens

<400> SEQUENCE: 19

Pro Leu Phe Thr His
1               5

<210> SEQ ID NO 20
<211> LENGTH: 5
<212> TYPE: PRT
<213> ORGANISM: Artificial Sequence
<220> FEATURE:
<223> OTHER INFORMATION: NGLY2

<400> SEQUENCE: 20

Pro Asn Phe Thr His
1               5

<210> SEQ ID NO 21
<211> LENGTH: 5
<212> TYPE: PRT
<213> ORGANISM: Homo sapiens

<400> SEQUENCE: 21

Gly Lys Met Ser Ile
1               5

<210> SEQ ID NO 22
<211> LENGTH: 5
<212> TYPE: PRT
<213> ORGANISM: Artificial Sequence
<220> FEATURE:
<223> OTHER INFORMATION: NGLY3

<400> SEQUENCE: 22
```

```
Gly Asn Met Ser Ile
1               5

<210> SEQ ID NO 23
<211> LENGTH: 5
<212> TYPE: PRT
<213> ORGANISM: Homo sapiens

<400> SEQUENCE: 23

Lys Met Ser Ile Ser
1               5

<210> SEQ ID NO 24
<211> LENGTH: 5
<212> TYPE: PRT
<213> ORGANISM: Artificial Sequence
<220> FEATURE:
<223> OTHER INFORMATION: NGLY4

<400> SEQUENCE: 24

Lys Asn Ser Thr Ser
1               5

<210> SEQ ID NO 25
<211> LENGTH: 5
<212> TYPE: PRT
<213> ORGANISM: Homo sapiens

<400> SEQUENCE: 25

Asp Arg Leu Pro Arg
1               5

<210> SEQ ID NO 26
<211> LENGTH: 5
<212> TYPE: PRT
<213> ORGANISM: Artificial Sequence
<220> FEATURE:
<223> OTHER INFORMATION: NGLY5

<400> SEQUENCE: 26

Asp Asn Leu Ser Arg
1               5

<210> SEQ ID NO 27
<211> LENGTH: 5
<212> TYPE: PRT
<213> ORGANISM: Homo sapiens

<400> SEQUENCE: 27

Arg Leu Pro Arg Leu
1               5

<210> SEQ ID NO 28
<211> LENGTH: 5
<212> TYPE: PRT
<213> ORGANISM: Artificial Sequence
<220> FEATURE:
<223> OTHER INFORMATION: NGLY6

<400> SEQUENCE: 28

Arg Asn Ala Ser Leu
1               5

<210> SEQ ID NO 29
<211> LENGTH: 6
<212> TYPE: PRT
```

<213> ORGANISM: Homo sapiens

<400> SEQUENCE: 29

Glu Tyr Gly Asn Leu Thr
1               5

<210> SEQ ID NO 30
<211> LENGTH: 6
<212> TYPE: PRT
<213> ORGANISM: Artificial Sequence
<220> FEATURE:
<223> OTHER INFORMATION: N-gly7 (glycan shift from N667 to Y665)

<400> SEQUENCE: 30

Glu Asn Val Thr Leu Thr
1               5

<210> SEQ ID NO 31
<211> LENGTH: 5
<212> TYPE: PRT
<213> ORGANISM: Homo sapiens

<400> SEQUENCE: 31

Asn Leu Thr Arg Pro
1               5

<210> SEQ ID NO 32
<211> LENGTH: 5
<212> TYPE: PRT
<213> ORGANISM: Artificial Sequence
<220> FEATURE:
<223> OTHER INFORMATION: N-gly8 Glycan shift from N667 to L668)

<400> SEQUENCE: 32

Leu Asn Val Thr Ala
1               5

<210> SEQ ID NO 33
<211> LENGTH: 12
<212> TYPE: PRT
<213> ORGANISM: Homo sapiens

<400> SEQUENCE: 33

Asp Val Phe Gln Ala His Gln Glu Asp Thr Glu Arg
1               5                   10

<210> SEQ ID NO 34
<211> LENGTH: 13
<212> TYPE: PRT
<213> ORGANISM: Homo sapiens

<400> SEQUENCE: 34

Glu Leu Leu Arg Asp Pro Ser Leu Gly Ala Gln Phe Arg
1               5                   10

<210> SEQ ID NO 35
<211> LENGTH: 23
<212> TYPE: PRT
<213> ORGANISM: Homo sapiens

<400> SEQUENCE: 35

Lys Met Val Ile Leu Thr Glu Pro Glu Gly Ala Pro Asn Ile Thr Ala
1               5                   10                  15

Asn Leu Thr Ser Ser Leu Leu
            20

-continued

```
<210> SEQ ID NO 36
<211> LENGTH: 11
<212> TYPE: PRT
<213> ORGANISM: Homo sapiens

<400> SEQUENCE: 36

Gln Thr Ile Asn Pro Glu Asp Asp Thr Asp Pro
1               5                   10

<210> SEQ ID NO 37
<211> LENGTH: 12
<212> TYPE: PRT
<213> ORGANISM: Homo sapiens

<400> SEQUENCE: 37

Arg Phe Asp Leu Glu Leu Pro Asp Gly Asn Arg Gln
1               5                   10

<210> SEQ ID NO 38
<211> LENGTH: 10
<212> TYPE: PRT
<213> ORGANISM: Homo sapiens

<400> SEQUENCE: 38

Gln Leu Gly Gly Ala Cys Ser Pro Thr Trp
1               5                   10

<210> SEQ ID NO 39
<211> LENGTH: 13
<212> TYPE: PRT
<213> ORGANISM: Homo sapiens

<400> SEQUENCE: 39

Glu His Asp Gly Ala Pro Gly Ser Gly Cys Gly Pro Ser
1               5                   10

<210> SEQ ID NO 40
<211> LENGTH: 10
<212> TYPE: PRT
<213> ORGANISM: Homo sapiens

<400> SEQUENCE: 40

Ser Asp Gly Ala Ala Pro Arg Ala Gly Leu
1               5                   10

<210> SEQ ID NO 41
<211> LENGTH: 37
<212> TYPE: PRT
<213> ORGANISM: Homo sapiens

<400> SEQUENCE: 41

Pro Cys Ser Arg Arg Gln Leu Leu Ser Leu Leu Ser Ala Gly Arg Ala
1               5                   10                  15

Arg Cys Val Trp Asp Pro Pro Arg Pro Gln Pro Gly Ser Ala Gly His
                20                  25                  30

Pro Pro Asp Ala Gln
            35

<210> SEQ ID NO 42
<211> LENGTH: 22
<212> TYPE: PRT
<213> ORGANISM: Homo sapiens
```

-continued

```
<400> SEQUENCE: 42

Arg Val Ala Phe Gly Pro Lys Ala Val Ala Cys Thr Phe Ala Arg Glu
1               5                   10                  15

His Leu Asp Met Cys Gln
            20

<210> SEQ ID NO 43
<211> LENGTH: 13
<212> TYPE: PRT
<213> ORGANISM: Homo sapiens

<400> SEQUENCE: 43

Thr Asp Pro Leu Asp Gln Ser Ser Cys Ser Arg Leu Leu
1               5                   10

<210> SEQ ID NO 44
<211> LENGTH: 9
<212> TYPE: PRT
<213> ORGANISM: Homo sapiens

<400> SEQUENCE: 44

Asp Gly Thr Glu Cys Gly Val Glu Lys
1               5

<210> SEQ ID NO 45
<211> LENGTH: 32
<212> TYPE: PRT
<213> ORGANISM: Homo sapiens

<400> SEQUENCE: 45

Lys Gly Arg Cys Arg Ser Leu Val Glu Leu Thr Pro Ile Ala Ala Val
1               5                   10                  15

His Gly Arg Trp Ser Ser Trp Gly Pro Arg Ser Pro Cys Ser Arg Ser
            20                  25                  30

<210> SEQ ID NO 46
<211> LENGTH: 4
<212> TYPE: PRT
<213> ORGANISM: Homo sapiens

<400> SEQUENCE: 46

Arg Arg Arg Gln
1

<210> SEQ ID NO 47
<211> LENGTH: 13
<212> TYPE: PRT
<213> ORGANISM: Homo sapiens

<400> SEQUENCE: 47

Gly Gly Arg Ala Cys Val Gly Ala Asp Leu Gln Ala Glu
1               5                   10

<210> SEQ ID NO 48
<211> LENGTH: 11
<212> TYPE: PRT
<213> ORGANISM: Homo sapiens

<400> SEQUENCE: 48

Asn Thr Gln Ala Cys Glu Lys Thr Gln Leu Glu
1               5                   10

<210> SEQ ID NO 49
```

```
<211> LENGTH: 18
<212> TYPE: PRT
<213> ORGANISM: Homo sapiens

<400> SEQUENCE: 49

Gln Gln Cys Ala Arg Thr Asp Gly Gln Pro Leu Arg Ser Ser Pro Gly
1               5                   10                  15

Gly Ala

<210> SEQ ID NO 50
<211> LENGTH: 18
<212> TYPE: PRT
<213> ORGANISM: Homo sapiens

<400> SEQUENCE: 50

Phe Tyr His Trp Gly Ala Ala Val Pro His Ser Gln Gly Asp Ala Leu
1               5                   10                  15

Cys Arg

<210> SEQ ID NO 51
<211> LENGTH: 16
<212> TYPE: PRT
<213> ORGANISM: Homo sapiens

<400> SEQUENCE: 51

Arg Ala Ile Gly Glu Ser Phe Ile Met Lys Arg Gly Asp Ser Phe Leu
1               5                   10                  15

<210> SEQ ID NO 52
<211> LENGTH: 5
<212> TYPE: PRT
<213> ORGANISM: Homo sapiens

<400> SEQUENCE: 52

Ser Gly Pro Arg Glu
1               5

<210> SEQ ID NO 53
<211> LENGTH: 5
<212> TYPE: PRT
<213> ORGANISM: Homo sapiens

<400> SEQUENCE: 53

Ser Gly Ser Cys Arg
1               5

<210> SEQ ID NO 54
<211> LENGTH: 12
<212> TYPE: PRT
<213> ORGANISM: Homo sapiens

<400> SEQUENCE: 54

Asp Gly Arg Met Asp Ser Gln Gln Val Trp Asp Arg
1               5                   10

<210> SEQ ID NO 55
<211> LENGTH: 23
<212> TYPE: PRT
<213> ORGANISM: Homo sapiens

<400> SEQUENCE: 55

Val Cys Gly Gly Asp Asn Ser Thr Cys Ser Pro Arg Lys Gly Ser Phe
1               5                   10                  15
```

```
Thr Ala Gly Arg Ala Arg Glu
            20

<210> SEQ ID NO 56
<211> LENGTH: 8
<212> TYPE: PRT
<213> ORGANISM: Homo sapiens

<400> SEQUENCE: 56

Thr Phe Leu Thr Val Thr Pro Asn
1               5

<210> SEQ ID NO 57
<211> LENGTH: 9
<212> TYPE: PRT
<213> ORGANISM: Homo sapiens

<400> SEQUENCE: 57

Tyr Ile Ala Asn His Arg Pro Leu Phe
1               5

<210> SEQ ID NO 58
<211> LENGTH: 15
<212> TYPE: PRT
<213> ORGANISM: Homo sapiens

<400> SEQUENCE: 58

Gly Gly Arg Tyr Val Val Ala Gly Lys Met Ser Ile Ser Pro Asn
1               5                   10                  15

<210> SEQ ID NO 59
<211> LENGTH: 7
<212> TYPE: PRT
<213> ORGANISM: Homo sapiens

<400> SEQUENCE: 59

Tyr Pro Ser Leu Leu Glu Asp
1               5

<210> SEQ ID NO 60
<211> LENGTH: 11
<212> TYPE: PRT
<213> ORGANISM: Homo sapiens

<400> SEQUENCE: 60

Arg Val Ala Leu Thr Glu Asp Arg Leu Pro Arg
1               5                   10

<210> SEQ ID NO 61
<211> LENGTH: 9
<212> TYPE: PRT
<213> ORGANISM: Homo sapiens

<400> SEQUENCE: 61

Arg Ile Trp Gly Pro Leu Gln Glu Asp
1               5

<210> SEQ ID NO 62
<211> LENGTH: 12
<212> TYPE: PRT
<213> ORGANISM: Homo sapiens

<400> SEQUENCE: 62

Arg Arg Tyr Gly Glu Glu Tyr Gly Asn Leu Thr Arg
1               5                   10
```

<210> SEQ ID NO 63
<211> LENGTH: 8
<212> TYPE: PRT
<213> ORGANISM: Homo sapiens

<400> SEQUENCE: 63

Thr Phe Thr Tyr Phe Gln Pro Lys
1               5

<210> SEQ ID NO 64
<211> LENGTH: 15
<212> TYPE: PRT
<213> ORGANISM: Homo sapiens

<400> SEQUENCE: 64

Pro Arg Gln Ala Trp Val Trp Ala Ala Val Arg Gly Pro Cys Ser
1               5                   10                  15

<210> SEQ ID NO 65
<211> LENGTH: 20
<212> TYPE: PRT
<213> ORGANISM: Homo sapiens

<400> SEQUENCE: 65

Ala Gly Leu Arg Trp Val Asn Tyr Ser Cys Leu Asp Gln Ala Arg Lys
1               5                   10                  15

Glu Leu Val Glu
            20

<210> SEQ ID NO 66
<211> LENGTH: 17
<212> TYPE: PRT
<213> ORGANISM: Homo sapiens

<400> SEQUENCE: 66

Gln Gly Ser Gln Gln Pro Pro Ala Trp Pro Glu Ala Cys Val Leu Glu
1               5                   10                  15

Pro

<210> SEQ ID NO 67
<211> LENGTH: 17
<212> TYPE: PRT
<213> ORGANISM: Homo sapiens

<400> SEQUENCE: 67

Pro Pro Tyr Trp Ala Val Gly Asp Phe Gly Pro Cys Ser Ala Ser Cys
1               5                   10                  15

Gly

<210> SEQ ID NO 68
<211> LENGTH: 16
<212> TYPE: PRT
<213> ORGANISM: Homo sapiens

<400> SEQUENCE: 68

Leu Arg Glu Arg Pro Val Arg Cys Val Glu Ala Gln Gly Ser Leu Leu
1               5                   10                  15

<210> SEQ ID NO 69
<211> LENGTH: 27
<212> TYPE: PRT
<213> ORGANISM: Homo sapiens -continued

<400> SEQUENCE: 69

Pro Pro Ala Arg Cys Arg Ala Gly Ala Gln Gln Pro Ala Val Ala Leu
1               5                   10                  15

Glu Thr Cys Asn Pro Gln Pro Cys Pro Ala Arg
            20                  25

<210> SEQ ID NO 70
<211> LENGTH: 17
<212> TYPE: PRT
<213> ORGANISM: Homo sapiens

<400> SEQUENCE: 70

Trp Glu Val Ser Glu Pro Ser Ser Cys Thr Ser Ala Gly Gly Ala Gly
1               5                   10                  15

Leu

<210> SEQ ID NO 71
<211> LENGTH: 6
<212> TYPE: PRT
<213> ORGANISM: Homo sapiens

<400> SEQUENCE: 71

Asn Glu Thr Cys Val Pro
1               5

<210> SEQ ID NO 72
<211> LENGTH: 15
<212> TYPE: PRT
<213> ORGANISM: Homo sapiens

<400> SEQUENCE: 72

Leu Glu Ala Pro Val Thr Glu Gly Pro Gly Ser Val Asp Glu Lys
1               5                   10                  15

<210> SEQ ID NO 73
<211> LENGTH: 13
<212> TYPE: PRT
<213> ORGANISM: Homo sapiens

<400> SEQUENCE: 73

Ala Pro Glu Pro Cys Val Gly Met Ser Cys Pro Pro Gly
1               5                   10

<210> SEQ ID NO 74
<211> LENGTH: 11
<212> TYPE: PRT
<213> ORGANISM: Homo sapiens

<400> SEQUENCE: 74

Leu Asp Ala Thr Ser Ala Gly Glu Lys Ala Pro
1               5                   10

<210> SEQ ID NO 75
<211> LENGTH: 16
<212> TYPE: PRT
<213> ORGANISM: Homo sapiens

<400> SEQUENCE: 75

Ser Pro Trp Gly Ser Ile Arg Thr Gly Ala Gln Ala Ala His Val Trp
1               5                   10                  15

<210> SEQ ID NO 76

```
<211> LENGTH: 5
<212> TYPE: PRT
<213> ORGANISM: Homo sapiens

<400> SEQUENCE: 76

Val Ser Cys Gly Arg
1               5

<210> SEQ ID NO 77
<211> LENGTH: 22
<212> TYPE: PRT
<213> ORGANISM: Homo sapiens

<400> SEQUENCE: 77

Glu Leu Arg Phe Leu Cys Met Asp Ser Ala Leu Arg Val Pro Val Gln
1               5                   10                  15

Glu Glu Leu Cys Gly Leu
            20

<210> SEQ ID NO 78
<211> LENGTH: 25
<212> TYPE: PRT
<213> ORGANISM: Homo sapiens

<400> SEQUENCE: 78

Lys Pro Gly Ser Arg Arg Glu Cys Pro Ala Arg Trp Gln Tyr Lys Leu
1               5                   10                  15

Ala Ala Cys Ser Val Ser Cys Gly Arg
            20                  25

<210> SEQ ID NO 79
<211> LENGTH: 13
<212> TYPE: PRT
<213> ORGANISM: Homo sapiens

<400> SEQUENCE: 79

Arg Arg Ile Leu Tyr Cys Ala Arg Ala His Gly Glu Asp
1               5                   10

<210> SEQ ID NO 80
<211> LENGTH: 25
<212> TYPE: PRT
<213> ORGANISM: Homo sapiens

<400> SEQUENCE: 80

Glu Glu Ile Leu Leu Asp Thr Gln Cys Gln Gly Leu Pro Arg Pro Glu
1               5                   10                  15

Pro Gln Glu Ala Cys Ser Leu Glu Pro
            20                  25

<210> SEQ ID NO 81
<211> LENGTH: 5
<212> TYPE: PRT
<213> ORGANISM: Homo sapiens

<400> SEQUENCE: 81

Cys Pro Pro Arg Trp
1               5

<210> SEQ ID NO 82
<211> LENGTH: 12
<212> TYPE: PRT
<213> ORGANISM: Homo sapiens
```

<400> SEQUENCE: 82

```
Pro Cys Ser Ala Ser Cys Gly Leu Gly Thr Ala Arg
1               5                   10
```

<210> SEQ ID NO 83
<211> LENGTH: 15
<212> TYPE: PRT
<213> ORGANISM: Homo sapiens

<400> SEQUENCE: 83

```
Val Gln Leu Asp Gln Gly Gln Asp Val Glu Val Asp Glu Ala Ala
1               5                   10                  15
```

<210> SEQ ID NO 84
<211> LENGTH: 14
<212> TYPE: PRT
<213> ORGANISM: Homo sapiens

<400> SEQUENCE: 84

```
Leu Val Arg Pro Glu Ala Ser Val Pro Cys Leu Ile Ala Asp
1               5                   10
```

<210> SEQ ID NO 85
<211> LENGTH: 16
<212> TYPE: PRT
<213> ORGANISM: Homo sapiens

<400> SEQUENCE: 85

```
Arg Trp His Val Gly Thr Trp Met Glu Cys Ser Val Ser Cys Gly Asp
1               5                   10                  15
```

<210> SEQ ID NO 86
<211> LENGTH: 14
<212> TYPE: PRT
<213> ORGANISM: Homo sapiens

<400> SEQUENCE: 86

```
Ala Gln Ala Pro Val Pro Ala Asp Phe Cys Gln His Leu Pro
1               5                   10
```

<210> SEQ ID NO 87
<211> LENGTH: 27
<212> TYPE: PRT
<213> ORGANISM: Homo sapiens

<400> SEQUENCE: 87

```
Arg Gly Cys Trp Ala Gly Pro Cys Val Gly Gln Gly Thr Pro Ser Leu
1               5                   10                  15

Val Pro His Glu Glu Ala Ala Ala Pro Gly Arg
            20                  25
```

<210> SEQ ID NO 88
<211> LENGTH: 8
<212> TYPE: PRT
<213> ORGANISM: Homo sapiens

<400> SEQUENCE: 88

```
Pro Ala Gly Ala Ser Leu Glu Trp
1               5
```

<210> SEQ ID NO 89
<211> LENGTH: 22
<212> TYPE: PRT
<213> ORGANISM: Homo sapiens

<400> SEQUENCE: 89

Arg Gly Leu Leu Phe Ser Pro Ala Pro Gln Pro Arg Arg Leu Leu Pro
1               5                   10                  15

Gly Pro Gln Glu Asn Ser
            20

<210> SEQ ID NO 90
<211> LENGTH: 11
<212> TYPE: PRT
<213> ORGANISM: Homo sapiens

<400> SEQUENCE: 90

Cys Gly Arg Gln His Leu Glu Pro Thr Gly Thr
1               5                   10

<210> SEQ ID NO 91
<211> LENGTH: 9
<212> TYPE: PRT
<213> ORGANISM: Homo sapiens

<400> SEQUENCE: 91

Asp Met Arg Gly Pro Gly Gln Ala Asp
1               5

<210> SEQ ID NO 92
<211> LENGTH: 6
<212> TYPE: PRT
<213> ORGANISM: Homo sapiens

<400> SEQUENCE: 92

Gly Arg Pro Leu Gly Glu
1               5

<210> SEQ ID NO 93
<211> LENGTH: 5
<212> TYPE: PRT
<213> ORGANISM: Homo sapiens

<400> SEQUENCE: 93

Pro Gly Gln Ala Asp
1               5

<210> SEQ ID NO 94
<211> LENGTH: 17
<212> TYPE: PRT
<213> ORGANISM: Homo sapiens

<400> SEQUENCE: 94

Ser Ser Leu Asn Cys Ser Ala Gly Asp Met Leu Leu Leu Trp Gly Arg
1               5                   10                  15

Leu

<210> SEQ ID NO 95
<211> LENGTH: 9
<212> TYPE: PRT
<213> ORGANISM: Homo sapiens

<400> SEQUENCE: 95

Asn Cys Ser Ala Gly Asp Met Leu Leu
1               5

<210> SEQ ID NO 96

```
<211> LENGTH: 16
<212> TYPE: PRT
<213> ORGANISM: Homo sapiens

<400> SEQUENCE: 96

Trp Gly Arg Leu Thr Trp Arg Lys Met Cys Arg Lys Leu Leu Asp Met
1               5                   10                  15

<210> SEQ ID NO 97
<211> LENGTH: 11
<212> TYPE: PRT
<213> ORGANISM: Homo sapiens

<400> SEQUENCE: 97

Trp Arg Lys Met Cys Arg Lys Leu Leu Asp Met
1               5                   10

<210> SEQ ID NO 98
<211> LENGTH: 8
<212> TYPE: PRT
<213> ORGANISM: Homo sapiens

<400> SEQUENCE: 98

Thr Phe Ser Ser Lys Thr Asn Thr
1               5

<210> SEQ ID NO 99
<211> LENGTH: 4
<212> TYPE: PRT
<213> ORGANISM: Homo sapiens

<400> SEQUENCE: 99

Lys Thr Asn Thr
1

<210> SEQ ID NO 100
<211> LENGTH: 11
<212> TYPE: PRT
<213> ORGANISM: Homo sapiens

<400> SEQUENCE: 100

Arg Gln Arg Ser Gly Arg Pro Gly Gly Gly Val
1               5                   10

<210> SEQ ID NO 101
<211> LENGTH: 6
<212> TYPE: PRT
<213> ORGANISM: Homo sapiens

<400> SEQUENCE: 101

Arg Cys Gly Arg Pro Gly
1               5

<210> SEQ ID NO 102
<211> LENGTH: 14
<212> TYPE: PRT
<213> ORGANISM: Homo sapiens

<400> SEQUENCE: 102

Arg Tyr Gly Ser Gln Leu Ala Pro Glu Thr Phe Tyr Arg Glu
1               5                   10

<210> SEQ ID NO 103
<211> LENGTH: 10
<212> TYPE: PRT
```

<213> ORGANISM: Homo sapiens

<400> SEQUENCE: 103

```
Gln Leu Ala Pro Glu Thr Phe Tyr Arg Glu
1               5                   10
```

<210> SEQ ID NO 104
<211> LENGTH: 9
<212> TYPE: PRT
<213> ORGANISM: Homo sapiens

<400> SEQUENCE: 104

```
Asp Met Gln Leu Phe Gly Pro Trp Gly
1               5
```

<210> SEQ ID NO 105
<211> LENGTH: 23
<212> TYPE: PRT
<213> ORGANISM: Homo sapiens

<400> SEQUENCE: 105

```
Asp Met Gln Leu Phe Gly Pro Trp Gly Glu Ile Val Ser Pro Ser Leu
1               5                   10                  15

Ser Pro Ala Thr Ser Asn Ala
            20
```

<210> SEQ ID NO 106
<211> LENGTH: 13
<212> TYPE: PRT
<213> ORGANISM: Homo sapiens

<400> SEQUENCE: 106

```
Ser Pro Ser Leu Ser Pro Ala Thr Ser Asn Ala Gly Gly
1               5                   10
```

<210> SEQ ID NO 107
<211> LENGTH: 12
<212> TYPE: PRT
<213> ORGANISM: Homo sapiens

<400> SEQUENCE: 107

```
Arg Leu Phe Ile Asn Val Ala Pro His Ala Arg Ile
1               5                   10
```

<210> SEQ ID NO 108
<211> LENGTH: 5
<212> TYPE: PRT
<213> ORGANISM: Homo sapiens

<400> SEQUENCE: 108

```
Ala Pro His Ala Arg
1               5
```

<210> SEQ ID NO 109
<211> LENGTH: 16
<212> TYPE: PRT
<213> ORGANISM: Homo sapiens

<400> SEQUENCE: 109

```
Thr Asn Met Gly Ala Gly Thr Glu Gly Ala Asn Ala Ser Tyr Ile Leu
1               5                   10                  15
```

<210> SEQ ID NO 110
<211> LENGTH: 7

```
<212> TYPE: PRT
<213> ORGANISM: Homo sapiens

<400> SEQUENCE: 110

Ala Gly Thr Glu Gly Ala Asn
1               5

<210> SEQ ID NO 111
<211> LENGTH: 9
<212> TYPE: PRT
<213> ORGANISM: Homo sapiens

<400> SEQUENCE: 111

Ile Arg Asp Thr His Ser Leu Arg Thr
1               5

<210> SEQ ID NO 112
<211> LENGTH: 11
<212> TYPE: PRT
<213> ORGANISM: Homo sapiens

<400> SEQUENCE: 112

Arg Asp Thr His Ser Leu Arg Thr Thr Ala Phe
1               5               10

<210> SEQ ID NO 113
<211> LENGTH: 12
<212> TYPE: PRT
<213> ORGANISM: Homo sapiens

<400> SEQUENCE: 113

Gln Gln Val Leu Tyr Trp Glu Ser Glu Ser Ser Gln
1               5               10

<210> SEQ ID NO 114
<211> LENGTH: 9
<212> TYPE: PRT
<213> ORGANISM: Homo sapiens

<400> SEQUENCE: 114

Trp Glu Ser Glu Ser Ser Gln Ala Glu
1               5

<210> SEQ ID NO 115
<211> LENGTH: 12
<212> TYPE: PRT
<213> ORGANISM: Homo sapiens

<400> SEQUENCE: 115

Glu Phe Ser Glu Gly Phe Leu Lys Ala Gln Ala Ser
1               5               10

<210> SEQ ID NO 116
<211> LENGTH: 15
<212> TYPE: PRT
<213> ORGANISM: Homo sapiens

<400> SEQUENCE: 116

Ser Glu Gly Phe Leu Lys Ala Gln Ala Ser Leu Arg Gly Gln Tyr
1               5               10              15

<210> SEQ ID NO 117
<211> LENGTH: 20
<212> TYPE: PRT
<213> ORGANISM: Homo sapiens
```

-continued

```
<400> SEQUENCE: 117

Leu Gln Ser Trp Val Pro Glu Met Gln Asp Pro Gln Ser Trp Lys Gly
1               5                   10                  15

Lys Glu Gly Thr
            20

<210> SEQ ID NO 118
<211> LENGTH: 4
<212> TYPE: PRT
<213> ORGANISM: Homo sapiens

<400> SEQUENCE: 118

Arg Leu Pro Leu
1

<210> SEQ ID NO 119
<211> LENGTH: 4
<212> TYPE: PRT
<213> ORGANISM: Homo sapiens

<400> SEQUENCE: 119

Tyr Gly Asn Leu
1

<210> SEQ ID NO 120
<211> LENGTH: 4
<212> TYPE: PRT
<213> ORGANISM: Artificial Sequence
<220> FEATURE:
<223> OTHER INFORMATION: NGLY7

<400> SEQUENCE: 120

Asn Val Thr Leu
1

<210> SEQ ID NO 121
<211> LENGTH: 5
<212> TYPE: PRT
<213> ORGANISM: Homo sapiens

<400> SEQUENCE: 121

Asn Leu Thr Arg Pro
1               5

<210> SEQ ID NO 122
<211> LENGTH: 5
<212> TYPE: PRT
<213> ORGANISM: Artificial Sequence
<220> FEATURE:
<223> OTHER INFORMATION: NGLY8

<400> SEQUENCE: 122

Leu Asn Val Thr Ala
1               5
```

ADAMTS13 PROTEIN VARIANTS AND USES THEREOF

CROSS-REFERENCE TO RELATED PATENT APPLICATIONS

This application is a U.S. National Stage Application under 35 U.S.C. § 371 of International Patent Application No. PCT/NL2021/050325, filed May 25, 2021, which claims the benefit of priority of European Patent Application No. 20176333.1 filed May 25, 2020, both of which are incorporated herein by reference in their entireties. The International Application was published on Dec. 2, 2021, as International Publication No. WO 2021/242092 A1.

SEQUENCE LISTING

The instant application contains a Sequences Listing which has been submitted electronically in ASCII format and is hereby incorporated by reference in its entirety. Said ASCII copy, created on Nov. 23, 2022, is named AS FILED—P126141US00-Sequence Listing 10114/011562-USO and is 36,864 bytes in size.

This invention was made with support from the European Union's Horizon 2020 research and innovation program under the Marie Sklodowska-Curie grant agreement No 675746 (project PROFILE).

FIELD OF THE INVENTION

The invention relates to the field of therapy. More specifically, the invention relates to the field of therapy of disorders in which von Willebrand Factor (VWF) is involved. The invention relates to modified proteases involved in maintaining hemostasis, specifically to modified proteases which display strongly reduced binding of autoantibodies while retaining activity and their use in treatment of disease.

BACKGROUND OF THE INVENTION

Immune-mediated thrombotic thrombocytopeniaurpura (iTTP) is a rare but a life-threatening autoimmune disease that results from the development of autoantibodies directed towards ADAMTS13 (A Disintegrin And Metalloproteinase with ThromboSpondin type 1 motifs, member 13). ADAMTS13 is a metalloprotease that proteolytically cleaves the Tyr1605-Met1606 bond in the A2 domain of Von Willebrand Factor (VWF). VWF is a multimeric protein that mediates the adhesion of blood platelets to a damaged vessel. The multimeric size of VWF is directly proportional to its biological activity, the larger multimers being highly active in promoting the adhesion of platelets to a damaged vessel wall. In normal individuals, multimer size of VWF is controlled by the VWF cleaving protease ADAMTS13. Processing of VWF multimers in patients with iTTP is impaired due to the presence of pathogenic autoantibodies directed towards ADAMTS13 that develop in these patients. The persistence of high molecular weight VWF multimers in iTTP patients with autoantibodies directed towards ADAMTS13 is linked to excessive thrombus formation in the microvasculature presenting with life-threatening microvascular thrombosis.

Current management of iTTP involves plasma exchange (PEX) and immunosuppression with high dose glucocorticoids. Plasma exchange provides a source of exogenous ADAMTS13 which actions are short-lived due to the persistent presence of circulating pathogenic antibodies targeting ADAMTS13, including exogenous ADAMTS13. In addition to plasma exchange, Rituximab, a B-cell depleting anti-CD20 therapeutic monoclonal antibody, is used in the treatment of iTTP. Rituximab is also being used to prevent relapses in patients with iTTP. Recently, Caplacizumab, a humanized anti-VWF nanobody which blocks platelet binding to VWF has been shown to accelerate normalization of platelet counts 1.55 fold (Scully et al., 2019). Bleeding provides a side-effect of treatment with Caplacizumab (Mazepa et al., 2019). Mazepa et al showed that bleeding was the primary adverse effect of caplacizumab therapy and occurred in 65% (vs 48% in the placebo arm) in HERCU-LES clinical trial. Mucocutaneous bleeding including epistaxis and gingival bleeding were the most common events, and most bleeding was of mild to moderate severity that resolved without intervention. Three subjects that developed severe bleeding on caplacizumab received VWF concentrate (severe epistaxis), tranexamic acid (for gingival bleeding), and a red cell transfusion (for upper gastrointestinal bleeding). Overall, most caplacizumab-related bleeding resolve without intervention (though it may be necessary to withhold the drug), whereas topical vasoconstrictors and antifibrinolytics are effective in others, with VWF concentrates reserved for patients with severe, refractory bleeding.

Despite the advancements in treatment of patients with iTTP, current treatment regimes are thus still suboptimal. There is clearly a need for treatment that quickly re-establishes ADAMTS13 activity that would help to accelerate the normalization of platelet counts in patients with iTTP.

Autoantibody resistant ADAMTS13 variants have been reported in the literature (Jian et al., 2012). The spacer domain of ADAMTS13 provides a major site for the binding of pathogenic autoantibodies. Conservative mutations in 5 residues within the spacer domain has created a so-called Gain-of-Function (GoF) variant that was claimed to be resistant to the binding of pathogenic autoantibodies that develop in patients with iTTP (Jian et al., 2012). This GoF variant of ADAMTS13 is also described in U.S. Pat. No. 9/546,360. However, follow-up experiments revealed that this GoF variant of ADAMTS13 is still targeted by patient-derived autoantibodies and does not resist their inhibitory action (Graça et al., 2019). However, pathogenic autoantibodies that bind to other domains of ADAMTS13 have also been reported.

Hence, there is still a need for ADAMTS13 variants which effectively escape from binding of autoantibodies while retaining ADAMTS13 activity. Such ADAMTS13 variants could be of great therapeutic interest based on their potential to rapidly correct the clinical symptoms in patients with iTTP and other related diseases when compared to currently available treatment options.

SUMMARY OF THE INVENTION

It is an object of the present invention to provide improved ADAMTS13 variants that are less susceptible to binding by autoantibodies and that retain proteolytic activity.

The invention therefore provides an ADAMTS13 protein variant comprising residues 1 to 1427 of ADAMTS13 or a truncated version of ADAMTS13 containing at least residues 1 to 685 and wherein one or more N-linked glycosylation sites are added as compared to wild-type ADAMTS13 and/or one or more existing N-linked glycosylation sites are shifted as compared to wild-type ADAMTS13. Preferably said one or more N-linked glycosylation sites are not added to and said one or more existing N-linked glycosylation sites are not shifted to amino acid residues 464-466, 469-471, 476-478, 493-495, 511-513 and 539-541 of said ADAMTS13 protein variant. In another preferred embodiment, said N-linked glycosylation site is not present at amino acid residues 464-466, 469-471, 476-478, 493-495, 511-513 and 539-541 of said ADAMTS13 protein variant. In one preferred embodiment, the ADAMTS13 protein variant is a full length ADAMTS13 variant, i.e. comprising residues 1 to 1427 of ADAMTS13, wherein one or more N-linked glycosylation sites are added as compared to wild-type ADAMTS13 and/or one or more existing N-linked glycosylation sites are shifted as compared to wild-type ADAMTS13 and optionally comprising additional mutations as described herein.

In a further aspect, the invention provides a nucleic acid construct comprising a nucleic acid sequence encoding an ADAMTS13 protein variant according to the invention.

In a further aspect, the invention provides a pharmaceutical composition comprising an ADAMTS13 protein variant according to the invention or a nucleic acid construct according to the invention and one or more pharmaceutically acceptable carriers, adjuvants, excipients and/or diluents.

In a further aspect, the invention provides an ADAMTS13 protein variant comprising residues 1 to 685 of ADAMTS13 and wherein one or more N-linked glycosylation sites are added as compared to wild-type ADAMTS13 and/or one or more existing N-linked glycosylation sites are shifted as compared to wild-type ADAMTS13 or a nucleic acid construct comprising a nucleic acid sequence encoding said ADAMTS13 variant, preferably an ADAMTS13 protein variant or a nucleic acid construct according to the invention, for use in therapy.

In a further aspect, the invention provides an ADAMTS13 protein variant comprising residues 1 to 685 of ADAMTS13 and wherein one or more N-linked glycosylation sites are added as compared to wild-type ADAMTS13 and/or one or more existing N-linked glycosylation sites are shifted as compared to wild-type ADAMTS13 or a nucleic acid construct comprising a nucleic acid sequence encoding said ADAMTS13 variant, preferably an ADAMTS13 protein variant or a nucleic acid construct according to the invention, for use as an antithrombotic agent.

In a further aspect, the invention provides an ADAMTS13 protein variant comprising residues 1 to 685 of ADAMTS13 and wherein one or more N-linked glycosylation sites are added as compared to wild-type ADAMTS13 and/or one or more existing N-linked glycosylation sites are shifted as compared to wild-type ADAMTS13 or a nucleic acid construct comprising a nucleic acid sequence encoding said ADAMTS13 variant, preferably an ADAMTS13 protein variant or a nucleic acid construct according to the invention, for use in the treatment of a disorder characterized by aberrant Von Willebrand Factor (VWF) activity and/or VWF processing.

In a further aspect, the invention provides a method for the treatment of a disorder characterized by aberrant Von Willebrand Factor (VWF) activity and/or VWF processing comprising administering to a subject in need thereof a therapeutically effective amount of an ADAMTS13 protein variant comprising residues 1 to 685 of ADAMTS13 and wherein one or more N-linked glycosylation sites are added as compared to wild-type ADAMTS13 and/or one or more existing N-linked glycosylation sites are shifted as compared to wild-type ADAMTS13 or a nucleic acid construct comprising a nucleic acid sequence encoding said ADAMTS13 variant, preferably an ADAMTS13 protein variant or nucleic acid construct according to the invention.

In a further aspect, the invention provides a use of an ADAMTS13 protein variant comprising residues 1 to 685 of ADAMTS13 and wherein one or more N-linked glycosylation sites are added as compared to wild-type ADAMTS13 and/or one or more existing N-linked glycosylation sites are shifted as compared to wild-type ADAMTS13 or a nucleic acid construct comprising a nucleic acid sequence encoding said ADAMTS13 variant, preferably an ADAMTS13 protein variant or nucleic acid construct according to the invention, in the manufacture of a medicament for the treatment of a disorder characterized by aberrant Von Willebrand Factor (VWF) activity and/or VWF processing.

In a further aspect, the invention provides an ADAMTS13 protein variant comprising residues 1 to 685 of ADAMTS13 and wherein one or more N-linked glycosylation sites are added as compared to wild-type ADAMTS13 and/or one or more existing N-linked glycosylation sites are shifted as compared to wild-type ADAMTS13 or a nucleic acid construct comprising a nucleic acid sequence encoding said ADAMTS13 variant, preferably an ADAMTS13 protein variant or a nucleic acid construct according to the invention, for use in the treatment of a thrombotic disease.

In a further aspect, the invention provides a method for the treatment of a thrombotic disease, both acquired or congenital thrombotic disease, comprising administering to a subject in need thereof a therapeutically effective amount of an ADAMTS13 protein variant comprising residues 1 to 685 of ADAMTS13 and wherein one or more N-linked glycosylation sites are added as compared to wild-type ADAMTS13 and/or one or more existing N-linked glycosylation sites are shifted as compared to wild-type ADAMTS13 or a nucleic acid construct comprising a nucleic acid sequence encoding said ADAMTS13 variant, preferably an ADAMTS13 protein variant or nucleic acid construct according to the invention.

In a further aspect, the invention provides a use of an ADAMTS13 protein variant comprising residues 1 to 685 of ADAMTS13 and wherein one or more N-linked glycosylation sites are added as compared to wild-type ADAMTS13 and/or one or more existing N-linked glycosylation sites are shifted as compared to wild-type ADAMTS13 or a nucleic acid construct comprising a nucleic acid sequence encoding said ADAMTS13 variant, preferably an ADAMTS13 protein variant or nucleic acid construct according to the invention, in the manufacture of a medicament for the treatment of a thrombotic disease, both acquired or congenital thrombotic disease.

In a further aspect, the invention provides a method for producing an ADAMTS13 protein variant according to the invention, comprising introducing a nucleic acid molecule according to the invention into a host cell capable of N-linked glycosylation, preferably an eukaryotic host cell, and culturing said host cell under conditions that allow expression of said ADAMTS13 protein variant.

DETAILED DESCRIPTION

The present inventors have identified a novel strategy to develop ADAMTS13 variants with reduced binding to pathogenic autoantibodies, based on the insertion of novel consensus sites for the addition of an N-glycan. Such N-glycan consensus site is preferably inserted in immunogenic regions within ADAMTS13. As shown in the examples, amino acids mutations were introduced into the wildtype ADAMTS13 protein to introduce N-glycan sites at different locations. It is further demonstrated that this technique can be used to significantly reduce binding of pathogenic ADAMTS13 autoantibodies that develop in iTTP patients. Without wishing to be bound by theory, it is hypothesized that the introduced N-glycans are capable of shielding an epitope that is bound by autoantibodies. More specifically the introduced N-glycan shields epitopes bound by autoantibodies that target ADAMTS13, including epitopes bound by autoantibodies in the spacer domain, the TSP-1 (thrombospondin type 1) repeats and the CUB (Complement component Clr/Cls, Uegf, and Bone morphogenic protein 1), metalloprotease domains, disintegrin domain, cystine-rich domain and other domains and exposed regions in other domains of ADAMTS13 that provide binding sites for anti-ADAMTS13 autoantibodies. In particular, it is believed that shielding of a major epitope in the spacer domain of ADAMTS13 results in a significant reduction of reactivity with autoantibodies. This epitope in the spacer domain was believed to be centered around amino acid residues R568, F592, R660, Y661, Y665 in the ADAMTS13 sequence. Mutations in these 5 residues can effectively reduce binding of autoantibodies to ADAMTS13, yet they normally also result in activity loss (Graça et al, 2019). In the current invention it is demonstrated that an N-glycan can be introduced in and/or outside of the classic epitope residues (R568, F592, R660, Y661 and Y665) to reduce reactivity of ADAMTS13 with autoantibodies, without losing proteolytic activity, i.e. while retaining at least part of the VWF cleaving activity of ADAMTS13. Such ADAMTS13 N-glycan variants that resist autoantibodies targeting ADAMTS13 and retain binding of VWF to spacer domain, are of high interest for treatment of disorders associated with aberrant Von Willebrand Factor (VWF) activity and/or Von Willebrand Factor processing.

The invention therefore, in a first aspect, provides an ADAMTS13 protein variant comprising residues 1 to 685 of ADAMTS13 and wherein one of more N-glycosylation sites are added and/or one or more existing N-glycosylation sites are shifted as compared to wild-type ADAMTS13, with the proviso that said one or more N-linked glycosylation sites are not added to and said one or more existing N-linked glycosylation sites are not shifted to amino acid residues 464-466, 469-471, 476-478, 493-495, 511-513 and 539-541 of said ADAMTS13 protein variant.

In a further aspect, the invention provides an ADAMTS13 protein variant comprising residues 1 to 685 of ADAMTS13 and wherein one or more N-linked glycosylation sites are added as compared to wild-type ADAMTS13 and/or one or more existing N-linked glycosylation sites are shifted as compared to wild-type ADAMTS13 or a nucleic acid construct comprising a nucleic acid sequence encoding said ADAMTS13 variant for use in therapy.

In a further aspect, the invention provides an ADAMTS13 protein variant comprising residues 1 to 685 of ADAMTS13 and wherein one or more N-linked glycosylation sites are added as compared to wild-type ADAMTS13 and/or one or more existing N-linked glycosylation sites are shifted as compared to wild-type ADAMTS13 or a nucleic acid construct comprising a nucleic acid sequence encoding said ADAMTS13 variant for use as an antithrombotic agent.

In a further aspect, the invention provides an ADAMTS13 protein variant comprising residues 1 to 685 of ADAMTS13 and wherein one or more N-linked glycosylation sites are added as compared to wild-type ADAMTS13 and/or one or more existing N-linked glycosylation sites are shifted as compared to wild-type ADAMTS13 or a nucleic acid construct comprising a nucleic acid sequence encoding said ADAMTS13 variant for use in treatment of a disorder characterized by aberrant Von Willebrand Factor (VWF) activity and/or VWF processing.

The term "protein" as used herein refers to compounds comprising amino acids joined via peptide bonds. A protein encoded by a gene is not limited to the amino acid sequence encoded by a gene, but may include post-translational modifications of the protein.

As used herein the terms "ADAMTS13" and "ADAMTS13 protein" refers to a protein encoded by the ADAMTS13 gene. ADAMTS13 is a member of the metalloproteinase gene family, ADAM (a disintegrin and metalloproteinase), a family consisting of membrane-anchored proteases with different functions. ADAMTS family members are further characterized by the presence of one or more thrombospondin 1-like (TSP1) domain(s) at the C-terminus and the absence of an EGF repeat, a transmembrane domain and a cytoplasmic tail, present in ADAM metalloproteinases. ADAMTS13 is the only ADAMTS member to possess two C-terminal CUB domains (for complement Clr/Cls proteases, sea Urchin, and Bone morphogenic protein), and possesses VWF (von Willebrand factor) cleaving protease activity (Kelwick et al, 2015). The terms "wild-type ADAMTS13" and "wildtype ADAMTS13 protein" refer to naturally occurring, human ADAMTS13. FIG. 1 provides the amino acid sequence of full length wildtype ADAMTS13.

As used herein the term "ADAMTS13 protein variant" refers to a variant of ADAMTS13 that has an amino acid sequence that differs from the amino acid sequence of wildtype ADAMTS13 in that it has at least one N-glycosylation site that is not present in wildtype ADAMTS13. In addition, an ADAMTS13 protein variant according to the invention comprises at least amino acids 1 to 685 of the ADAMTS13 amino acid sequence as shown in FIG. 1. A shortened ADAMTS13 protein consisting of amino acids 1 to 685 as shown in FIG. 1 has been demonstrated to have proteolytic activity against VWF (Tao et al. 2005). In another preferred embodiment the ADAMTS13 protein variant according to the invention is a full length ADAMTS13 protein variant, meaning that it contains the full amino acid sequence with residues 1 to 1427 of ADAMTS13, as shown in FIG. 1 wherein one or more N-linked glycosylation sites are added as compared to wild-type ADAMTS13 and/or one or more existing N-linked glycosylation sites are shifted as compared to wild-type ADAMTS13, and optionally additional mutations as described herein.

In amino acid sequences or protein variants as defined herein, amino acids are denoted by single-letter or three-letter symbols. These single-letter and three-letter symbols are well known to the person skilled in the art and have the following meaning: A (Ala) is alanine, C (Cys) is cysteine, D (Asp) is aspartic acid, E (Glu) is glutamic acid, F (Phe) is phenylalanine, G (Gly) is glycine, H (His) is histidine, I (Ile) is isoleucine, K (Lys) is lysine, L (Leu) is leucine, M (Met) is methionine, N (Asn) is asparagine, P (Pro) is proline, Q (Gln) is glutamine, R (Arg) is arginine, S (Ser) is serine, T (Thr) is threonine, V (Val) is valine, W (Trp) is tryptophan, Y (Tyr) is tyrosine.

All positions of amino acid residues indicated herein refer to the numbering of amino acid residues in the sequence of wildtype ADAMTS13 depicted in FIG. 1.

Mutations, in particular substitutions of an amino acid by another amino acid, are indicated herein in a way that is standard in the art, i.e. by indicating the amino acid present in wildtype ADAMTS13 sequence, the position of the amino acid in the sequence, and the amino acid that is introduced at the position. E.g. "R568K" indicates that the arginine at position 568 is substituted by a lysine. "568REY570 to 568NET570" indicates that the sequence arginine-glutamic acid-tyrosine at positions 568-570 is substituted by the sequence asparagine-glutamic acid-threonine.

"N-linked glycosylation" refers to the attachment of an oligosaccharide moiety to a nitrogen atom, typically the N4 of an asparagine residue. The terms "N-linked glycosylation site" and "N glycosylation site" are used interchangeably and refer to a site in the ADAMTS13 protein variant where N-linked glycosylation is possible. Such site has the amino acid sequence NXT or NXS, wherein X is any amino acid except P. N-linked glycosylation is a posttranslational modification and N-linked glycans of a protein can modulate the folding, cell attachment and/or function of a protein. N-linked glycans can have different combinations of mannose, N-acetylglucosamine (GlcNAc), galactose, fucose and sialic acid residues. Several N-linked glycans have been identified on ADAMTS13 (Verbij et al. 2016)), attached to asparagine residues 142, 146, 552, 579, 614, 667, 707, 828, 1235 and 1354 (see FIG. 2), as well as several other types of glycosylation, including O-glycosylation and S- and C-mannosylation. FIG. 2 also shows the most common and other structures of N-glycans identified in ADAMTS13.

Introduction of a N-linked glycosylation site at residues 464-466, 469-471, 476-478, 493-495, 511-513 and 539-541 in the cysteine-rich domain of full length ADAMTS13 has been described by De Groot et al. Insertions of such sites, as well as sequence swaps, and single point mutations in this domain, were performed to study the functional role of the cysteine-rich domain of ADAMTS13 in binding to VWF and proteolysis.

In the ADAMTS13 protein variants according to the invention or used in accordance with the invention, one or more N-linked glycosylation sites are added as compared to wild-type ADAMTS13 and/or one or more existing N-linked glycosylation sites are shifted as compared to wild-type ADAMTS13. This means that an N glycosylation site (NXT or NXS, wherein X is any amino acid except P) is present at amino acid residues at which it is not present in the wildtype ADAMTS13. This can be achieved by either addition of one or more additional N-linked glycosylation site, shifting one or more N-linked glycosylation sites, or a combination thereof. Preferably between one and five N-linked glycosylation sites are added and/or shifted, more preferably between one and three, more preferably one or two.

In a further preferred embodiment, a proline (P) present in the ADAMTS13 sequence in the vicinity of the N-linked glycosylation site NXS or NXT that is introduced or shifted in accordance with the present invention is replaced by another amino acid, with replacement by alanine as a preferred example. Replacement of proline at such position facilitates attachment of an N-glycan to the N-linked glycosylation site. As used herein, in the vicinity means 1 or 2 amino acids preceding or following the N-linked glycosylation site. Preferably a proline immediately following the N-linked glycosylation site is replaced by another amino acid, with replacement by alanine as a preferred example.

Addition of an N-linked glycosylation site means that an N-linked glycosylation site is introduced in the ADAMTS13 protein variant of the invention that is not present in wild-type ADAMTS13, without removing any naturally occurring N-linked glycosylation sites that are present in wildtype ADAMTS13. Addition of an N-linked glycosylation site can be achieved by introducing one or more mutations in the amino acid sequence as compared to wildtype ADAMTS13 such that an N-linked glycosylation site is introduced. Such mutation can be one or more substitutions of amino acid residues by other amino acid residues, insertion of one or more amino acid residues or deletion of one or more amino acid residues or a combination thereof, in such a way that an N-linked glycosylation site is introduced in the ADAMTS13 sequence that is not present in wildtype ADAMTS13. In a preferred embodiment, an N-linked glycosylation site is added by one or more substitutions of an amino acid residue with another amino acid residue. In particular, any amino acid can be substituted with an asparagine residue to introduce an asparagine as the first residue in the N-linked glycosylation site NXS or NXT as defined herein, a proline can be substituted with any other amino acid to remove a potential proline as the second residue in the N-linked glycosylation site NXS or NXT as defined herein, any amino acid other than serine and threonine can be substituted with serine or threonine to introduce a serine or threonine as the third residue in the N-linked glycosylation site NXS or NXT as defined herein, or a combination thereof. Both NXS and NXT sites can be introduced in an ADAMTS13 variant in accordance with the invention or used in accordance with the invention, but NXT appears to result in more efficient N-glycan addition when compared to NXS. For instance, in ADAMTS13 variant NGLY3 described in the examples herein, an N-linked glycosylation site (NMS) is added at amino acid residues 608-610 by substituting a lysine at position 608 with an asparagine (K608N). As another example, in ADAMTS13 variant NGLY4 described in the examples herein, an N-linked glycosylation site (NST) is added at amino acid residues 609-611 by substituting a methionine at position 609 with an asparagine and substituting an isoleucine at position 611 with a threonine (609MSI611 to 609NST611). A skilled person is well capable of designing appropriate mutations in the ADAMTS13 sequence to add one or more N-linked glycosylation sites.

Shifting an N-linked glycosylation site means that an N-linked glycosylation site that is present at particular amino acid residues in wildtype ADAMTS13, in particular comprising an asparagine residue at amino acid position 142, 146, 552, 579, 614, 667, 707, 828, 1235 or 1354, is moved to other amino acid residues in the ADAMTS13 amino acid sequences. I.e. the total number of N-linked glycosylation sites in the ADAMTS13 protein variant wherein an N-linked glycosylation has been shifted is the same as the number of N-linked glycosylation sites in wildtype ADAMTS13. Preferably, the N-linked glycosylation site is shifted between 1 and 10 amino acid residues. Shifting can be either downstream or upstream as compared to the location of the N-linked glycosylation site in the wildtype ADAMTS13 sequence. More preferably the N-linked glycosylation site is shifted between 1 and 7 amino acids, more preferably between 1 and 5 amino acids, more preferably between 1 and 4 amino acids, more preferably between 1 and 3 amino acids, such as shifted one, two or three amino acid residues, either upstream or downstream as compared to the location of the N-linked glycosylation site in the wildtype ADAMTS13 sequence. In a preferred embodiment, the N-linked glycosylation site is shifted 1 or 2 amino acid residues, most preferably one amino acid residue. Shifting an N-linked glycosylation site can be achieved by introducing one or more mutations in the amino acid sequence as compared to wildtype ADAMTS13 such that an N-linked glycosylation site is shifted. Such mutations can be one or more substitutions of an amino acid residue by another amino acid residue, insertion of one or more amino acid residues or deletion of one or more amino acid residues, or a combination thereof, in such a way that the location of an N-linked glycosylation site is shifted as compared to the location of an N-linked glycosylation site in the wildtype ADAMTS13 sequence. In a preferred embodiment, an N-linked glycosylation site is shifted by one or more substitutions of an amino acid residue with another amino acid residue. In particular any amino acid can be substituted with an asparagine residue to introduce an asparagine as the first residue in the N-linked glycosylation site NXS or NXT as defined herein, a proline can be substituted with any other amino acid to remove a potential proline as the second residue in the N-linked glycosylation site NXS or NXT as defined herein, any amino acid other than serine and threonine can be substituted with serine or threonine to introduce a serine or threonine as the third residue in the N-linked glycosylation site NXS or NXT as defined herein, or a combination thereof. Alternatively or in addition, an asparagine can be substituted by any other amino acid to remove an N-linked glycosylation site that is present in wildtype ADAMTS13. As an example, in ADAMTS13 variant NGLY8 described in the examples herein, an N-linked glycosylation site is shifted from amino acid residues 667-669 to amino acid residues 668-670 by substituting an asparagine at position 667 with a leucine, substituting a leucine at position 668 with an asparagine, substituting a threonine at position 669 with a valine and substituting an arginine at position 670 with a threonine (667NLTR670 to 667LNVT670). In addition, the proline in position 671 was replaced by an alanine, which significantly increased the likelihood of N-glycan attachment (667NLTRP671 to 667LNVTA671). A skilled person is well capable of designing appropriate mutations in the ADAMTS13 sequence to shift one or more N-linked glycosylation sites.

In a preferred embodiment, the one or more N-linked glycosylation sites in an ADAMTS13 protein variant according to the invention or used in accordance with the invention are added as compared to wild-type ADAMTS13 and/or one or more existing N-linked glycosylation sites are shifted in a domain selected from the group consisting of Metalloprotease domain, Disintegrin-like Domain, TSP type-1 1 domain, TSP (thrombospondin) type-1 2 domain, TSP type-1 3 domain, TSP type-1 4 domain, TSP type-1 5 domain, TSP type-1 6 domain, TSP type-1 7 domain, TSP type-1 8 domain, Cysteine-rich domain, Spacer domain, CUB (Complement component C1r/C1s, Uegf, and Bone morphogenic protein 1) 1 domain, CUB2 domain, a region between two of said domains and combinations thereof and combinations thereof, more preferably in a domain selected from the group consisting of Metalloprotease domain, Disintegrin-like Domain, TSP type-1 1 domain, TSP type-1 2 domain, TSP type-1 3 domain, TSP type-1 4 domain, TSP type-1 5 domain, TSP type-1 6 domain, TSP type-1 7 domain, TSP type-1 8 domain, Spacer domain, CUB1 domain, CUB2 domain, a region between two of said domains and combinations thereof and combinations thereof. The amino acid residues that for each domain are indicated in the first column in table 5, whereby the numbering refers to the numbering of amino acid residues in the sequence of wildtype ADAMTS13 shown in FIG. 1. "A region between two of said domains" refers to a region between two adjacent domains, preferably between the Metalloprotease Domain and the Disintegrin-like Domain, between the Disintegrin-like Domain and TSP type-1 1 Domain, between the TSP type-1 2 and TSP type-1 3 Domains, between the TSP type-1 3 and TSP type-1 4 Domains, between the TSP type-1 4 and TSP type-1 5

Domains, between the TSP type-1 7 and TSP type-1 8 Domains and between the TSP type-1 8 and CUB1 domain.

In an ADAMTS13 protein variant provided by the invention, said one or more N-linked glycosylation sites are not added to and said one or more existing N-linked glycosylation sites are not shifted to amino acid residues 464-466, 469-471, 476-478, 493-495, 511-513 and 539-541 of said ADAMTS13 protein variant. Preferably, said one or more N-linked glycosylation sites are not added to and said one or more existing N-linked glycosylation sites are not shifted to amino acid residues 440-553 or 464-539 of said ADAMTS13 protein variant. More preferably, said one or more N-linked glycosylation sites are not added to and said one or more existing N-linked glycosylation sites are not shifted in the cysteine-rich domain consisting of amino acid residues 440-556 of ADAMTS13.

In a further preferred embodiment, one or more N-linked glycosylation sites are added or shifted in an ADAMTS13 protein variant according to the invention or used in accordance with the invention as compared to wild-type ADAMTS13 by introducing an N-glycosylation site (NXT or NXS, wherein X is any amino acid except P) in the spacer domain comprising residues S556 to A685 of the ADAMTS13 sequence, as shown in FIG. 1 and/or in any of the amino acid sequences shown in Table 5 or by shifting an N-glycosylation site to any of the amino acid sequences shown in Table 5. In an ADAMTS13 protein variant provided by the invention, said one or more N-linked glycosylation sites are not added to and said one or more existing N-linked glycosylation sites are not shifted to amino acid residues 464-466, 469-471, 476-478, 493-495, 511-513 and 539-541 of said ADAMTS13 protein variant.

In one preferred embodiment, one or more N-linked glycosylation sites are added or shifted in an ADAMTS13 protein variant according to the invention or used in accordance with the invention, the one or more N-linked glycosylation sites are added and/or said one or more existing N-linked glycosylation sites are shifted in the metalloprotease domain, preferably comprising residues L80 to P226, of the ADAMTS13 sequence, as shown in FIG. 1. Said one or more N-linked glycosylation sites in the metalloprotease domain are added or shifted are preferably shifted in the domains indicated with No's 1-9 in Table 5.

In one preferred embodiment, one or more N-linked glycosylation sites are added or shifted in an ADAMTS13 protein variant according to the invention or used in accordance with the invention, the one or more N-linked glycosylation sites are added and/or said one or more existing N-linked glycosylation sites are shifted in the CUB domain, preferably comprising residues C1192 to T1427, of the ADAMTS13 sequence, as shown in FIG. 1. Said one or more N-linked glycosylation sites in the CUB domain are added or shifted are preferably shifted in the domains indicated with No's 59-89 in Table 5.

In one preferred embodiment, one or more N-linked glycosylation sites are added or shifted in an ADAMTS13 protein variant according to the invention or used in accordance with the invention, the one or more N-linked glycosylation sites are added and/or said one or more existing N-linked glycosylation sites are shifted in the TSP1-2-8 domain, preferably comprising residues P682 to P1131, of the ADAMTS13 sequence, as shown in FIG. 1. Said one or more N-linked glycosylation sites in the TSP1-2-8 domain are preferably added or shifted are preferably shifted in the domains indicated with No's 32-56 in Table 5.

In a further preferred embodiment, one or more N-linked glycosylation sites are added or shifted in an ADAMTS13 protein variant according to the invention or used in accordance with the invention, the one or more N-linked glycosylation sites are added and/or said one or more existing N-linked glycosylation sites are shifted in the spacer domain comprising residues S556 to A685 of the ADAMTS13 sequence, as shown in FIG. 1. The spacer domain is 130 amino acids long, and is known to mediate several crucial interactions required for protease activity of ADAMTS13. It has further been shown that a truncated variant of ADAMTS13, comprising amino acids up to and including the spacer domain, i.e. amino acids 1-685, shows proteolytic activity (E.g. Xiao et al. 2011 and De Maeyer et al. 2010). Hence, a preferred ADAMTS13 protein variant according to the invention comprises at least residues 1 to 685 of ADAMTS13, wherein one or more N glycosylation sites are added and/or one or more existing N-glycosylation sites are shifted as compared to wild-type ADAMTS13 and further optional mutations as described herein are introduced. The spacer domain contains surface exposed residues that form the main epitope that is recognized by anti-ADAMTS13 autoantibodies. These residues are also referred to as the exosite-3 domain. This domain contains amino acid residues R568, F592, R660, Y661 and Y665. Alanine mutations of R660, Y661 and Y665 impairs recognition of ADAMTS13 by VWF (Pos et al. 2010; Pos et al. 2011). However, conservative amino acid substitutions of the exosite-3 residues has been shown to result in a gain-of-function variant of ADAMTS13 (Jian et al. 2012). Initially it was believed that this variant is also resistant to autoantibodies, but follow-up experiments have revealed that it is still targeted by patient-derived autoantibodies (Graça et al., 2019). Without wishing to be bound by theory, it is believed that N-glycans attached to asparagine residues in the spacer domain are able to shield the exosite-3 domain, thereby reducing or preventing binding of auto-antibodies to this site.

In a particularly preferred embodiment, in an ADAMTS13 protein variant according to the invention or used in accordance with the invention the one or more N-linked glycosylation sites are added and/or said one or more existing N-linked glycosylation sites are shifted in a spacer domain comprising residues S556 to A685 of the ADAMTS13 sequence, as shown in FIG. 1.

It is further preferred that the one or more N-linked glycosylation sites are added and/or said one or more existing N-linked glycosylation sites are shifted in a part of the spacer domain comprising residues R568 to R670 of the ADAMTS13 sequence, as shown in FIG. 1.

In a further preferred embodiment, the ADAMTS13 protein variant according to the invention or used in accordance with the invention has proteolytic activity against Von Willebrand Factor (VWF) that is at least 10% of the proteolytic activity against VWF of wildtype ADAMTS13 protein. The cut-off for clinically important levels have been set at least 10% (e.g. Hie et al. 2014). As used herein, "proteolytic activity against VWF" refers to the ability of ADAMTS13 or an ADAMTS13 protein variant to cleave VWF. As used herein "x % proteolytic activity against VWF of wildtype ADAMTS13 protein" refers to x % of proteolytic activity against VWF compared to recombinant wild-type ADAMTS13 under the same conditions. I.e. the proteolytic activity against VWF of the ADAMTS13 protein variant according to the invention or used in accordance with the invention is compared with the proteolytic activity against VWF of the recombinant wildtype ADAMTS13 protein under the same conditions, including determined using the same assay, for the same amount of time, using the same concentration of protein, etc. A skilled person is well capable of assessing the proteolytic activity of wildtype ADAMTS13 and an ADAMTS13 protein variant according to the invention or used in accordance with the invention under the same conditions such that this activity can be compared. Proteolytic activity against VWF can, for instance, be determined using an assay as described herein the Examples with FRETS-VWF73 (as described in Kokame et al. 2005) and VWF multimer assay (as described in Graça et al. 2019). Proteolytic activity towards the VWF can for instance be measured using a generally available FRETS-VWF73 substrate (AnaSpec, Fremont, Ca, USA), for instance in accordance with the FRETS-VWF73 substrate assay protocol as described in Example 2.

Preferably, the ADAMTS13 protein variant according to the invention or used in accordance with the invention has a proteolytic activity against VWF that is at least 20% of the proteolytic activity against VWF of wildtype recombinant ADAMTS13 protein, more preferably at least 30%, more preferably at least 40%, more preferably at least 50%, more preferably at least 60% In a particularly preferred embodiment, the ADAMTS13 protein variant according to the invention or used in accordance with the invention has a proteolytic activity against VWF that is at least 70% of the proteolytic activity against VWF of wildtype ADAMTS13 protein. The ADAMTS13 protein variant according to the invention or used in accordance with the invention may also have a proteolytic activity that is higher than that of wildtype ADAMTS13, i.e. have a proteolytic activity against VWF that is more than 100% of the proteolytic activity against VWF of wildtype ADAMTS13 protein.

In a further preferred embodiment, the ADAMTS13 protein variant according to the invention or used in accordance with the invention has a reduced binding by autoantibodies as compared to wildtype ADAMTS13. "Having a reduced binding by autoantibodies" as used herein means that binding of autoantibodies specific for ADAMTS13 show reduced binding to the ADAMTS13 protein variant of the invention or used in accordance with the invention as compared to wildtype ADAMTS13. "Reduced" as used herein preferably means that the binding is reduced by at least 10%, preferably at least 15%, more preferably at least 20%, more preferably at least 25%, more preferably at least 50%, more preferably at least 75%, more preferably at least 80%, more preferably at least 85%, more preferably at least 90%, most preferably at least 95%. Thus, "reduced binding by autoantibodies as compared to wildtype ADAMTS13" preferably means that the binding by autoantibodies, as evidenced e.g. by the reactivity of the ADAMTS13 protein variant according to the invention with iTTP patent sera as detailed herein below, is reduced by at least 10%, more preferably at least 15%, 20%, 25%, 50%, 75%, 80%, 85%, 90% or 95% as compared to binding of wildtype ADAMTS13 protein. Said autoantibodies are preferably but not limited to autoantibodies that bind an epitope located in the exosite-3 domain, more preferably an epitope comprising residues F592, R568, R660, Y661 and/or Y665. Preferably the autoantibodies are autoantibodies present in serum of patients suffering from immune-mediated thrombotic thrombocytopeniarpura (iTTP). Reduction of binding by autoantibodies in serum of iTTP patient serum can for instance be determined by measuring reactivity of the ADAMTS13 protein variant with serum or sera of iTTP patients in an assay as described in the Examples herein. In brief, binding of autoantibodies to ADAMTS13 can be detected by immobilizing ADAMTS13 directly on a surface or indirectly through immobilizing a monoclonal or polyclonal antibody directed towards ADAMTS13 (or a V5-tag or His-tag or any other tag). Subsequently, the immobilized ADAMTS13 is incubated with a patient-derived biological fluid, preferably plasma or serum, allowing for binding of anti-ADAMTS13 immunoglobulins to immobilized ADAMTS13. Bound patient-derived immunoglobulins reactive with ADAMTS13 can subsequently be detected employing conjugated or labelled antibodies that specifically recognize human immunoglobulins. An example of such an assay is presented in Example 3. Other methods to detect antigen-specific antibodies in biological fluids from patients and normal individuals have been extensively described in the literature and can be applied for the detection of antibodies directed towards ADAMTS13 (e.g. Burbelo P D and O'Hanlon T P, 2014) Because autoantibodies in serum of iTTP patient are heterogenous, it is preferred that binding of autoantibodies to the ADAMTS13 protein variant of the invention is determined in serum of multiple iTTP patient, for instance in serum or plasma samples of at least 5 different iTTP patients.

In a further preferred embodiment, the ADAMTS13 protein variant according to the invention or used in accordance with the invention comprises at least an N-linked glycosylation site at an amino acid residue that is contained within the proximity or that contributes to an autoantibody binding site located on ADAMTS13. I.e. the one or more N-linked glycosylation sites are added and/or shifted as compared to wild-type ADAMTS13 are at an amino acid residue that is contained within the proximity or that contributes to an autoantibody binding site located on ADAMTS13. More preferably, the ADAMTS13 protein variant according to the invention or used in accordance with the invention comprises an N-linked glycosylation site at an amino acid residue selected from the group consisting of R568, L591, V604, V605, A606, G607, K608, M609, R636, L637, P638, R639, Y665, L668 and combinations thereof. More preferably, the ADAMTS13 protein variant according to the invention or used in accordance with the invention comprises a N-glycan at an amino acid residue mutation selected from the group consisting of R568N, L591N, V604N, V605N, A606N, G607N, K608N, M609N, R636N, L637N, P638N, R639N, Y665N, L668N and combinations thereof. I.e. the one or more N-linked glycosylation sites are added as compared to wild-type ADAMTS13 by introducing a mutation selected from these groups.

More preferably, the ADAMTS13 protein variant according to the invention or used in accordance with the invention comprises an N-linked glycosylation site at an amino acid position selected from the group consisting of 568, 591, 608, 609, 636, 637, 665, 668 as shown in FIG. 1 and combinations thereof, more preferably at an amino acid position selected from the group consisting of 591, 608, 609, 636, 665, 668 as shown in FIG. 1 and combinations thereof, more preferably at an amino acid position selected from the group consisting of 608, 609, 665 as shown in FIG. 1 and combinations thereof.

In one embodiment, the ADAMTS13 protein variant according to the invention or used in accordance with the invention comprises a mutation selected from the group consisting of 568REY570 to 568NET570 (NGLY1), 591LFT593 to 591NFT593 (NGLY2), 608KMSI611 to 608NMSI611 (NGLY3), 608KMSI611 to 608KNST611 (NGLY4), 636RLPR639 to 636NLSR639 (NGLY5), 636RLPR639 to 636RNAS639 (NGLY6), 665YGNL668 to 665NVTL668 (NGLY7), 667NLTRP671 to 667LNVTA671 (NGLY8) and combinations thereof. I.e. the one or more N-linked glycosylation sites are added and/or shifted as compared to wild-type ADAMTS13 by introducing a mutation selected from this group. The indications between brackets such as "NGLY1", "NGLY2", etc. refer to the variants indicated in tables 1 and 3. The indications "N-glyx" and "NGLYx" are used herein interchangeably, such as "N-gly1" and "NGLY1" or "N-gly2" and "NGLY2", etc. In a further preferred embodiment, the ADAMTS13 protein variant according to the invention or used in accordance with the invention comprises a mutation selected from the group consisting of 591LFT593 to 591NFT593 (NGLY2), 608KMSI611 to 608NMSI611 (NGLY3), 608KMSI611 to 608KNST611 (NGLY4), 665YGNL668 to 665NVTL668 (NGLY7) and 667NLTRP671 to 667LNVTA671 (NGLY8), more preferably comprising a mutation selected from the group consisting of 608KMSI611 to 608NMSI611 (NGLY3), 608KMSI611 to 608KNST611 (NGLY4) and 665YGNL668 to 665NVTL668 (NGLY7), most preferably comprising mutation 608KMSI611 to 608NMSI611 (NGLY3). I.e. the one or more N-linked glycosylation sites are added and/or shifted as compared to wild-type ADAMTS13 by introducing a mutation selected from this group. As demonstrated in the Examples herein, these variants have shown particularly strong reduction in binding by autoantibodies present in serum of iTTP patients but maintain proteolytic activity against VWF.

In addition to the one or more added and/or shifted N-linked glycosylation sites, an ADAMTS13 protein variant according to the invention or used in accordance with the invention may comprise a further mutation at one or more amino acid residues, preferably said mutation or mutations do not introduce an glycosylation site in the protein variant. Said mutation or mutations are is preferably a mutation or mutations in the amino acid sequence of the protein variant as compared to amino acid sequence of wildtype ADAMTS13 protein. For instance, one or more mutations that further reduce binding by autoantibodies to the ADAMTS13 protein variant, one or more mutations that result in an increase in proteolytic activity against VWF, and/or one or more mutations that increase stability of the ADAMTS13 protein variant can be introduced.

The mutation can be a substitution of an amino acid by another amino acid, an insertion of one or more amino acids or a deletion of one or more amino acids. Preferably, such further mutation or mutations are substitutions of one or more amino acids by another amino acids. Said mutation can be introduced throughout the sequence of the protein variant. In one preferred embodiments, one or more mutations, preferably substitutions, are introduced in the sites within the different domains of ADAMTS13 that are targeted by autoantibodies. In a more preferred embodiment, a mutation, preferably substitution, is introduced at one or more amino acid residues in the spacer domain comprising residues S556 to A685 as shown in FIG. 1. More preferably, an ADAMTS13 protein variant according to the invention or used in accordance with the invention comprises a mutation, preferably substitution, at an amino acid residue selected from the group consisting of R568, L591, F592, R636, L637, L668, L591, F592, R636, L637, R660, Y661, Y665. L668 and combinations thereof. For instance, one or more amino acids that are mutated in the known gain of function mutants, i.e. R568, F592, R660, Y661 and Y665, are mutated in an ADAMTS13 protein variant according to the invention, such as R660, Y661 and Y665, or R568, F592, R660 and Y661 or R568, F592, R660, Y661 and Y665.

In one preferred embodiment, an ADAMTS13 protein variant according to the invention or used in accordance with the invention comprises a mutation selected from the group consisting of R568K, R568A, R568N, L591A, F592Y, F592A, F592N, R636A, L637A, R660K, R660A, R660N, Y661F, Y661A, Y661N, Y665F, Y665A, Y665N, L668A and combinations thereof. As shown in the examples herein, and in e.g. Jian et al. 2012, Pos et al. 2010 and Graça et al. 2019, such mutants either preserve or increase proteolytic activity of ADAMTS13.

In one preferred embodiment, an ADAMTS13 protein variant according to the invention or used in accordance with the invention comprises mutations R568A and Y665A.

In one preferred embodiment, an ADAMTS13 protein variant according to the invention or used in accordance with the invention comprises mutations L591A, R636A, L637A, and L668A.

In one preferred embodiment, an ADAMTS13 protein variant according to the invention or used in accordance with the invention comprises mutations R568A and Y665A or mutations L591A, R636A, L637A, and L668A.

In a further preferred embodiment, an ADAMTS13 protein variant according to the invention or used in accordance with the invention comprises mutations R660K, R660A or R660N; Y661F, Y661A or Y661N; and Y665F, Y665A or Y665N.

In a further preferred embodiment, an ADAMTS13 protein variant according to the invention comprises mutations R568K, R568A or R568N; F592Y, F592A or F592N; R660K, R660A or R660N; and Y661F, Y661A or Y661N.

In a further preferred embodiment, an ADAMTS13 protein variant according to the invention or used in accordance with the invention comprises mutations R568K, R568A or R568N; F592Y, F592A or F592N; R660K, R660A or R660N; Y661F, Y661A or Y661N; and Y665F, Y665A or Y665N.

In one preferred embodiment an ADAMTS13 protein variant according to the invention or used in accordance with the invention comprising an N-glycosylation site at amino acid residue 608 of the ADAMTS13 sequence, as shown in FIG. 1, preferably an ADAMTS13 protein variant comprising the sequence 607GNMSI611, further comprises one or more of said further mutations.

The mutations introduced in an ADAMTS13 protein variant according to the invention or used in accordance with the invention, including both mutations that are made to add and/or shift one or more N-linked glycosylation sites and any further mutations as described herein as compared to wild-type ADAMTS13, preferably result in an ADAMTS13 protein variant comprising an amino acid sequence that is at least 90% identical to the sequence of the corresponding amino acid sequence in wildtype ADAMTS13. The term "% sequence identity" is defined herein as the percentage of amino acids in an amino acid sequence that is identical with the amino acids in a reference amino acid sequence or an amino acid sequence of interest, after aligning the sequences and optionally introducing gaps, if necessary, to achieve the maximum percent sequence identity. Methods and computer programs for alignments are well known in the art. The skilled person understands that consecutive amino acid residues in one amino acid sequence are compared to consecutive amino acid residues in another amino acid sequence. Sequence identity is calculated over full sequence of the ADAMTS13 protein variant and the corresponding sequence of wild ADAMTS13. I.e. an ADAMTS13 protein variant consisting of residues 1-685 of ADAMTS13 preferably has an amino acid sequence that is at least 90% identical to the amino acid sequence of residues 1-685 of wildtype ADAMTS13; a full length ADAMTS13 protein variant preferably has an amino acid sequence that is at least 90% identical to the full length amino acid sequence of wildtype ADAMTS13; an ADAMTS13 protein variant consisting of residues 1-900 of ADAMTS13 preferably has an amino acid sequence that is at least 90% identical to the amino acid sequence of residues 1-900 of wildtype ADAMTS13, etc. Said sequence identity is preferably at least 90%, more preferably at least 95%, more preferably at least 96%, more preferably at least 97%, more preferably at least 98%.

The invention further provides an ADAMTS13 protein variant according to the invention or used in accordance with the invention comprising a N-linked glycan at said one or more N-linked glycosylation sites that are added and/or wherein said one or more existing N-linked glycosylation sites that are shifted comprise a N-linked glycan. Said protein variant preferably has proteolytic activity against Von Willebrand Factor (VWF) that is at least 10% of the proteolytic activity against VWF of wildtype ADAMTS13 protein, more preferably at least 20%, more preferably at least 30%, more preferably at least 40%, more preferably at least 50% of the proteolytic activity against VWF of wild-type ADAMTS13 protein. As used herein, the term "N-linked glycan" refers to a carbohydrate moiety that is linked to a protein or protein variant via a nitrogen linkage at an N-glycosylation site. A variety of N-linked glycans exists and the N-linked glycan can be any glycan that can be attached to an N-linked glycosylation site as defined herein. A person skilled in the art is well aware of glycan that can be attached to N-linked glycosylation sites. FIG. 2 shows suitable common and other structures of N-linked glycans. In a preferred embodiment, the N-linked glycan is an N-linked glycan selected from the N-linked glycans shown in FIG. 2. Attachment of N-linked glycans to an ADAMTS13 protein variant as described herein can be achieved by methods known in the art, including recombinantly producing the protein variant in a suitable host cell, that is capable of producing glycoproteins containing N-linked glycans. Suitable host cells include eukaryotic host cells, in particular mammalian cell, such as CHO cells, NS0 cells, SP2/0 cells, PERC.6 cells or HEK293 cells. Alternatively, in vitro modification of the glycosylation patterns is possible.

In another preferred embodiment, an ADAMTS13 protein variant according to the invention or used in accordance with the invention has proteolytic activity against Von Willebrand Factor (VWF) that is at least 10% of the proteolytic activity against VWF of wildtype ADAMTS13 protein. In a further preferred embodiment the variant is a full length ADAMTS13 variant, i.e. having amino acids 1-1427 as shown in FIG. 1. Preferably said ADAMTS13 protein variant comprises a N-linked glycan at said one or more N-linked glycosylation sites that are added and/or said one or more existing N-linked glycosylation sites that are shifted comprise a N-linked glycan and that has proteolytic activity against Von Willebrand Factor (VWF) that is at least 10% of the proteolytic activity against VWF of wildtype ADAMTS13 protein. In a further preferred embodiment, said variant comprises a further mutation at one or more amino acid residues is in the spacer domain comprising residues S556 to A685, more preferably a mutation at an amino acid residue selected from the group consisting of R568, L591, F592, R636, L637, L668, L591, F592, R636, L637, R660, Y661, Y665. L668 and combinations thereof, even more preferably a mutation selected from the group consisting of R568K, R568A, R568N, L591A, F592Y, F592A, F592N, R636A, L637A, R660K, R660A, R660N, Y661F, Y661A, Y661N, Y665F, Y665A, Y665N, L668A and combinations thereof.

In another preferred embodiment, in an ADAMTS13 protein variant according to the invention or used in accordance with the invention, the one or more N-linked glycosylation sites are added as compared to wild-type ADAMTS13 and/or one or more existing N-linked glycosylation sites are shifted as compared to wild-type ADAMTS13 in a spacer domain comprising residues S556 to A685 and the ADAMTS13 protein variant has proteolytic activity against Von Willebrand Factor (VWF) that is at least 10% of the proteolytic activity against VWF of wildtype ADAMTS13 protein. Preferably, said ADAMTS13 protein variant comprises a N-linked glycan at said one or more N-linked glycosylation sites that are added and/or said one or more existing N-linked glycosylation sites that are shifted comprise a N-linked glycan. In a further preferred embodiment the variant is a full length ADAMTS13 variant, i.e. having amino acids 1-1427 as shown in FIG. 1. In a further preferred embodiment, said variant comprises a further mutation at one or more amino acid residues is in the spacer domain comprising residues S556 to A685, more preferably a mutation at an amino acid residue selected from the group consisting of R568, L591, F592, R636, L637, L668, L591, F592, R636, L637, R660, Y661, Y665. L668 and combinations thereof, even more preferably a mutation selected from the group consisting of R568K, R568A, R568N, L591A, F592Y, F592A, F592N, R636A, L637A, R660K, R660A, R660N, Y661F, Y661A, Y661N, Y665F, Y665A, Y665N, L668A and combinations thereof.

In another preferred embodiment, in an ADAMTS13 protein variant according to the invention or used in accordance with the invention, the one or more N-linked glycosylation sites are added as compared to wild-type ADAMTS13 by introducing a mutation selected from the group consisting of 568REY570 to 568NET570 (NGLY1), 591LFT593 to 591NFT593 (NGLY2), 608KMSI611 to 608NMSI611 (NGLY3), 608KMSI611 to 608KNST611 (NGLY4), 636RLPR639 to 636NLSR639 (NGLY5), 636RLPL639 to 636RNAS639 (NGLY6), 665YGNL668 to 665NVTL668 (NGLY7), 667NLTRP671 to 667LNVTA671 (NGLY8) and combinations thereof, more preferably selected from the group consisting of 591LFT593 to 591NFT593 (NGLY2), 608KMSI611 to 608NMSI611 (NGLY3), 608KMSI611 to 608KNST611 (NGLY4), 636RLPR639 to 636NLSR639 (NGLY5).

Preferably, said ADAMTS13 protein variant comprises a N-linked glycan at said one or more N-linked glycosylation sites that are added and/or said one or more existing N-linked glycosylation sites that are shifted comprise a N-linked glycan. In a further preferred embodiment the variant is a full length ADAMTS13 variant, i.e. having amino acids 1-1427 as shown in FIG. 1. In a further preferred embodiment, said variant comprises a further mutation at one or more amino acid residues is in the spacer domain comprising residues S556 to A685, more preferably a mutation at an amino acid residue selected from the group consisting of R568, L591, F592, R636, L637, L668, L591, F592, R636, L637, R660, Y661, Y665. L668 and combinations thereof, even more preferably a mutation selected from the group consisting of R568K, R568A, R568N, L591A, F592Y, F592A, F592N, R636A, L637A, R660K, R660A, R660N, Y661F, Y661A, Y661N, Y665F, Y665A, Y665N, L668A and combinations thereof.

In another preferred embodiment, in an ADAMTS13 protein variant according to the invention or used in accordance with the invention, the one or more N-linked glycosylation sites are added or shifted as compared to wild-type ADAMTS13 by introducing an N-glycosylation site (NXT or NXS, wherein X is any amino acid except P) in any of the amino acid sequences shown in Table 5 or by shifting an N-glycosylation site to any of the amino acid sequences shown in Table 5, with the proviso that said one or more N-linked glycosylation sites are not added to and said one or more existing N-linked glycosylation sites are not shifted to amino acid residues 464-466, 469-471, 476-478, 493-495, 511-513 and 539-541 of said ADAMTS13 protein variant. Preferably, said ADAMTS13 protein variant comprises a N-linked glycan at said one or more N-linked glycosylation sites that are added and/or said one or more existing N-linked glycosylation sites that are shifted comprise a N-linked glycan. In a further preferred embodiment the variant is a full length ADAMTS13 variant, i.e. having amino acids 1-1427 as shown in FIG. 1. In a further preferred embodiment, said variant comprises a further mutation in one or more amino acid residues in ADAMTS13. In a further preferred embodiment, said variant comprises a further mutation at one or more amino acid residues is in the spacer domain comprising residues S556 to A685, more preferably a mutation at an amino acid residue selected from the group consisting of R568, L591, F592, R636, L637, L668, L591, F592, R636, L637, R660, Y661, Y665. L668 and combinations thereof, even more preferably a mutation selected from the group consisting of R568K, R568A, R568N, L591A, F592Y, F592A, F592N, R636A, L637A, R660K, R660A, R660N, Y661F, Y661A, Y661N, Y665F, Y665A, Y665N, L668A and combinations thereof.

In another preferred embodiment, in an ADAMTS13 protein variant according to the invention or used in accordance with the invention, an N-linked glycosylation site is added as compared to wild-type ADAMTS13 by introducing a mutation selected from the group consisting of 591LFT593 to 591NFT593 (NGLY2), 608KMSI611 to 608NMSI611 (NGLY3), 608KMSI611 to 608KNST611 (NGLY4) and 636RLPR639 to 636NLSR639 (NGLY5), and said ADAMTS13 protein variant comprises a N-linked glycan at said N-linked glycosylation site that is added, said variant further comprises a mutation selected from the group consisting of R568K, R568A, R568N, L591A, F592Y, F592A, F592N, R636A, L637A, R660K, R660A, R660N, Y661F, Y661A, Y661N, Y665F, Y665A, Y665N, L668A and combinations thereof, preferably further comprising mutations R568K, R568A or R568N; F592Y, F592A or F592N; R660K, R660A or R660N; Y661F, Y661A or Y661N; and Y665F, Y665A or Y665N.

Particularly preferred ADAMTS13 protein variants are the variants as described herein indicated as NGLY1, NGLY2, NGLY3, NGLY4, NGLY5, NGLY6, NGLY7, NGLY8, NGLY3+NGLY7, NGLY+NGLY8, NGLY3+L591A/R636A/L637A/L668A, NGLY3 plus R568A/Y665A and NGLY3+R568A/Y665A+L591A/R636A/L637A/L668A, more preferably variants as described herein indicated as NGLY2, NGLY3, NGLY4, NGLY5, NGLY7, NGLY8, NGLY3+NGLY7, NGLY+NGLY8, NGLY3+L591A/R636A/L637A/L668A and NGLY3 plus R568A/Y665A.

The invention also provides a nucleic acid encoding an ADAMTS13 protein variant according to the invention. Further provided is a nucleic acid construct comprising a nucleic acid sequence encoding an ADAMTS13 protein variant according to the invention. The nucleic acid sequence and construct according to the invention both are useful for therapeutic application as well as in the preparation of the ADAMTS13 protein variants according to the invention.

The term "nucleic acid", as used herein, refers to DNA and RNA including mRNA or cDNA, as well as synthetic variants thereof. The nucleic acid can be a recombinant or synthetic nucleic acid.

The nucleic acid construct according to the invention is preferably present in a vector, such as an expression vector. The expression vector can be a viral or non-viral vector. Non-limiting examples of suitable expression vectors include retroviral, adenoviral, adeno-associated, herpes simplex and lentiviral vectors, non-viral vectors and engineered vectors. Non-viral expression vectors include nude DNA, and nucleic acids packaged into synthetic or engineered compositions such as liposomes, polymers, nanoparticles and molecular conjugates. Methods for the generation of such non-viral expression vectors are well known in the art. The expression vector preferably comprises a strong promoter/enhancer, such as the CMV or SV40 promoter, an optimal translation initiation sequence, such as a ribosomal binding site and start codon, and/or a transcription termination sequence, including a poly (A) signal when the protein is expressed in eukaryotic cells. A person skilled in the art will understand that the expression vector to be used is dependent on the host cell that is used for expression of an ADAMTS13 protein variant according to the invention, preferably a N-linked glycan containing protein variant. An expression vector is preferably suited for expression of a nucleic acid molecule of the invention in eukaryotic host cells, more preferably mammalian host cells, more preferably in CHO cells, NS0 cells, SP2/0 cells, PERC.6 cells and/or HEK293 cells.

As an alternative, a nucleic acid sequence used in accordance with the invention may be provided to a subject by gene editing technology, including CRISPR/Cas, zinc-finger nucleases, and transcription activator-like effector nucleases-TALEN, in order to insert the receptor transgenes into specific loci with or without an exogenous promoter. Preferred genomic loci include the AAVS1 locus and the PD-1 locus, as is known to a skilled person.

Also provided is a pharmaceutical composition comprising an ADAMTS13 protein variant according to the invention and one or more pharmaceutically acceptable carriers, adjuvants, excipients and/or diluents. By "pharmaceutically acceptable" it is meant that the auxiliary, carrier, diluent or excipient must be compatible with the other ingredients of the formulation and not deleterious, e.g. toxic, to the recipient thereof. In general, any pharmaceutically suitable additive which does not interfere with the function of the active compounds can be used. A pharmaceutical composition according to the invention is preferably suitable for human use.

Examples of suitable carriers comprise a solution, lactose, starch, cellulose derivatives and the like, or mixtures thereof. In a preferred embodiment said suitable carrier is a solution, for example saline. For making dosage units, e.g. tablets, the use of conventional additives such as fillers, colorants, polymeric binders and the like, is contemplated. Examples of excipients which can be incorporated in tablets, capsules and the like are the following: a binder such as gum tragacanth, acacia, corn starch or gelatin; an excipient such as microcrystalline cellulose; a disintegrating agent such as corn starch, pregelatinized starch, alginic acid and the like; a lubricant such as magnesium stearate; a sweetening agent such as sucrose, lactose or saccharin.

A pharmaceutical composition according to the invention is preferably suitable for or adapted for parenteral administration. Said administration is preferably intravenous, intra-arterial, subcutaneous, and/or intramuscular administration. Administration may either be by injection or by infusion. Compositions for injectable, e.g. intravenous, administration may for example be solutions comprising the ADAMTS13 protein variant of the invention in sterile aqueous solution such as an isotonic aqueous buffer, an oily solution, a dispersion, emulsion and/or suspension, preferably an aqueous solution. The injectable, e.g. intravenous, compositions may include for instance solubilizing agents, stabilizing agents and/or a local anesthetic to ease the pain at the site of the injection or infusion.

It is within the ability of a person skilled in the art to determine an appropriate dosing regimen, i.e. dosage and administration interval, depending on the condition to be treated and the desired effect (e.g. short-lived effect or long term treatment). The exact dose and regimen of these compounds and compositions thereof will further be dependent on the biological activity of the ADAMTS13 protein variant, the age, weight and sex of the subject, the needs of the individual subject to whom the medicament is administered, the degree of affliction or need and the judgment of the medical practitioner. An example of a suitable dose is for instance a dose ranging from 0.1 mg to 15 gram, such as from 1 to 10 gram, of the ADAMTS13 protein variant of the invention.

In an embodiment of the invention, a pharmaceutical kit or kit of parts is provided comprising one or more containers filled with one or more pharmaceutical compositions of the invention. Associated with such container(s) can be various written materials such as instructions for use, or a notice in the form prescribed by a governmental agency regulating the manufacture, use or sale of pharmaceuticals products, which notice reflects approval by the agency of manufacture, use, or sale for human or veterinary administration. Preferably, a pharmaceutical kit or kit of parts comprises instructions for use.

ADAMTS13 protein variants used in accordance with the invention can be administered to a subject by a variety of routes. For example, the protein variant can be administered by any suitable parenteral or nonparenteral route, including, for example, topically (e.g., cream, ointment, eyedrops), or nasally (e.g., solution, suspension). Parenteral administration can include, for example, intraarticular, intramuscular, intravenous, intraventricular, intraarterial, intrathecal, subcutaneous, or intraperitoneal administration. Intravenous and subcutaneous administration may be most advantageous. Further, the protein variant may be administered to a subject in hospital via infusion or via injection by a healthcare professional.

An ADAMTS13 protein variant according to the invention can be prepared by methods generally known and available in the art. For instance, the person skilled in the art will understand how to generate a DNA sequence that encodes an amino acid sequence of a protein variant according to the invention and how to prepare and isolate a nucleic acid molecule with said DNA sequence using generally known recombinant DNA techniques. The sequence of the nucleic acid molecule can be codon-optimized for expression in a suitable host cell.

Nucleic acid molecules are preferably introduced in an expression vector as described herein above using recombinant DNA techniques known by the person skilled in the art. Expression vectors in the context of the invention direct the expression of an protein variant according to the invention in a suitable host cell as described herein. As an alternative, a nucleic acid molecule may be inserted in the genome of a host cell, using suitable gene editing technology as described herein. Said insertion preferably is at a locus or within a region that ensures expression of a nucleic acid molecule of the invention in the host cell.

The term "host cell" as used herein refers to any cell capable of expressing a heterologous protein, polypeptide or peptide. In a preferred embodiment, the host cell is capable of attaching N-linked glycans to protein, peptide or poly-peptide. In a further preferred embodiment, the host cell is an eukaryotic host cell, more preferably a mammalian cell, more preferably selected from the group consisting of CHO cells, NS0 cells, SP2/0 cells, PERC.6 cells and HEK293 cells. Suitable transfection techniques are known in the art, e.g., from Green & Sambrook., 2012. "Molecular Cloning: A Laboratory Manual", 4th Edition, CSHL Press; Cold Spring Harbor Protocols, www.cshprotocols.cshlp.org).

The ADAMTS13 protein variants described herein have VWF proteolytic activity and are therefore particularly useful for treating disorders characterized by aberrant VWF activity and/or VWF processing and/or a thrombotic dis-eases.

The invention therefore provides an ADAMTS13 protein variant comprising residues 1 to 685 of ADAMTS13 and wherein one or more N-linked glycosylation sites are added as compared to wild-type ADAMTS13 and/or one or more existing N-linked glycosylation sites are shifted as compared to wild-type ADAMTS13 or nucleic acid construct encoding such ADAMTS13 protein variant for use in therapy. Also provided is such ADAMTS13 protein variant or nucleic acid construct encoding such ADAMTS13 protein variant for use as an antithrombotic agent. As used herein, the term "anti-thrombotic agent" refers to a compound that prevents the formation of blood clots, reduces or slows down the forma-tion of blood clots and/or counteracts existing blood clots.

The invention also provides an ADAMTS13 protein vari-ant comprising residues 1 to 685 of ADAMTS13 and wherein one or more N-linked glycosylation sites are added as compared to wild-type ADAMTS13 and/or one or more existing N-linked glycosylation sites are shifted as compared to wild-type ADAMTS130r nucleic acid construct encoding such ADAMTS13 protein variant for use in the treatment of a disorder characterized by aberrant Von Willebrand Factor (VWF) activity and/or VWF processing. Also provided is a method for the treatment of a disorder characterized by aberrant Von Willebrand Factor (VWF) activity and/or VWF processing comprising administering to a subject in need thereof an ADAMTS13 protein variant comprising residues 1 to 685 of ADAMTS13 and wherein one or more N-linked glycosylation sites are added as compared to wild-type ADAMTS13 and/or one or more existing N-linked glyco-sylation sites are shifted as compared to wild-type ADAMTS13 or nucleic acid construct encoding such ADAMTS13 protein variant. As used herein, the term "von Willebrand Factor" or "VWF" refers to a plasma glycopro-tein that mediates adhesion and aggregation of platelets. VWF is synthesized by endothelial cells and megakaryo-cytes as long multimers with a molecular weight of up to more than 20,000 kDa. The majority of circulating VWF is synthesized by endothelial cells. Most of the secreted VWF consists of ultra-large VWF (ULVWF) multimers that are prothrombotic. As described herein above, prothrombotic activity of VWF is regulated during normal hemostasis through limited cleavage by ADAMTS13. As used herein "aberrant VWF activity" means that activity VWF activity, in particular prothrombotic activity of VWF, deviates from VWF activity in healthy subjects, preferably is increased as compared to VWF activity in healthy subjects. The deviation or increase is in particular such that it results in adverse health effect, i.e. in a disease or disorder. "Aberrant VWF processing" as used herein means that processing of VWF, in particular cleavage of VWF, in particular of VWF mul-timer, deviates from VWF processing in healthy subject, in particular is decreased as compared to VWF processing in healthy subjects. As will be appreciated by the skilled person, the ADAMTS13 protein variants can be used to correct ADAMTS13 deficiency in a subject. Hence, in principle any disorder in which VWF activity or processing is aberrant can be treated with an ADAMTS13 protein variant as described herein. The term "ADAMTS13 defi-ciency", as used herein, refers to ADAMTS13 not exhibiting its role in hemostasis (controlling VWF multimer size through cleavage) as in healthy subjects. This could be caused by low ADAMTS13 protein levels, an excess of its substrate VWF or the presence of autoantibodies against ADAMTS13. Preferably, ADAMTS13 deficiency resulting from the presence of autoantibodies in a subject.

In a preferred embodiment, provided is an ADAMTS13 protein variant comprising residues 1 to 685 of ADAMTS13 and wherein one or more N-linked glycosylation sites are added as compared to wild-type ADAMTS13 and/or one or more existing N-linked glycosylation sites are shifted as compared to wild-type ADAMTS13 or nucleic acid con-struct encoding such ADATMS13 protein variant for use in the treatment of a thrombotic disease, both acquired or congenital thrombotic disease. Also provided is a method for the treatment of a thrombotic disease, both acquired or congenital thrombotic disease, comprising administering to a subject in need thereof an ADAMTS13 protein variant comprising residues 1 to 685 of ADAMTS13 and wherein one or more N-linked glycosylation sites are added as compared to wild-type ADAMTS13 and/or one or more existing N-linked glycosylation sites are shifted as compared to wild-type ADAMTS13 or nucleic acid construct encoding such ADAMTS13 protein variant. Because such ADAMTS13 protein variant is capable of cleaving and thereby reducing activity of VWF, prothrombotic activity of VWF is reduced.

In a further preferred embodiment, the disorder is a thrombotic microangiopathy. More preferably, the disorder is selected from the group consisting of thrombotic throm-bocytopeniarpura (TTP), hemolytic-uremic syndrome (HUS), ischemic stroke, systemic thrombosis, COVID19, antiphospholipid syndrome, pre-eclampsia/HELLP syn-drome, sepsis and sickle cell disease.

ADAMTS13 is known to have systemic antithrombotic effects, as described for instance by Chauhan et al. (2006), which showed spontaneous thrombus formation in Adamts13$^{-/-}$ mice and conclude that ADAMTS13 has a powerful natural antithrombotic activity and recombinant ADAMTS13 could be used as an antithrombotic agent. An ADAMTS13 protein variant as described herein can thus be advantageously used in the treatment of systemic thrombo-sis.

Thrombotic microangiopathy includes thrombotic throm-bocytopeniaurpura (TTP). TTP includes both immune-me-diated TTP (iTTP) and congenital TTP (cTTP). In a pre-ferred embodiment, the thrombotic microangiopathy is TTP. In a further preferred embodiment the TTP is iTTP. Both in iTTP and congenital TTP ADAMTS13 levels are strongly reduced. Recombinant wildtype ADAMTS13 is currently being tested in clinical trial for treatment of both cTTP and iTTP (Scully et al, 2019; Clinical Trial Identifier:

NCT03922308). An ADAMTS13 protein variant according to the invention can thus be used for treatment of both iTTP and congenital TTP. Autoantibodies present in patients with iTTP limit the effectiveness of treatment with wild-type ADAMTS13 as present in human plasma or as produced as a wildtype recombinant ADAMTS13 protein in eukaryotic expression systems. Autoantibody-resistant ADAMTS13 variants allow for immediately restoring functional ADAMTS13 levels thereby alleviating the severe thrombotic complications observed in patients with iTTP as well as other thrombotic disorders.

HUS is characterized by hemolytic anemia, thrombocytopenia, systemic thrombotic microangiopathy (TMA) and renal failure. Partial ADAMTS13 deficiency can be found in HUS patients. An ADAMTS13 protein variant as described herein can thus be advantageously used in the treatment of HUS, in particular HUS associated with partial ADAMTS13 deficiency.

Thrombosis is the predominant underlying mechanism of acute ischemic stroke (AIS). Several studies have found that ADAMTS13 levels are significantly decreased in patient suffering from ischemic stroke, with the lowest levels of ADAMTS13 found in patients suffering from acute stroke. As detailed in a review by Chen et al. (2019), the available evidence indicates that ADAMTS13 is closely related to the occurrence, development, and prognosis of ischemic stroke, protecting the brain from ischemia-reperfusion injury. The VWF: ADAMTS13 ratio has a strong correlation with the risk of stroke. The activity and levels of ADAMTS13 have a good predictive value for the occurrence and prognosis of ischemic stroke. In addition, animal studies on ADAMTS13 in the treatment of AIS have made remarkable progress: injections of recombinant ADAMTS13 to wild type mice 7 days after stroke onset increased the formation of neovasculature and repair of blood vessels, and significantly improved the 14-day prognosis after stroke. It is concluded that ADAMTS13 is expected to become a new therapeutic agent for ischemic stroke. An ADAMTS13 protein variant as described herein can thus be advantageously used in the treatment of ischemic stroke.

Sepsis is a disease in which coagulopathy is observed, and thrombotic microangiopathy may be a component thereof. Thrombotic microangiopathy in sepsis is associated with low levels of ADAMTS-13. Ramsi and Al Ali (2018) describe a case of thrombocytopenia-associated multiple-organ failure (TAMOF) associated with sepsis that had dramatic improvement with plasma exchange through which ADAMTS13 activity was restored, and the pathological process and organ failures were halted. An ADAMTS13 protein variant as described herein can thus be advantageously used in the treatment of sepsis, in particular thrombotic microangiopathy in subjects suffering from sepsis.

In Sickle cell disease a low ADAMTS13/VWF ratio has been found and ADAMTS13 activity was lower in patients who developed acute chest syndrome, suggesting quantitative decrease in ADAMTS-13 levels and that administration of recombinant ADAMTS-13 may have a beneficial effect (Sins et al. 2017). This indicates that ADAMTS13 protein variants according to the invention can thus be advantageously used in the treatment of sickle cell disease.

Thrombosis affecting the pulmonary and systemic vasculature is common during severe COVID19 (coronavirus disease 2019), caused by infection with severe acute respiratory syndrome-coronavirus-2 (SARS-COV-2), Turecek et al. (2020) showed that markedly increased plasma VWF levels were accompanied by a partial reduction in the VWF regulatory protease ADAMTS13. Incubation of plasma samples from patients with severe COVID-19 with recombinant ADAMTS13 (rADAMTS13) substantially reduced the abnormally high VWF activity, reduced overall multimer size and depleted UHMW VWF multimers in a time and concentration dependent manner and it is suggested that rADAMTS13 may have a therapeutic role in helping restore haemostatic balance in COVID-19 patients. This indicates that ADAMTS13 protein variants according to the invention can thus be advantageously used in the treatment of COVID-19 and/or SARS-COV-2 infection.

Antiphospholipid syndrome and pre-eclampsia (PEcl) have been associated with reduced ADAMTS13 levels and with higher ADAMTS13 antibodies, and lower ADAMTS13 activity and activity: antigen ratios (Bitsatze et al. 2021). Further, thrombocytopenia and microangiopathic hemolytic anemia (TMA) are seen in HELLP syndrome. Additionally, Austin et al. (2008) show that ADAMTS13 autoantibodies and ADAMTS13 dysfunction can occur in antiphospholipid syndrome. This indicates that ADAMTS13 protein variants according to the invention can thus be advantageously used in the treatment of antiphospholipid syndrome and pre-eclampsia/HELLP syndrome, in particular in antiphospholipid syndrome and pre-eclampsia/HELLP syndrome associated with ADAMTS13 dysfunction.

The term "subject" as used herein refers to the recipient of an ADAMTS13 protein variant or encoding nucleic acid according to the invention and encompasses humans and animals. The subject is preferably a mammal, more preferably a human.

The term "therapeutically effective amount," as used herein, refers to an amount of an ADAMTS13 protein variant being administered sufficient to relieve one or more of the symptoms of the disease or condition being treated to some extent. This can be a reduction or alleviation of symptoms, reduction or alleviation of causes of the disease or condition or any other desired therapeutic effect.

As used herein, the term "treatment" refers to inhibiting the disorder, i.e., halting or reducing its development or at least one clinical symptom of the disease or condition, and/or to relieving symptoms of the disease or condition.

Features may be described herein as part of the same or separate aspects or embodiments of the present invention for the purpose of clarity and a concise description. It will be appreciated by the skilled person that the scope of the invention may include embodiments having combinations of all or some of the features described herein as part of the same or separate embodiments.

The invention will be explained in more detail in the following, non-limiting examples.

BRIEF DESCRIPTION OF THE DRAWINGS

FIG. 1: Amino acid sequence of ADAMTS13 (SEQ ID NO: 1); UniProt accession number Q76LX8.

FIG. 2: N-linked glycans identified on ADAMTS13 (derived from Verbij et al. 2016). ■: GlcNAc, ●: mannose; ○: galactose; ▲: fucose; ♦: sialic acid.

FIG. 7: Activity of ADAMTS13 variants in the presence of TTP patient sera, measured with FRETS-VWF73.

FIG. 8: Proteolytic activity of WT- and NGLY3 ADAMTS13 under flow conditions. The length of VWF strings were manually measured between both timepoints and the reduction in their length was calculated. The results are expressed as relative activity compared to the WT-ADAMTS13 (left), and based on the reduction of VWF string size for each variant (right). Both WT-ADAMTS13 and the NGLY3 variants demonstrated to be active in this assay.

EXAMPLES

Example 1. Design of N-Glycan Variants of ADAMTS13

Figure 3:
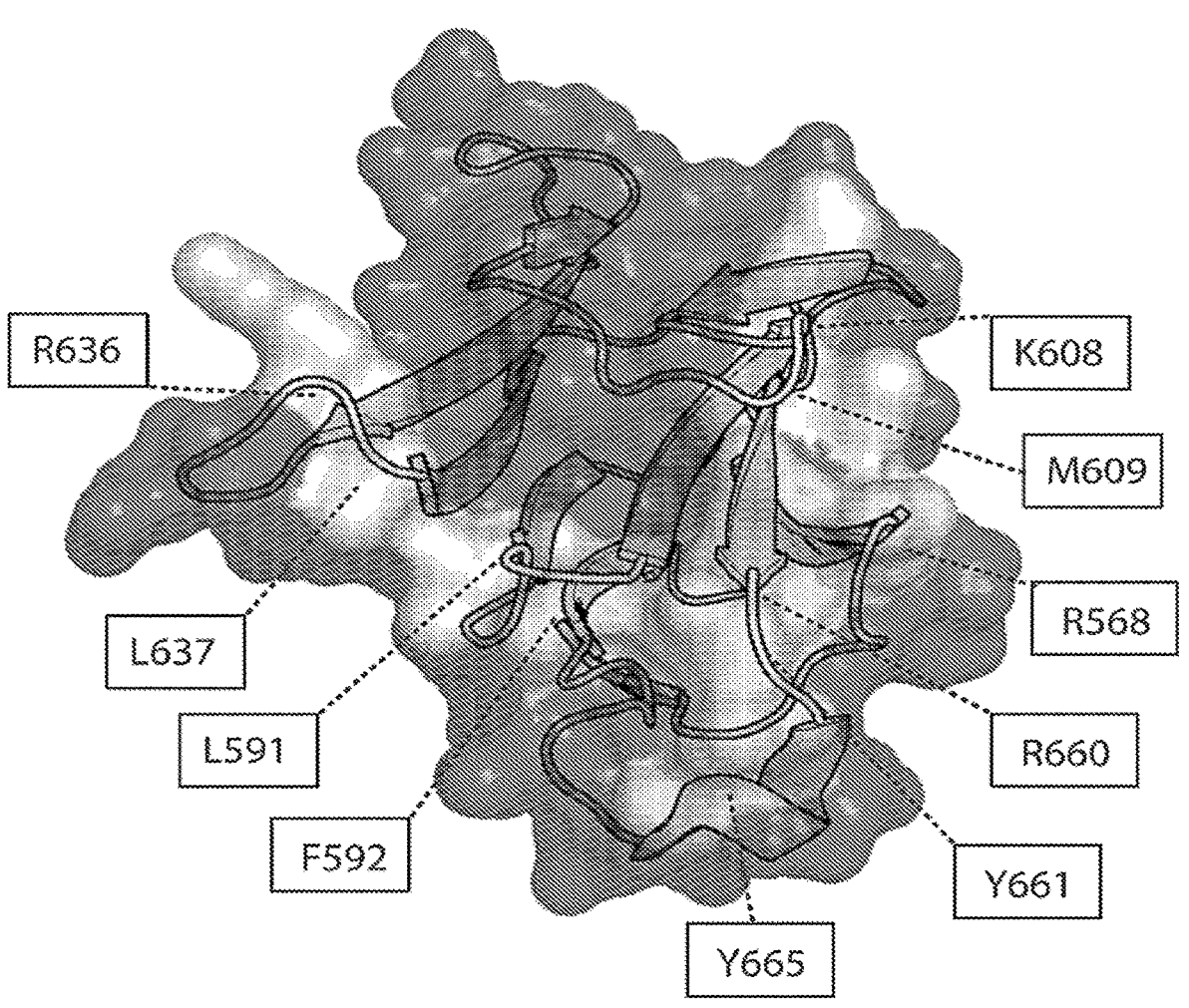
FIG. 3: ADAMTS13 model showing residues ADAMTS13 exosite-3 comprising R568, F592, R660, Y661 and Y665 within the spacer domain. Residues L591, R636, L637, K608 and M609 surrounding exosite-3 are also displayed.

Autoantibodies that develop in patients with immune TTP (iTTP) are frequently directed towards an immunodominant region in the spacer domain that is composed of residues R568, F592, R660, Y661 and Y665 (see FIG. 3). In a previous study we created a large number of ADAMTS13 variants that included conservative (Y↔F), semi-conservative (Y/F↔L), non-conservative (Y/F→N; no additions of putative N-glycosylation sites) or alanine (Y/F/R→A) substitutions. A previous gain-of-function variant in which F568, R592, R660, Y661 and Y665 were all replaced for conservative residues was also included (RFRYY→KYKFF) (Graça et al., 2019). The resulting panel of variants was tested for reactivity with autoantibodies present in sera of 18 patients with iTTP. Our results indicated that non-conservative or alanine mutations within the spacer domain resulted in a strongly reduced binding of auto-antibodies whereas binding of autoantibodies to ADAMTS13 spacer domain variants containing semi-conservative and conservative mutations was less strongly affected when compared to non-conservative variants (Graça et al., 2019). Residues R568, F592, R660, Y661 and Y665 are crucial for optimal VWF cleaving activity of ADAMTS13 (Pos et al., 2010; Jian et al., 2012). In line with these data we observed that non-conservative or alanine substitutions resulted in loss of activity whereas conservative and semi-conservative substitutions tended to retain more residual or even normal activity. Overall our results suggested a "trade-off" between resistance towards patient autoantibody binding and proteolytic activity. The results of this study indicated that design of autoantibody resistant ADAMTS13 variants which retained significant proteolytic activity is not feasible through systematic replacement of combinations of residues R568, F592, R660, Y661 and Y665, in particular for residues F592, R660 and Y661 (Graça et al., 2019). Therefore, we took an innovative approach in which residues R568, F592, R660, Y661 and Y665 itself were not altered thereby allowing for the binding of unfolded VWF A2 domain to this region in the ADAMTS13 spacer domain (Pos et al., 2010; Crawley et al., 2011; Ercig et al., 2018a). Based on the currently available data we constructed a model which shows binding of residues E1660-R1668 of the unfolded A2 domain to ADAMTS13 exosite-3 comprising R568, F592, R660, Y661 and Y665 within the spacer domain (FIG. 3). Based on this model, we selected a number of residues just within or around ADAMTS13 exosite-3 within the spacer domain for insertion of an additional N-glycan by selectively introducing consensus-sites for N-glycan attachment (NXS or NXT) within the spacer domain. Based on the model presented in FIG. 3, N-glycans were inserted at amino acid positions 568 (NGLY1), 591 (NGLY2), 608 (NGLY3), 609 (NGLY4), 636 (NGLY5) and 637 (NGLY6). The amino acid substitutions needed for introduction of N-glycans at these sites are listed in Table 1.

TABLE 1

List of generated full-length ADAMTS13 NGLY variants in Example 1.

| Mutation | Original sequence | Mutated sequence |
|---|---|---|
| NGLY1 | 567AREYV571 | 567ANETV571 |
| NGLY2 | 590PLFTH594 | 590PNFTH594 |
| NGLY3 | 607GKMSI611 | 607GNMSI611 |
| NGLY4 | 608KMSIS612 | 608KNSTS612 |
| NGLY5 | 635DRLPR639 | 635DNLSR639 |
| NGLY6 | 636RLPRL640 | 636RNASL640 |

Example 2: Expression and Functional Characterization of N-Glycan Variants

The N-glycan variants described in Table 1 were expressed in CHO cells employing QMCF technology (described in European Patent EP1851319B1; www.icosagen.com). Full-length wild-type ADAMTS13 (1427 amino acids), and a full-length ADAMTS13 variant which contained the substitutions R568A/F592A/R660A/Y661A/Y665A (designated ADAMTS13-AAAAA) were used as controls. A wild-type ADAMTS13 variant truncated beyond the spacer domain (amino acid sequence 1-685) was used as an additional control; this ADAMTS13 variant was designated MDTCS. An additional MDCTS variant in which substitutions R568A/F592A/R660/Y661A/Y665A were present was also used as a control for our studies; this variant was designated MDTCS-AAAAA. These constructs have been described previously and were all cloned into the plasmid expression vector pQMCF3 (Icosagen Cell Factory OU) (Graça et al., 2019). All cDNAs contained a carboxy-terminal V5 epitope which was followed by a 6xHis-tag (Graça et al., 2019).

NGLY variants were constructed as follows: synthetic DNA fragments encoding residues M509 to W688 (540 bp) in which NGLY substitutions were introduced were designed and ordered by Genewiz (Leipzig, Germany). The synthetic fragments were flanked by an XmaI site at the 5' end and a HindIII at the 3' end of the fragment. The XmaI site is native to the wild-type ADAMTS13 cDNA sequence. The HindIII site was introduced by silent mutations in the nucleotide sequences encoding Q684 (CAG to CAA) and A685 (GCC to GCT) resulting in an overall change from 5'-CAGGCCT-3' to 5'-CAAGCTT-3'. The plasmid pUC57_mut1.1 was custom-designed and obtained through Genewiz (Leipzig, Germany). In this plasmid was cloned a larger ADAMTS13 fragment coding from F494 to C908 (1245 bp), and flanked by the native sites PagI at 5' and Esp3I at 3'. In pUC57_mut1.1, an additional artificial XhoI site was introduced by silent mutation of the nucleotide sequence encoding L621 (CTG to CTC), resulting in an overall change from 5'-CTGGAG-3' to 5'CTCGAG-3' (Graça et al, 2019). The synthetic DNA fragments (540 bp) encoding NGLY1 to NGLY6 were first used to replace the corresponding XmaI-HindIII fragment in pUC57_mut1.1, where they were embedded individually to create pUC57_NGLY1-6. Then, the larger 1245 bp fragment flanked by native PagI-Esp3I in each pUC57_NGLY was used to replace the respective wild-type fragment of ADAMTS13 in pQMCF3. The resulting pQMCF3_ADAMTS13-NGLY1-6 variants were subsequently expressed in CHO cells as described previously (Graça et al., 2019). Supernatants were collected 10-12 days post transfection, cleared by centrifugation and stored at −30° C. until further use.

ADAMTS13 levels present in culture supernatant were quantified by ELISA using a previously established assay (Alwan et al., 2017; Graça et al., 2019). ADAMTS13 antigen levels measured for the different proteins ranged approximately from 1.0-2.5 µg/ml (see Table 2) and were similar to levels of wild-type ADAMTS13 in culture supernatants. In agreement with previous findings MDCTS and MDCTS-AAAAA were expressed at higher levels (Table 2). These data show that ADAMTS13-NGLY1-6 are secreted from transfected CHO cells at levels similar to that of wild type ADAMTS13.

TABLE 2

Antigen levels of ADAMTS13 NGLY variants and controls

| Variant | Antigen level (µg/mL) |
|---|---|
| Full-length ADAMTS13 wild-type | 1.44 |
| Full-length AAAAA | 1.22 |
| MDTCS (wild-type) | 12.94 |
| MDTCS-AAAAA | 10.78 |
| NGLY1 | 1.83 |
| NGLY2 | 2.36 |
| NGLY3 | 2.33 |
| NGLY4 | 2.21 |

TABLE 2-continued

| Antigen levels of ADAMTS13 NGLY variants and controls | |
| --- | --- |
| Variant | Antigen level (μg/mL) |
| NGLY5 | 2.31 |
| NGLY6 | 1.88 |

Figure 4:
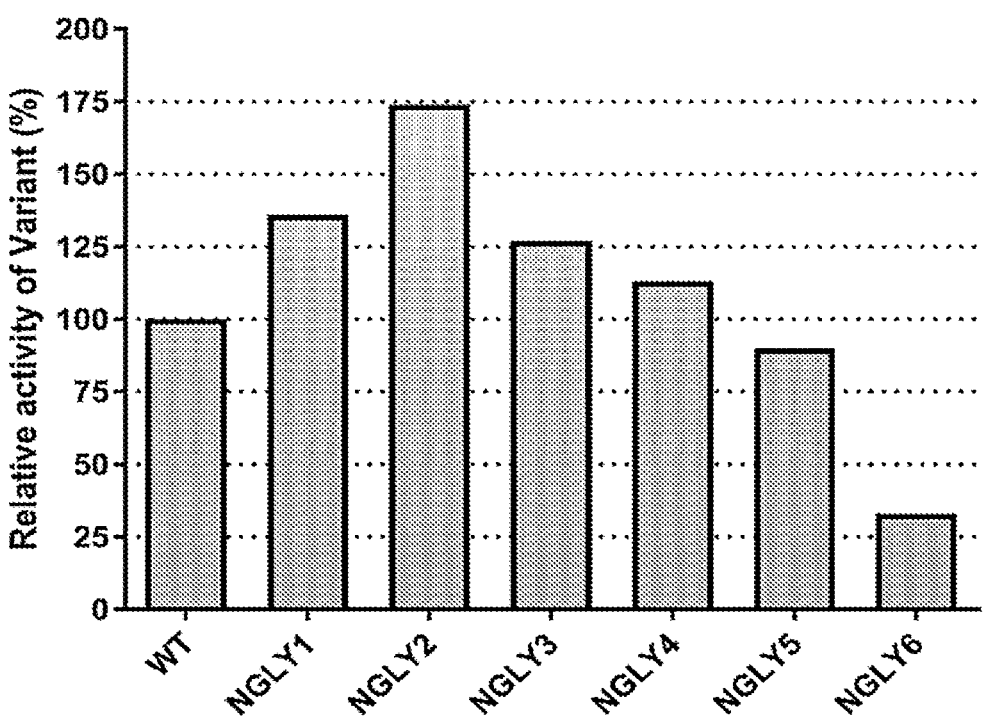
FIG. 4: Activity of ADAMTS13 variants relative to wild-type ADAMTS13 as determined by FRETS-VWF73 assay.

We also tested the ability of the different ADAMTS13-NGLY variants to process a small fluorogenic substrate designated FRETS-VWF73, the minimum peptide representative of the A2 domain of VWF harboring the Tyr1605-Met1606 scissile bond and to be used for ADAMTS13 activity assessment (Kokame et al., 2005). Diluted culture supernatants containing the ADAMTS13 NGLY variants at a concentration of 1.05 nM (0.2 μg/ml) were used for these assays. ADAMTS13 was first diluted in an activity buffer composed of 20 mM HEPES, 20 mM Bis-Tris, 20 mM Tris-HCl, 25 mM CaCl$_2$) (pH 6.0) supplemented with 0.005% Tween20 to 2.10 nM in 100 μl volume. Then, the FRETS-VWF73 substrate was added (100 μl, 4 M), diluting further ADAMTS13 to 1.05 nM, and the reaction started. In parallel, a calibration curve was done in a similar manner using the wild-type ADAMTS13 diluted in a concentration range of 0.13125-2.10 nM. The activity-levels were interpolated and compared to that of wild-type ADAMTS13 with final concentration of 1.05 nM, which was set at 100%. The results of this analysis are shown in FIG. 4. NGLY6 showed a reduced activity when compared to wild-type ADAMTS13. The activity of NGLY5 was slightly reduced when compared to wild type ADAMTS13. The ability of NGLY1, 2, 3 and 4 was similar or higher when compared to wild-type ADAMTS13 (FIG. 4).

Figure 5:
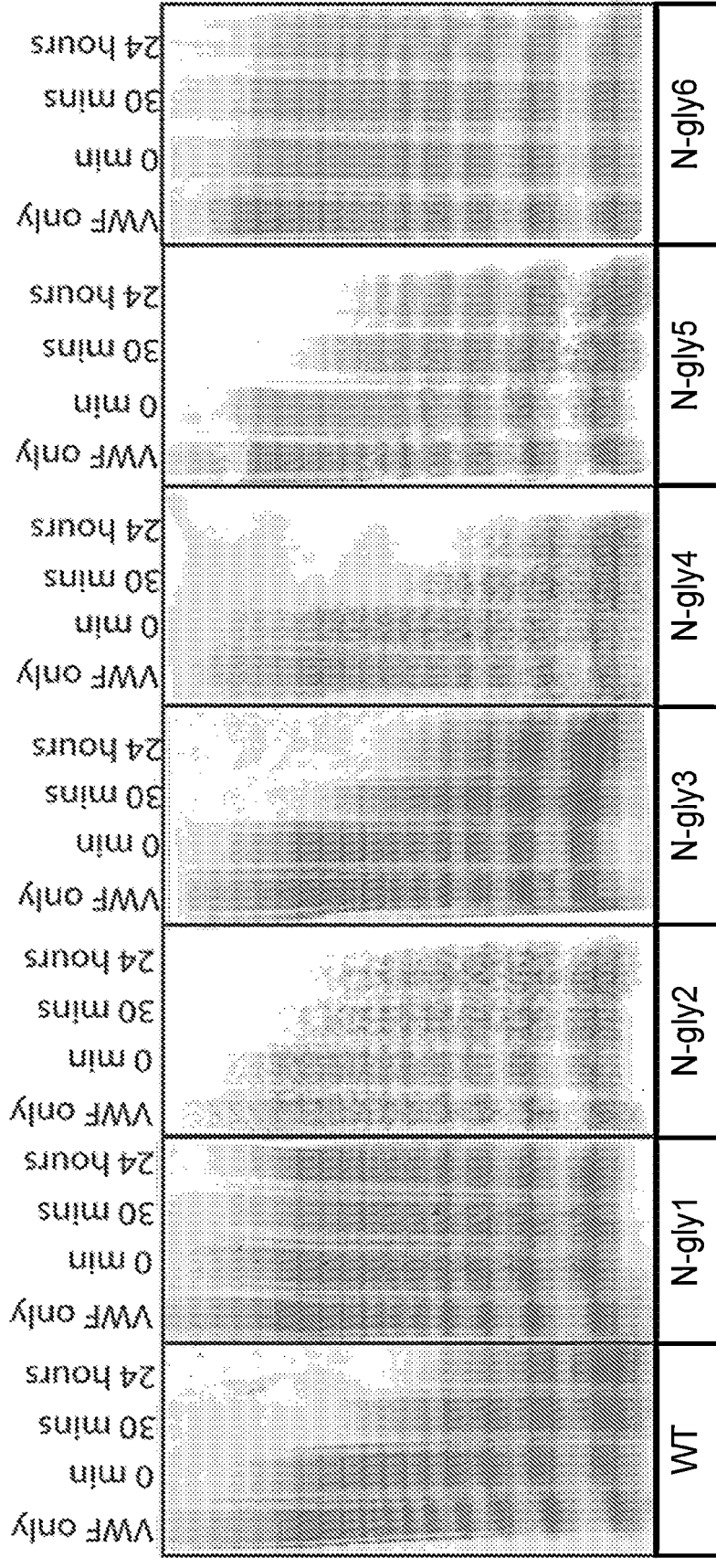
FIG. 5: Capacity to cleave VWF of wildtype ADAMTS13 and ADAMTS13 variants in a VWF multimer assay.

Subsequently, we tested the activity of the ADAMTS13-NGLY1-6 variants in a more physiological VWF multimer assay essentially as described previously (Graça et al., 2019). ADAMTS13 variants were incubated for 30 mins at 37° C. at a concentration of 0.2 μg in an activation buffer composed of 20 mM Bis-Tris, 20 mM Tris-HCl, 20 mM HEPES, 25 mM CaCl2 (pH 7.5), 0.005% Tween20 and supplemented with 2% Bovine Serum Albumin fraction V (Merck) (ADAMTS13=3.8 nM). In parallel, human recombinant VWF produced in HEK293 cells was incubated with 3 M urea for 30 min at 37° C. at a final concentration of 80 nM. Denatured recombinant VWF multimers were then added to the ADAMTS13 containing mixture at a 1 to 1 ratio (final ADAMTS13=1.9 nM; final VWF=40 nM). Capacity to cleave VWF in these conditions is visualized by the disappearance of High-Molecular Weight (HMW) multimers from the top of the gel, and accumulation of cleavage products seen through higher intensity of bands in the lower part of the gel, as well as the appearance of satellite bands. Samples were collected and quenched with 4× loading buffer (composition: urea 9.6 M, 4% SDS m/v, Tris-base 0.035 M, EDTA 25 mM, Bromophenol blue 7.5 pM, no pH adjustment) at 0 and 30 minutes and 24 hours to assess the ability of the different ADAMTS13-NGLY1-6 variants to process VWF. Results are shown in FIG. 5. Under these experimental conditions, a reduced VWF processing activity was observed for NGLY2 and NGLY5. The VWF processing activity of NGLY3 and NGLY4 was similar to that of the wild-type ADAMTS13 (FIG. 5).

Overall, these results indicate that NGLY2, 3, 4 and 5 show activity in both the multimer and FRETSVWF73 assay.

Figure 6:
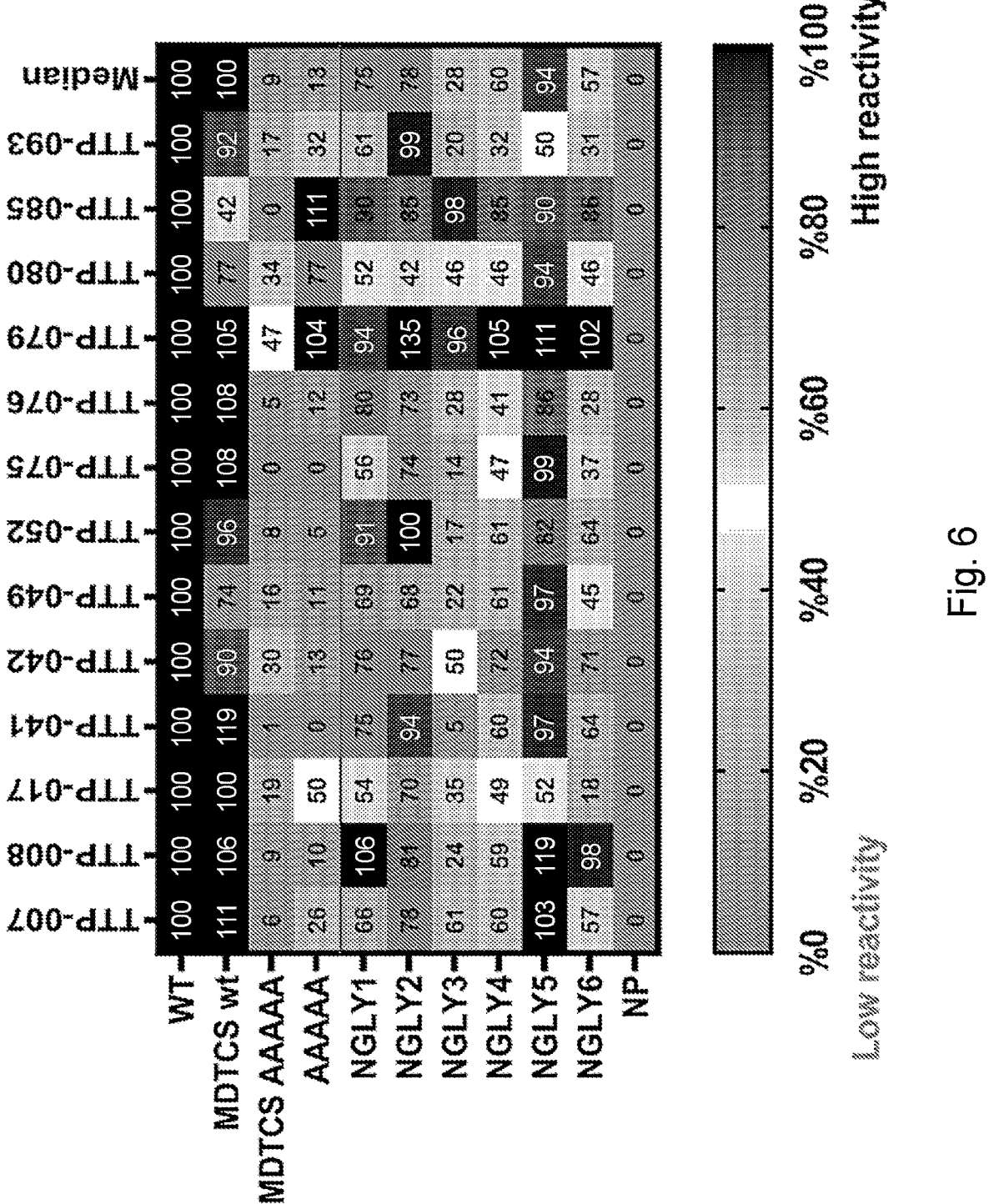
FIG. 6: Heatmap showing reactivity of wildtype ADATMS13 and ADAMTS13 variants against TTP patients autoantibodies.

Example 3. Binding of Pathogenic Autoantibodies from TTP Patients to ADAMTS13 NGLY Variants Binding of autoantibodies present in a collection of samples from patients with iTTP. A previously developed ELISA was used to assess the binding of a panel of 13 samples of iTTP patients (kindly provided by Prof. Paul Coppo and Prof. Agnès Veyradier (Centre de Reference des Microangiopathies Thrombotiques—CNR-MAT, AP-HP, Paris France). The protocol for the assessment of patient-derived autoantibodies was published previously (Graça et al., 2019). Plates were coated overnight with 100 μl monoclonal antibody 3H9 (kindly provided by Prof Vanhoorelbeke, KU Leuven, Belgium) at a concentration of 1 μg/ml. Plates were then blocked with phosphate buffered saline (PBS) supplemented with 2% BSA. Plates were then incubated with 1.05 nmol/well of ADAMTS13 (200 ng/well for full-length ADAMTS13 and 78.75 ng/well for MDTCS variants). Subsequently, 100 μl of the different dilutions of each patient sample were tested for reactivity with each ADAMTS13 variant. Next, 100 μl of a pool of monoclonal antibodies directed towards human IgG1, IgG2, IgG3 and IgG4, each conjugated with horseradish peroxidase and diluted 1:10 000 (Sanquin, The Netherlands) was incubated to assess the binding of patient IgG to the immobilized ADAMTS13 variants, essentially as described previously (Graça et al., 2019). Dilutions used for the different patient samples ranged from 30× to 400× depending on the amount and affinity of anti-ADAMTS13 antibodies present in the patient sample. Dilutions of patient samples were adjusted to meet an optimal target optical density at 450 nm (using the 540 nm as a reference) of 1.6. To correct for potential inter-assay variation, a dilution curve of human monoclonal anti-ADAMTS13 antibody II-1 was included in all experiments as outlined previously for data interpolation (Graça et al., 2019). Reactivity of autoantibodies in each patient sample with the ADAMTS13 NGLY-variants was compared to that of the observed reactivity with wild-type ADAMTS13. Binding of patient autoantibodies was expressed as a percentage of the binding of patient autoantibodies to wild-type ADAMTS13. The results of this analysis are presented in FIG. 6. Reactivity of autoantibodies present in patient samples were expressed as a heatmap with reference to reactivity with wild-type ADAMTS13 which was set at 100%. We also determined the reactivity of the different patient samples with the truncated MDTCS variants. For 3 out of 13 samples (TTP-049, TTP-080 and TTP-085) lower signals were observed compared to wild type ADAMTS13. These data indicate that antibodies directed towards the proximal TSP2-8 and CUB1/2 domain are also present in these samples. A strongly reduced reactivity with ADAMTS13-AAAAA was observed as indicated by the green color code. Autoantibodies present in 10 out of 13 patient samples did not bind to ADAMTS13-AAAAA. Residual binding to ADAMTS13-AAAAA was still observed for TTP-049, TTP-080 and TTP-085. Reactivity of autoantibodies in patient samples towards MDTCS-AAAAA is strongly reduced for 9 out of 13 patients. In 4 patient samples (TTP-017, TTP-042, TTP-079 and TTP-080) residual binding to MDTCS was still observed (FIG. 6; lane MDTCS AAAAA). Overall, these findings indicate that, in the majority of patient samples included in this study, autoantibodies target residues of an immunodominant epitope composed of R568, F592, R660, Y661 and Y665 within the spacer domain. We subsequently addressed the reactivity of autoantibodies present in our panel of patient antibodies with ADAMTS13 NGLY1-6 (FIG. 6). A slight reduction in binding was observed for NGLY1, NGLY2 and NGLY5. A more pronounced reduction in binding was observed for NGLY4 and NGLY6. Interestingly, binding of autoantibodies was strongly reduced for NGLY3 in 11 out of 13 patients. Autoantibodies present in patient samples TTP-079 and TTP-085 still reacted strongly with NLGY3; this is most likely due to the presence of autoantibodies binding outside the spacer domain of ADAMTS13. The lack of reactivity of the majority of patient-derived autoantibodies with NGLY3 indicates that introduction of an N-linked glycan at amino acid position 608 abolishes binding of autoantibodies to the immunodominant B cell epitope in the spacer domain of ADAMTS13.

Example 4: N-Glycan Variants of ADAMTS13 Retain Activity in the Presence of Pathogenic Autoantibodies from Patients with iTTP In Example 2 we showed that NGLY2, NGLY3, NGLY4 and NGLY5 were capable of proteolytic processing of VWF multimers as well as the small peptide substrate FRETS-VWF73. In Example 3 we showed that NGLY3 was poorly recognized by pathogenic autoantibodies present in samples of patients with iTTP. This prompted us to assess whether NGLY3 was still capable of processing FRETS-VWF73 in the presence of plasma samples from patients with iTTP. In order to test this we selected two patient samples based on the data presented in FIG. 7: sample TTP-008, which revealed limited reactivity with NGLY3; and sample TTP-085, which still revealed 98% reactivity with NGLY3 (likely due to autoantibodies towards the carboxy-terminal TSP2-8 and/or CUB1/2 domains of ADAMTS13). To test whether NGLY3 retains activity in the presence of these autoantibodies we assessed activity using the FRETS-VWF73 assay as described in Example 2, and before addition of the FRETS-VWF73 substrate, the ADAMTS13 variants (2.10 nM) were each incubated in the presence of 10 µl of patient sample or PBS for 30 mins at 37° C. The final volume was 210 µl of which 10 µl belonged to the added patient plasma or PBS (for control). Activity-levels of wild-type ADAMTS13 1.05 nM incubated in the absence of patient sample was set at 100%. Results of these experiments are depicted in FIG. 7. Incubation of wild-type ADAMTS13 with sample TTP-008 resulted in ~50% reduction of activity. Incubation of wild-type ADAMTS13 with sample TTP-085 resulted in a ~75% reduction in activity. These results show that autoantibodies present in sample TTP-008 and TTP-085 can inhibit the processing activity of ADAMTS13. Next we assessed whether these samples could also inhibit the activity of the NGLY3 variant. Incubation with both TTP-008 and TTP-085 resulted in a decline in activity from 125% to ~75% for both (FIG. 7).

We further analyzed the ability of NGLY3 to process VWF in different flow or shear rate assays. First we assessed the ability of NGLY3 to process VWF strings under flow on the surface of endothelial cells. Endothelial cells were grown in Ibidi p-Slide VI channels coated in 1% gelatin prior to seeding. HUVEC's (Promocell, passage 3) were seeded 50.000 cells per channel. Channel medium was refreshed twice per day with EGM-18 medium (Promocell) with Supplement Mix (2% v/v) (Promocell) and penicillin/streptomycin (1% v/v) (Sigma). Measurements were made at the fourth day of confluency. The flow experiments were performed using a flow rate of 2 mL/min, which corresponds to a shear stress of approximately 2.5 dynes/cm2. Before measurements, cells were starved using M199 medium (Gibco) supplemented with 0.2% BSA for 5 minutes. Sub-sequently, cells were stimulated with 100 pM histamine in M199 medium supplemented with 0.2% BSA for 10 minutes. Next, the VWF strings were stained using anti-VWF polyclonal antibody (DAKO) labeled with AlexaFluor-488, at a dilution 1:2000 for 5 minutes. The ADAMTS13 variants were diluted to a final concentration of 0.1 µg/mL in M199 medium supplemented with 0.2% BSA. ADAMTS13 containing medium was flown over the cells for 10 minutes, during which 3 separate positions were imaged at 10 seconds intervals using a Zeiss Axio Observer Z1 microscope. The first and last image of each position were analyzed with ImageJ. The length of each VWF string was measured manually, and the difference between the total length before and after ADAMTS13 incubation was used to determine the activity of the protein. For the control, we used the medium which was in contact with ExpiCHO cells not producing any ADAMTS13 (FIG. 8).

We also determined the ability of NGLY3 to process VWF multimers under turbulent flow employing a so-called vortex assay (Zhang et al., 2007). Incubation of 40 nM VWF with 1.0 µg/ml recADAMTS13 under turbulent flow of 3000 rpm for 30 minutes in a reaction buffer composed of 25 mM $CaCl_2$); 20 mM Bis-Tris; 20 mM HEPES; 20 mM Tris-HCl; Tween20 0.005% v/v; pH 7.5 (final volume of reaction=200 µL) resulted in loss of the high molecular weight multimers from the sample (FIG. 9A: Lane 3, 13). Addition of 50 mM EDTA prevented the cleavage of the high molecular weight multimers by wild type ADAMTS13 (FIG. 9A; Lane 2, 128). We subsequently tested the ability of NGLY3 to process VWF multimers under turbulent flow using this vortex-based assay. Similar to wild type ADAMTS13 NGLY3 was capable of efficiently processing VWF multimers under turbulent flow (FIG. 9A: Lane 15). Upon addition of 50 mM EDTA processing of VWF multimers by NGLY3 was impaired similarly to wild type ADAMTS13 (FIG. 9A: Lane 14). Overall these results show that the capacity of NGLY3 to cleave VWF substrates under different conditions is identical to that of wild type ADAMTS13.

These results show that the NGLY3 variant retains significant proteolytic activity in the presence of autoantibodies directed towards ADAMTS13.

Figure 10:
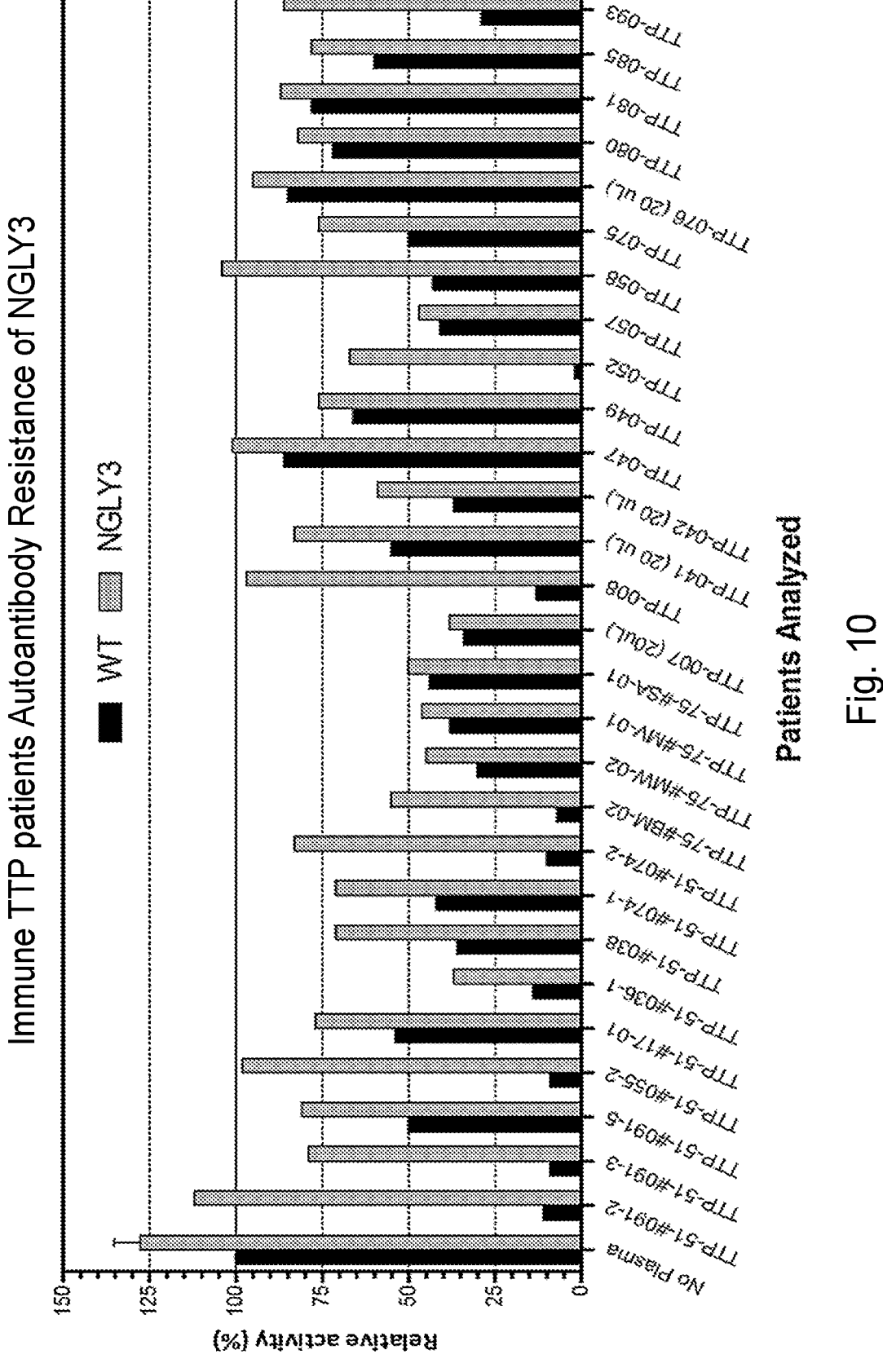
FIG. 10: Relative activity of NGLY3 variant to wild type ADAMTS13 (WT) as measured with FRETS-VWF73 as a substrate in the presence of 10 μl of patient sera or plasma. For four patients (TTP-007, TTP-041, TTP-042 and TTP-076) a condition where 20 μl was added was also evaluated. The activity obtained for wild type ADAMTS13 in the absence of patient sera or plasma was set at 100%. Black bars show the reactivity of wild type ADAMTS13 in the presence of different patient plasma's and sera; grey bars show the activity of the NGLY3 variant in the presence of patient plasma's and sera.

Next we tested the NGLY3 variant against an extended panel of 28 patient's plasmas (FIG. 10). Overall the NGLY3 variant was more active in 18 out of 28 patient samples analyzed. In a limited number of patient samples containing low titer inhibitors the NGLY3 appeared to be slightly more active when compared to wild type ADAMTS13. In 8 patient samples the level of inhibition observed for NGLY3 was similar to that observed for wild type ADAMTS13. In 2 of these patient samples, there was a small but apparently significant difference favoring the NGLY3. Importantly, the NGLY3 variant was always more or equally effective when compared to wild type ADAMTS13.

Figure 11:
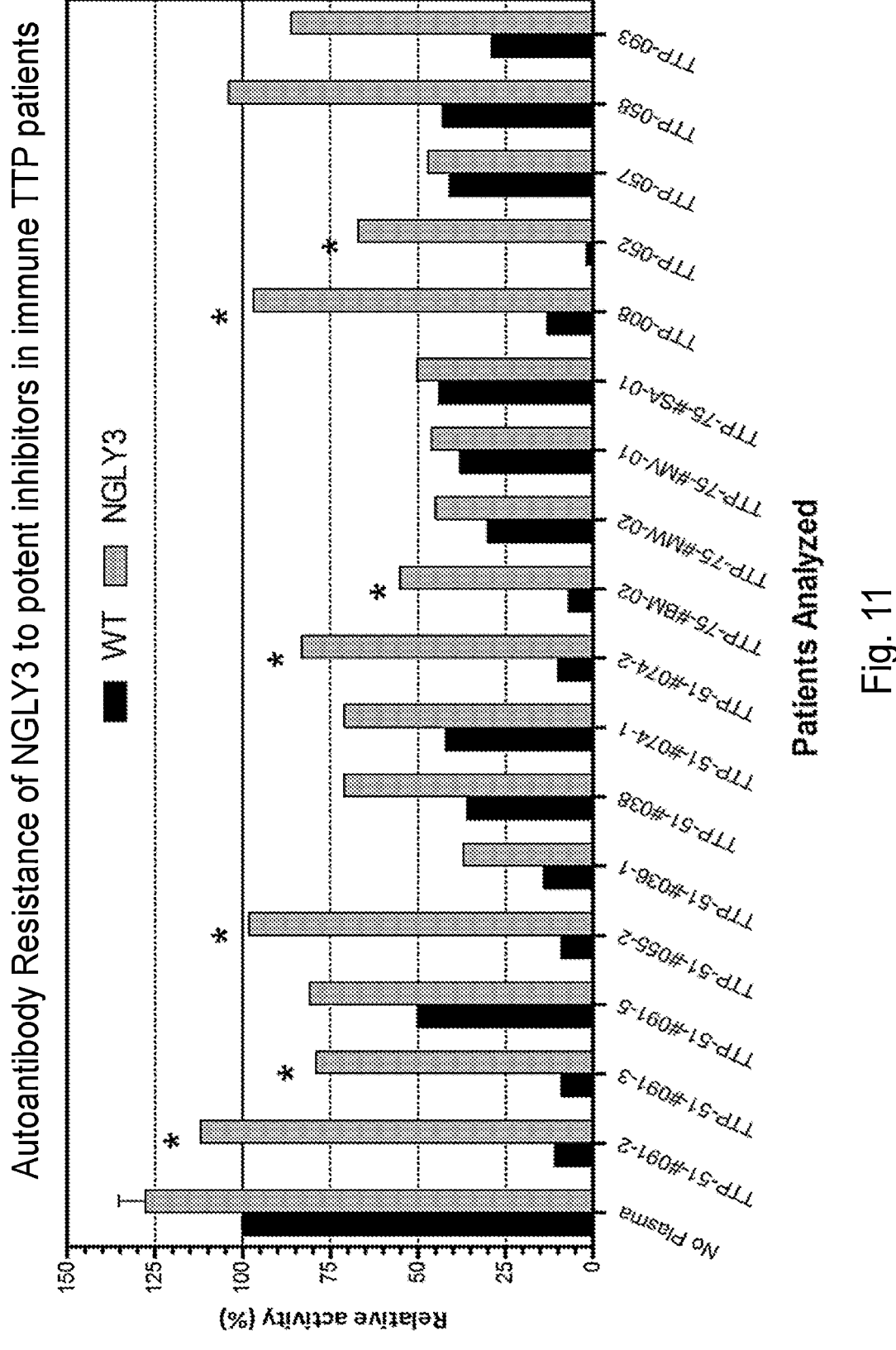
FIG. 11: Autoantibody resistance observed for NGLY3 in high titer inhibitor patients. A subset of patient sera and plasmas inhibiting wild type ADAMTS13 for at least 50% was selected for this Figure. Relative activity of NGLY3 variant to wild type ADAMTS13 (WT) as measured with FRETS-VWF73 as a substrate in the presence of 10 μl of patient sera or plasma is depicted. The activity obtained for wild type ADAMTS13 in the absence of patient sera or plasma was set at 100%. Black bars show the reactivity of wild type ADAMTS13 in the presence of different patient plasma's and sera; grey bars show the activity of the NGLY3 variant in the presence of patient plasma's and sera. Asterisks indicate patient samples for which NGLY3 was at least 5 times more active when compared to wild type ADAMTS13.

We performed a subset-analysis of plasma samples containing high titer inhibitors. High titer inhibitors were defined as the level of inhibitors that gave rise to at least 50% inhibition of the wild type ADAMTS13 (FIG. 11). In 13 out of 17 patients selected the NGLY3 variant was superior when compared to wild type ADAMTS13. In 4 patients the NGLY3 variant was similarly effective when compared to wild type ADAMTS13. Remarkably, in 7 out of 17 patients the NGLY3 variant appears to be more than 5 times efficient when compared to wild type ADAMTS13 (FIG. 11; samples indicated by an asterisk).

These observations suggest that therapeutic administration of a "glycan-shielded" ADAMTS13 variant may comprise a more efficient treatment option for treatment of patients with iTTP when compared to the administration of a wild-type ADAMTS13, either in a recombinant form or as plasma-derived ADAMTS13 in either purified form or as being administered through plasma-exchange.

Example 5: Autoantibody-Resistance of an Extended Panel of N-Glycan Variants As evident from the heatmap shown in FIG. 6, in Example 3 NGLY3 reacts less with patient's autoantibodies. Additionally, as we show in FIG. 7 and Example 4, NGLY3 retains proteolytic activity in the presence of autoantibodies. In the current example we present additional NGLY-variants in which the natural N-glycan inserted at N667 is shifted towards Y665 (giving rise to NGLY7) or L668 (giving rise to NGLY8). Combinations of one or more N-glycan variants may be more efficient. Therefore we designed combinations of NGLY3 and NGLY7 and combinations of NGLY3 and NGLY8 (see Table 3). These variants are constructed in a similar fashion as outlined in Example 1.

N-glycan shielded ADAMTS13 variant containing at least one newly introduced or shifted N-glycan can also be combined with individual amino acid substitutions that diminish binding of pathogenic autoantibodies. Therefore, we are aiming to make additional combinations of NGLY3 with alanine mutations (mostly outside exosite-3), and other NGLY modifications within the vicinity of exosite-3 (Table 3). Due to lack of other potential N-glycosylation sequons within this region, we are seeking the strategy of shifting the natural existing N-glycans in the spacer domain of ADAMTS13 1-2 residues in either direction (N- or C-terminus), namely the glycan present at N667.

TABLE 3

ADAMTS13 NGLY3 variants with additional mutations

| Mutation | Original sequence | Mutated sequence |
|---|---|---|
| NGLY3 | 607GKMSI611 | 607GNMSI611 |
| NGLY7 (glycan shift from N667 to Y665) | 664EYGNLT669 | 664ENVTLT669 |
| NGLY8 Glycan shift from N667 to L668) | 667NLTRP671 | 667LNVTA671 |
| NGLY3 + NGLY7 | 607GKMSI611/ 664EYGNLT669 | 607GNMSI611/ 664ENVTLT669 |
| NGLY3 + NGLY8 | 607GKMSI611/ 667NLTRP671 | 607GNMSI611/ 667LNVTA671 |
| NGLY3 plus L591A/R636A/L637A/ L668A | 607GKMSI611 plus L591, R636, L637, L668 | 607GNMSI611 plus 591A, 636A, 637A, 668A |
| NGLY3 + R568A/Y665A | 607GKMSI611 plus R568, Y665 | 607GNMSI611 plus 568A, 665A |
| NGLY3 + R568A/ Y665A + L591A/R636A/ L637A/L668A | 607GKMSI611 R568, L591, R636, L637, Y665, L668 | 607GNMSI611 plus 568A, 591A, 636A, 637A, 665A, 668A |

These variants are designed as outlined in Example 1. Synthetic DNA fragments encoding residues M509 to W688 (540 bp) in which the novel NGLY variants were introduced were designed and ordered by Genewiz (Leipzig, Germany). The synthetic fragments were flanked by an XmaI site at the 5' end and a HindIII site at the 3' end of the fragment. The synthetic DNA's were first cloned into the XmaI-HindIII site of plasmid pUC57_mut1.1 (see example I), embedded in a larger fragment flanked by PagI-Esp3I. This larger fragment was then used to replace the corresponding fragment in wild type ADAMTS13 as present in pcDNA3.1AD-AMTS13.

The resulting NGLY-variants were expressed in Expi-CHO cells according to the instructions of the manufacturer (Thermo Fisher Scientific). Supernatants were harvested after 4 days post transfection, cleared by centrifugation, supplemented with 10 mM benzamidine and stored at −30° C. until further use. ADAMTS13 levels present in culture supernatants were quantified by ELISA using a previously established assay (Alwan et al., 2017; Graça et al., 2019). ADAMTS13 antigen levels ranged from 1.43 to 5.27 μg/ml (see table 4).

Subsequently we measured the activity of the novel NGLY variants employing the FRETS-VWF73 fluorogenic substrate (Table 4). NGLY7 was 125% active when compared to the wild-type, NGLY8 was 75% active when compared to wild-type ADAMTS13; NGLY3 plus NGLY7 was 125% active when compared to the wild type; NGLY3 plus NGLY8 was 75% active when compared to wild type ADAMTS13. R568A/Y665A was 120% active when compared to wild type; L591A/R636A/L637A/L668A was 90% active when compared to wild type. NGLY3 plus R568A/Y665A was 120% active when compared to wild type, NGLY3 plus L591A/R636A/L637A/L668A was 95% active when compared to wild type ADAMTS13, NGLY3 plus R568A/Y665A plus L591A/R636A/L637A/L668A was 40% active when compared to wild type ADAMTS13.

Overall these results show that combinations of NGLY3 and NGLY7, NGLY3 and NGLY8 as well as NGLY7 and NGLY8 retain the ability to convert the FRETS-VWF73 substrate. Combinations of NGLY3 with R568A/Y665A and/or L591A/R636A/L637A/L668A also retain their ability to convert the FRETS-VWF73 substrate.

Figure 9A:
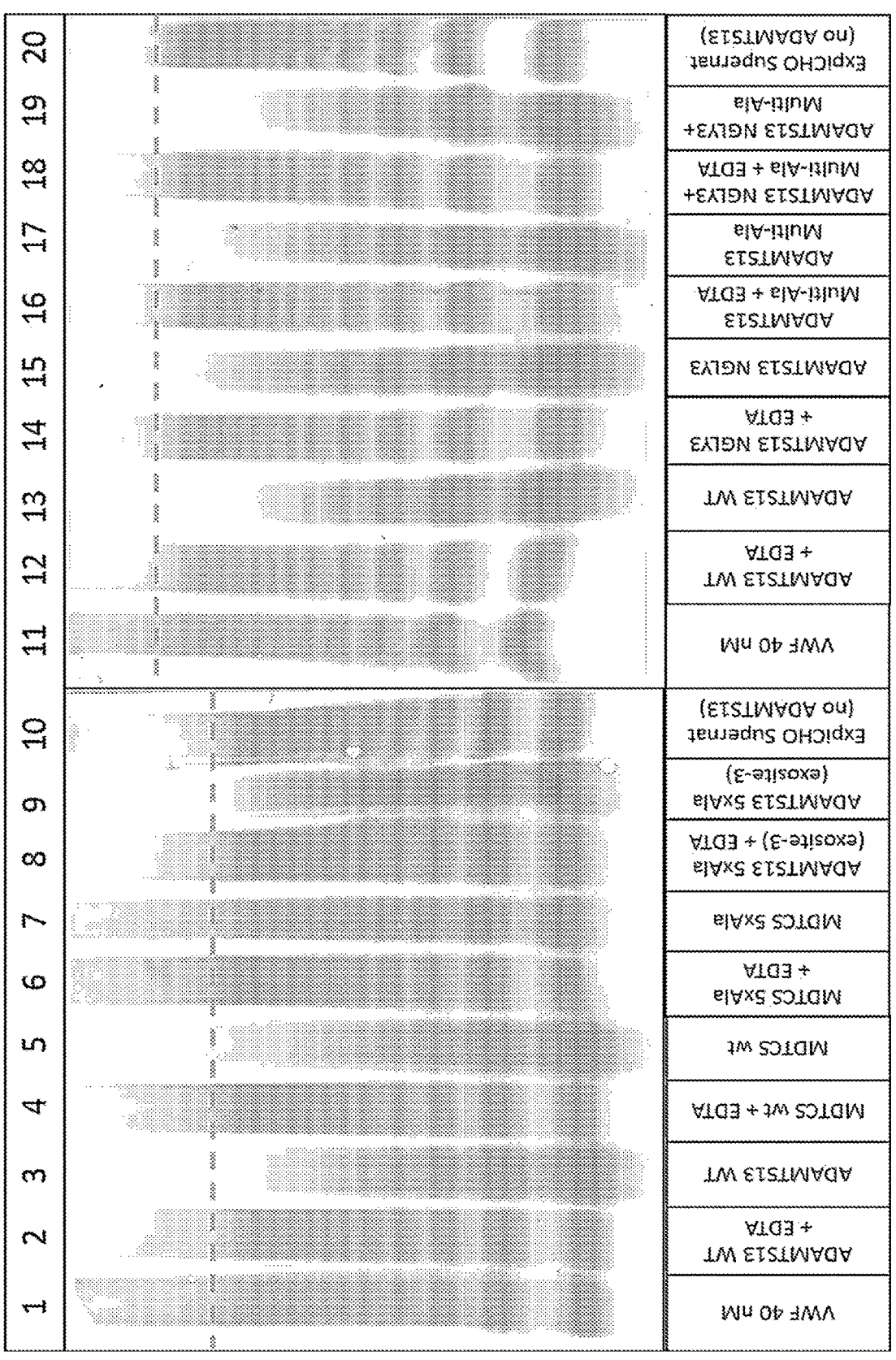
FIG. 9A: Proteolytic activity of ADAMTS13 variants towards VWF multimers under turbulent flow as measured in a so-called vortex assay (Zhang et al., 2007). Processing of VWF by wild type ADAMTS13 and ADAMTS13 variants is evaluated by degradation of high molecular weight multimers. Lane 1, 11: VWF only; Lane 2, 12: wild type ADAMTS13 plus EDTA, Lane 3, 13: wild type ADAMTS13; Lane 4: MDCTS domains ADAMTS13+EDTA, Lane 5: MDCTS wild type; Lane 6: MDCTS 5xAla+EDTA; Lane 7: MDTCS 5xAla; Lane 8: ADAMTS13 5xAla+EDTA; Lane 9: ADAMTS13 5xAla; Lane 10, 20: ExpiCHO Supernatant (no ADAMTS13); Lane 14: NGLY3+EDTA; Lane 15: NGLY3; Lane 16: ADAMTS13 Multi-Ala+EDTA; Lane 17: ADAMTS13 Multi-Ala; Lane 18: NGLY3+MultiAla+EDTA; Lane 19: NGLY3+Multi-Ala. MDCTS: truncated ADAMTS13 variant (residues 1-685). 5xAla corresponds to R568A/F592A/R660A/Y661A/Y665A. MultiAla corresponds to L591A/R636A/L637A/L668A.
Figure 9B:
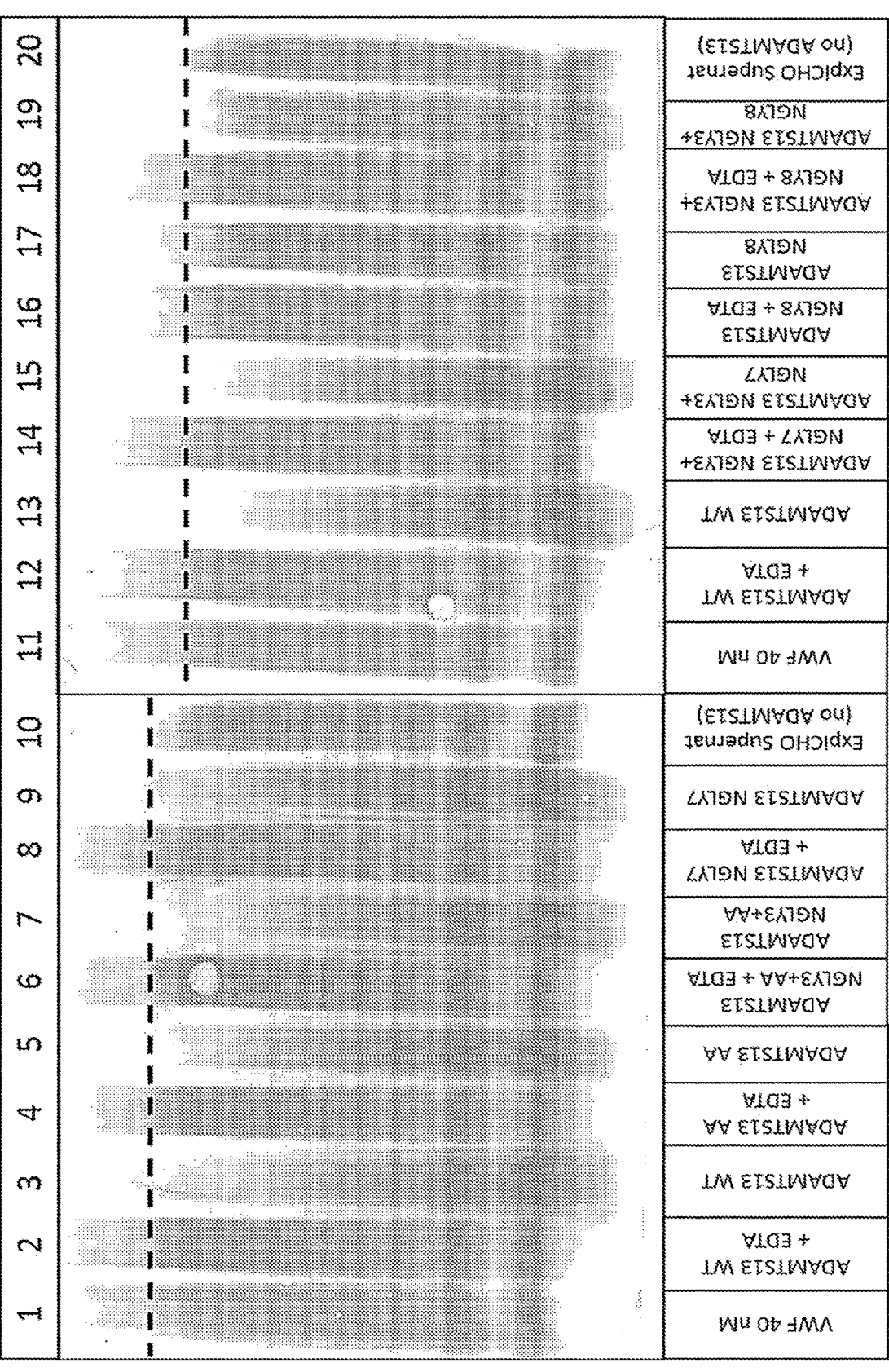
FIG. 9B: Proteolytic activity of ADAMTS13 variants towards VWF multimers under turbulent flow as measured in a so-called vortex assay (Zhang et al., 2007). Processing of VWF by wild type ADAMTS13 and ADAMTS13 variants is evaluated by degradation of high molecular weight multimers. Lane 1, 11: VWF only; Lane 2, 12: wild type ADAMTS13 plus EDTA, Lane 3, 13: wild type ADAMTS13; Lane 4: ADAMTS13+AA+EDTA, Lane 5: ADAMTS13+AA; Lane 6: NGLY3+AA+EDTA; Lane 7: NGLY3+AA; Lane 8: NGLY7+EDTA; Lane 9: NGLY7; Lane 10, 20: ExpiCHO Supernatant (no ADAMTS13); Lane 14: NGLY3+NGLY7+EDTA; Lane 15: NGLY3+NGLY7; Lane 16: NGLY8+EDTA; Lane 17: NGLY8; Lane 18: NGLY3+NGLY8+EDTA; Lane 19: NGLY3+NGLY8. AA corresponds to R568A/Y665A

We also assessed the ability of the new variants to process VWF multimers under shear stress employing a vortex assay. Under these conditions NGLY3 was fully active; also NGLY7 was clearly capable of processing the large VWF multimers (FIG. 9B). NGLY8 displayed a reduced ability to process VWF multimers when compared to NGLY3 and NGLY7 (FIG. 9B). Combinations of NGLY3/NGLY8 also revealed a reduced ability to process VWF multimers under these experimental conditions whereas combination of NGLY3/NGLY7 retained proteolytic activity towards multimeric VWF (FIG. 9B). Combinations of NGLY3 plus L591A/R636A/L637A/L668A and NGLY3 plus R568A/Y665A efficiently processed VWF multimers employing these conditions (FIG. 9A). In line with these observations also the proteolytic activity of R568A/Y665A and the L591A/R636A/L637A/L668A variants were reduced when compared to wild type ADAMTS13 (FIG. 9A).

We also assessed the ability of the new variants to process VWF multimers employing denaturing conditions. Under these conditions NGLY3 was fully active whereas NGLY7 and NGLY8 also displayed a reduced activity (Table 4). Combinations of NGLY3/NGLY7 and NGLY3/NGLY8 also revealed a reduced ability to process VWF multimers under these experimental conditions. Combinations of NGLY3 plus L591A/R636A/L637A/L668A and NGLY3 plus R568A/Y665A also were less efficient in processing VWF multimers employing these specific condition (Table 4).

TABLE 4

Antigen levels and activity of ADAMTS13 NGLY variants and controls

| Variant | Antigen level (µg/ml) | Activity level (% relative to wild type ADAMTS13) VWFFRETS73 | Ability to process VWF multimers under denaturing conditions |
|---|---|---|---|
| Full length ADAMTS13 wild type | 5.27 | 100 | ++++++ |
| NGLY3 | 4.60 | 125 | ++++++ |
| NGLY7 | 3.45 | 125 | +++++ |
| NGLY8 | 1.43 | 76 | ++ |
| NGLY3 plus NGLY7 | 4.26 | 135 | +++++ |
| NGLY3 plus NGLY8 | 2.49 | 120 | ++ |
| NGLY3 plus L591A/R636A/L637A/L668A | 4.42 | 95 | ++ |
| NGLY3 plus R568A/Y665A | 4.36 | 120 | ++ |
| NGLY3 plus R568A/Y665A plus L591A/R636A/L637A/L668A | 2.32 | 40 | Not tested |
| L591A/R636A/L637A/L668A | 4.77 | 90 | ++ |
| R568A/Y665A | 3.78 | 120 | ++ |

Next we assessed whether the newly designed ADAMTS13 variants were capable of neutralizing pathogenic autoantibodies that develop or originate from patients with immune TTP.

Figure 12:
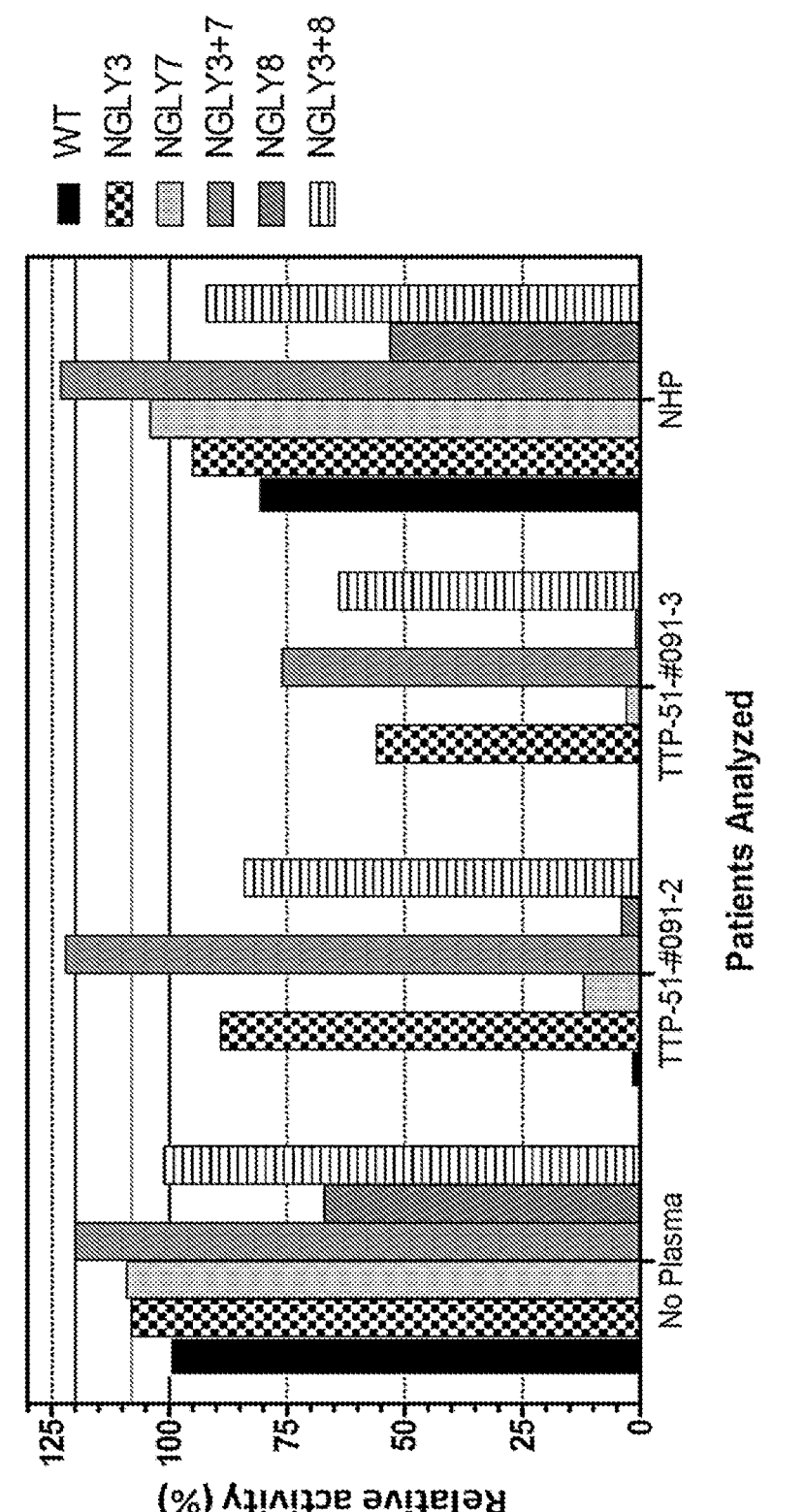
FIG. 12: Autoantibody resistance observed for NGLY3, NGLY7, NGLY3+NGLY6, NGLY8, NGLY3+8 in plasma derived of two high titer inhibitor patients. Two patient plasmas inhibiting wild type ADAMTS13 for at least 95% were selected for this Figure. Relative activity of NGLY3, NGLY7, NGLY3+NGLY7, NGLY8, NGLY3+8 variant to wild type ADAMTS13 (WT) as measured with FRETS-VWF73 as a substrate in the presence of 10 μl of patient sera or plasma is depicted. The activity obtained for wild type ADAMTS13 in the absence of patient sera or plasma was set at 100%.
Figure 13:
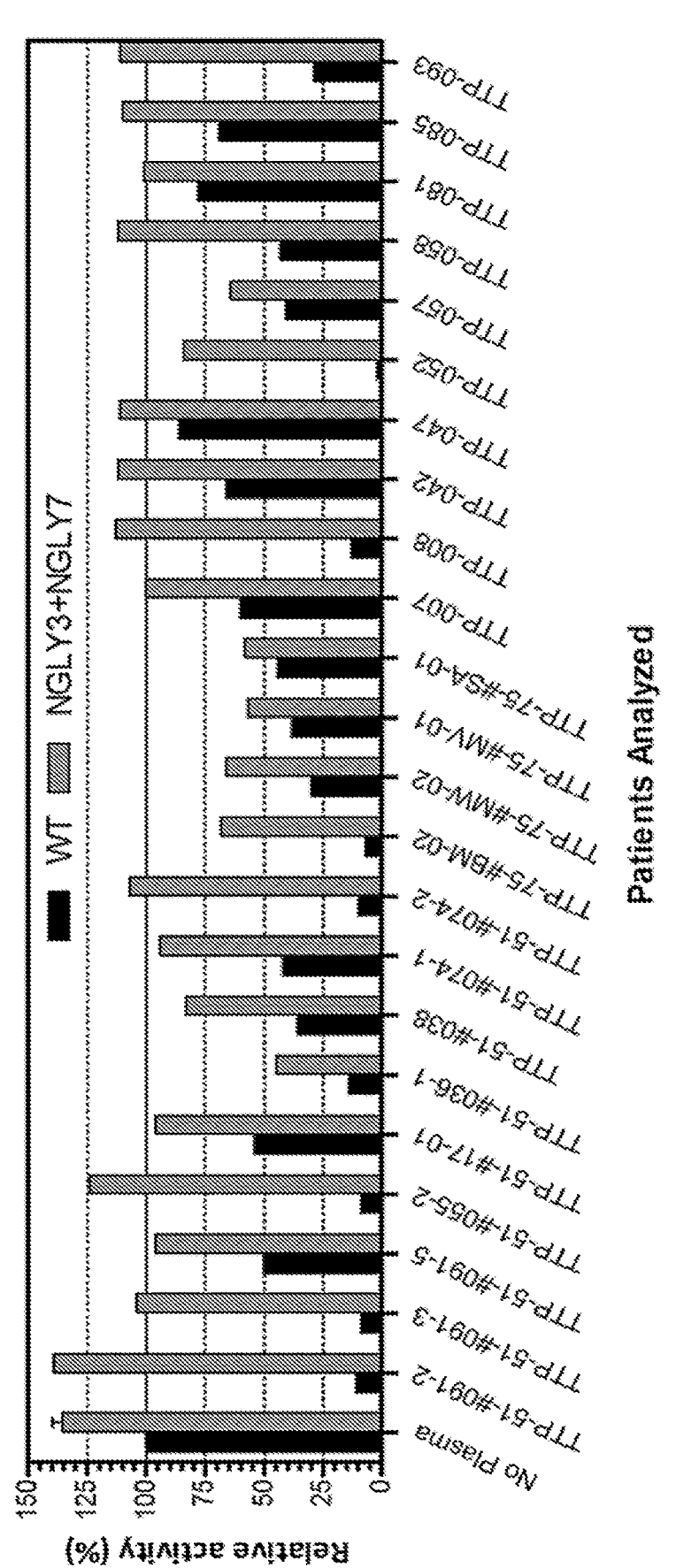
FIG. 13: Relative activity of NGLY3+NGLY7 variant to wild type ADAMTS13 (WT) as measured with FRETS-VWF73 as a substrate in the presence of 10 μl of patient sera or plasma. In total 23 patient samples were analyzed. The activity obtained for wild type ADAMTS13 in the absence of patient sera or plasma was set at 100%. Black bars show the reactivity of wild type ADAMTS13 in the presence of different patient plasma's and sera; grey bars show the activity of the NGLY3+NGLY7 variant in the presence of patient plasma's and sera.

We first assessed the antibody-resistance properties of NGLY7, NGLY8 as well as the combinations of NGLY3 plus NGLY7 and NGLY3 plus NGLY8 (FIG. 12) on two patient samples with high titer inhibitors. NGLY7 and NGLY8 were inhibited by patient autoantibodies in a similar manner as observed for wild type ADAMTS13 by the autoantibodies present in patient plasma. NGLY3 was only inhibited to a limited extent when compared to wild type ADAMTS13. The combination of NGLY3 and NGLY7 was more autoantibody-resistant when compared to NGLY3 alone. The combination of NGLY3 and NGLY8 was equally resistant when compared to NGLY3 by itself. We subsequently tested the combination of NGLY3 and NGLY7 on 23 patient samples (FIG. 13). The combination of NGLY3 and NGLY7 was shown to be autoantibody resistant in a large number of patient samples (FIG. 13).

Figure 14:
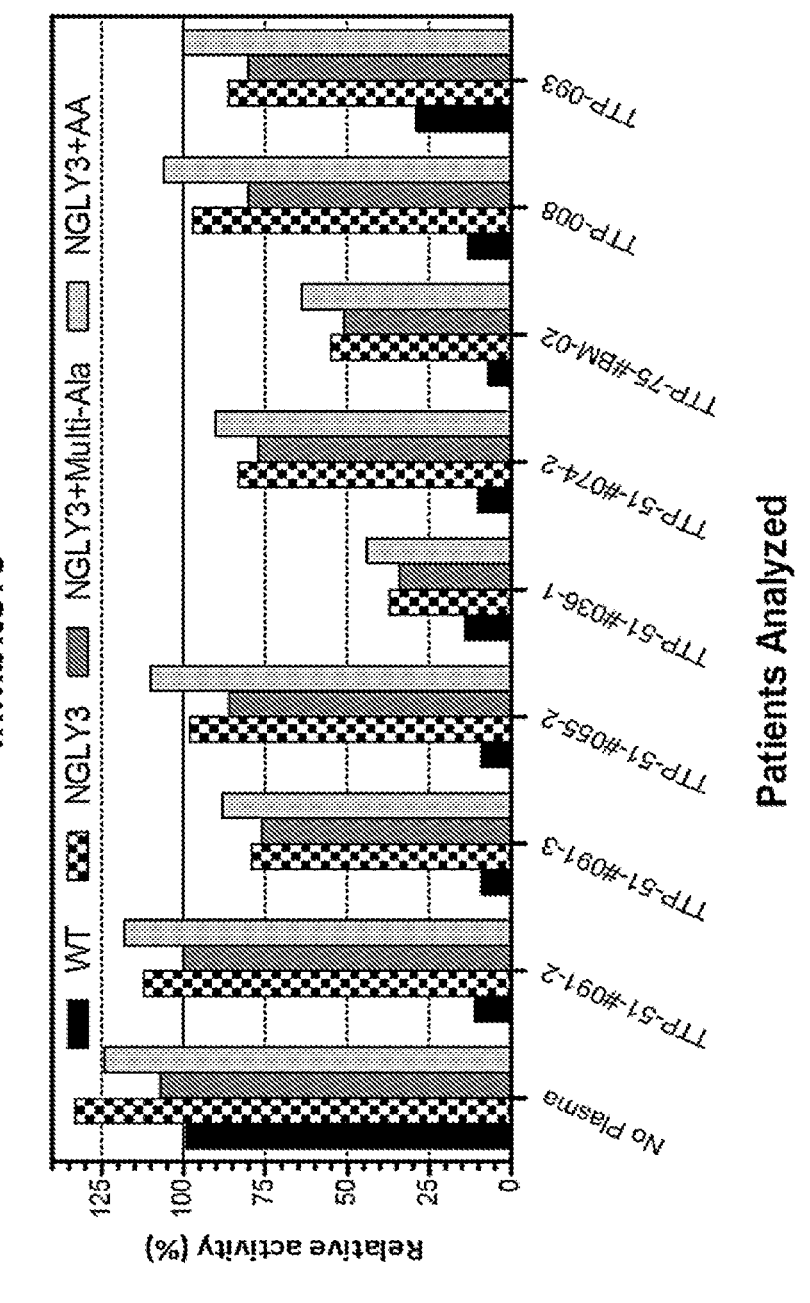
FIG. 14: Autoantibody resistance observed for NGLY3, NGLY3+Multi-Ala, NGLY3+AA in patient samples with potent inhibitors. Relative activity of NGLY3, NGLY3+Multi-Ala, NGLY3-AA variants to wild type ADAMTS13 (WT) as measured with FRETS-VWF73 as a substrate in the presence of 10 μl of patient sera or plasma is depicted. The activity obtained for wild type ADAMTS13 in the absence of patient sera or plasma was set at 100%. NGLY3+MultiAla corresponds to NGLY3 combined with L591A/R636A/L637A/L668A; NGLY3+AA corresponds to NGLY3 combined with R568A/Y665A.

We subsequently tested combinations of NGLY3 plus L591A/R636A/L637A/L668A and NGLY3 plus R568A/Y665A for their efficiency of autoantibody resistance in patient samples. In 8 out of 8 samples NGLY3 plus R568A/Y665A retained slightly more activity when compared to wild type ADAMTS13 (FIG. 14). Activity levels of NGLY3 plus R568A/Y665A were slightly higher when compared to NGLY3 alone suggesting an additional benefit of including additional Ala-substitutions in ADAMTS13. Combination of NGLY3 plus L591A/R636A/L637A/L668A were also evaluated for autoantibody resistance. In 8 out of 8 patients samples tested NGLY3 plus L591A/R636A/L637A/L668A retained significantly more activity when compared to wild type ADAMTS13 (FIG. 14). Activity levels in the presence of patient plasma or serum of NGLY3 plus L591A/R636A/L637A/L668A were similar to that of NGLY3. These findings show that substitution of these particular amino acids by an alanine had limited impact on autoantibody resistance.

Example 6. Further N-Glycan Variants of ADAMTS13

The previous examples focus on the spacer domain which contains a major binding site for pathogenic autoantibodies that develop in patients with immune TTP. It is well-known that autoantibodies can also target other domains on ADAMTS13 (Klaus et al., 2004; Thomas et al., 2015; Pos et al., 2011). Similar to the methods described in Example 1-4 N-glycan shielded ADAMTS13 variants can be designed that prevent the binding of autoantibodies targeting antibody binding sites present in the metallo-protease, disintegrin domain, TSP-1 repeat, the Cys-rich domain, epitopes outside R568, F592, R660, Y661 and R665 in the spacer domain, the TSP2-8 repeats and the CUB1/2 domains. 5. Additionally, NGLY3 and/or other N-glycan shielded ADAMTS13 variants can be combined with individual or multiple amino acid substitutions in the above-mentioned domains which results in a decline on auto-antibody binding while retaining at least partial proteolytic activity.

The 3D structure of ADAMTS13 was used to select the surface residues of ADAMTS13 to select potential N-glycosylation sites. ADAMTS13 crystal structure (PDB: 6qig) was used for following domains: Metalloprotease, Disintegrin-like domain, thrombospondin type 1 repeat 1 (TSP1-1), cysteine-rich and spacer domain. The rest of the structure was built by homology modeling from TSP1-2 to CUB2 domains as described previously (Ercig et al., 2018b). SwissPDB Viewer was used to investigate the 3D structure of ADAMTS13 to select the surface residues manually.

TABLE 5

Exposed regions on ADAMTS13 that allow for insertion or shifting of N-glycans to prevent the binding of pathogenic autoantibodies. Residues in bold are (part of) natural glycosylation sites of ADAMTS13. Bold and underlined residues have been shown to contain O-glycans. Residues indicated in bold and italics are modified by O-fucosylation of Ser (S) residues or C-mannosylation of Trp (W) residues.

| No. | Domain | Amino acid sequence | Numbering of residues (as shown in FIG. 1) |
|---|---|---|---|
| 1 | Metalloprotease (80-286) | DVFQAHQEDTER | 91-102 |
| 2 | Metalloprotease (80-286) | ELLRDPSLGAQFR | 113-125 |
| 3 | Metalloprotease (80-286) | KMVILTEPEGAPNITANLTSSLL | 130-152 |
| 4 | Metalloprotease (80-286) | QTINPEDDTDP | 159-169 |
| 5 | Metalloprotease (80-286) | RFDLELPDGNRQ | 180-191 |

TABLE 5-continued

Exposed regions on ADAMTS13 that allow for insertion or shifting of N-
glycans to prevent the binding of pathogenic autoantibodies.
Residues in bold are (part of) natural glycosylation sites of ADAMTS13.
Bold and underlined residues have been shown to contain O-glycans. Residues
indicated in bold and italics are modified by O-fucosylation of Ser (S)
residues or C-mannosylation of Trp (W) residues.

| No. | Domain | Amino acid sequence | Numbering of residues (as shown in FIG. 1) |
|---|---|---|---|
| 6 | Metalloprotease (80-286) | QLGGACSPTW | 197-206 |
| 7 | Metalloprotease (80-286) | EHDGAPGSGCGPS | 233-245 |
| 8 | Metalloprotease (80-286) | SDGAAPRAGL | 251-260 |
| 9 | Metalloprotease (80-286)/Disintegrin-like Domain (287-383) | PCSRRQLLSLLSAGRARCVWDPPRPQPGSAG HPPDAQ | 264-300 |
| 10 | Disintegrin-like Domain (287-383) | RVAFGPKAVACTFAREHLDMCQ | 312-333 |
| 11 | Disintegrin-like Domain (287-383) | TDPLDQSSCSRLL | 339-351 |
| 12 | Disintegrin-like Domain (287-383) | DGTECGVEK | 356-364 |
| 13 | Disintegrin-like Domain (287-383)/region between Disintegrin-like Domain and TSP type-1 1 (383-394)/TSP type-1 1 (394-439) | KGRCRSLVELTPIAAVHGRWSSWGPRSPCSRS | 368-399 |
| 14 | TSP type-1 1 (384-439) | RRRQ | 407-410 |
| 15 | TSP type-1 1 (384-439) | GGRACVGADLQAE | 419-431 |
| 16 | TSP type-1 1 (384-439)/Cysteine-rich (440-556) | NTQACEKTQLE | 434-444 |
| 17 | Cysteine-rich (440-556) | QQCARTDGQPLRSSPGGA | 448-465 |
| 18 | Cysteine-rich (440-556) | FYHWGAAVPHSQGDALCR | 467-484 |
| 19 | Cysteine-rich (440-556) | RAIGESFIMKRGDSFL | 488-502 |
| 20 | Cysteine-rich (440-556) | SGPRE | 511-515 |
| 21 | Cysteine-rich (440-556) | SGSCR | 524-528 |
| 22 | Cysteine-rich (440-556) | DGRMDSQQVWDR | 533-544 |
| 23 | Cysteine-rich (440-556)/Spacer (556-685) | VCGGDNSTCSPRKGSFTAGRARE | 547-569 |
| 24 | Spacer (556-685) | TFLTVTPN | 572-579 |
| 25 | Spacer (556-685) | YIANHRPLF | 584-592 |
| 26 | Spacer (556-685) | GGRYVVAGKMSISPN | 600-614 |
| 27 | Spacer (556-685) | YPSLLED | 617-623 |
| 28 | Spacer (556-685) | RVALTEDRLPR | 629-639 |
| 29 | Spacer (556-685) | RIWGPLQED | 644-652 |
| 30 | Spacer (556-685) | RRYGEEYGNLTR | 659-670 |
| 31 | Spacer (556-685) | TFTYFQPK | 674-681 |
| 32 | TSP type-1 2 (682-730) | PRQAWVWAAVRGPCS | 682-696 |

TABLE 5-continued

Exposed regions on ADAMTS13 that allow for insertion or shifting of N-
glycans to prevent the binding of pathogenic autoantibodies.
Residues in bold are (part of) natural glycosylation sites of ADAMTS13.
Bold and underlined residues have been shown to contain O-glycans. Residues
indicated in bold and italics are modified by O-fucosylation of Ser (S)
residues or C-mannosylation of Trp (W) residues.

| No. | Domain | Amino acid sequence | Numbering of residues (as shown in FIG. 1) |
|---|---|---|---|
| 33 | TSP type-1 2 (682-730)/ region between TSP type-1 2 and TSP type-1 3 (730-742) | AGLRWVNYSCLDQARKELVE | 701-720 |
| 34 | TSP type-1 2 (682-730)/ region between TSP type-1 2 and TSP type-1 3 (730-742) | QGSQQPPAWPEACVLEP | 725-741 |
| 35 | TSP type-1 3 (742-805) | PPYWAVGDFGPCSA*S*CG | 743-759 |
| 36 | TSP type-1 3 (742-805) | LRERPVRCVEAQGSLL | 762-777 |
| 37 | TSP type-1 3 (742-805)/ region between TSP type-1 3 and TSP type-1 4 (806-807) | PPARCRAGAQQPAVALETCNPQPCPAR | 781-807 |
| 38 | TSP type-1 4(808-859) | WEVSEPSSCTSAGGAGL | 808-824 |
| 39 | TSP type-1 4(808-859) | NETCVP | 828-833 |
| 40 | TSP type-1 4(808-859) | LEAPVTEGPGSVDEK | 838-852 |
| 41 | TSP type-1 4(808-859)/ region between TSP type-1 4 and TSP type-1 5 (859-896) | APEPCVGMSCPPG | 855-867 |
| 42 | region between TSP type-1 4 and TSP type-1 5 (859-896) | LDATSAGEKAP | 871-881 |
| 43 | region between TSP type-1 4 and TSP type-1 5 (859-896)/TSP type-1 5 (896-950) | SP*W*GSIRTGAQAAHVW | 882-897 |
| 44 | TSP type-1 5 (896-950) | V*S*CGR | 906-910 |
| 45 | TSP type-1 5 (896-950) | ELRFLCMDSALRVPVQEELCGL | 915-936 |
| 46 | TSP type-1 5 (896-950/ TSP type1 6(951-1011) | KPGSRRE CPARWQYKLAACSV*S*CGR | 939-968 |
| 47 | TSP type-1 6(951-1011) | RRILYCARAHGED | 972-984 |
| 48 | TSP type-1 6(951-1011) | EEILLDTQCQGLPRPEPQEACSLEP | 987-1011 |
| 49 | TSP type-1 7 (1012-1068) | CPPR*W* | 1012-1016 |
| 50 | TSP type-1 7 (1012-1068) | PCSA*S*CGLGTAR | 1023-1034 |
| 51 | TSP type-1 7 (1012-1068) | VQLDQGQDVEVDEAA | 1040-1054 |
| 52 | TSP type-1 7 (1012-1068)/region between TSP type-1 7 and TSP type-1 8 (1069-1071) | LVRPEASVPCLIAD | 1058-1071 |
| 53 | TSP type-1 8 (1071-1131) | RWHVGTWMECSV*S*CGD | 1075-1090 |
| 54 | TSP type-1 8 (1071-1131) | T | 1098 |
| 55 | TSP type-1 8 (1071-1131) | AQAPVPADFCQHLP | 1104-1117 |

TABLE 5-continued

Exposed regions on ADAMTS13 that allow for insertion or shifting of N-
glycans to prevent the binding of pathogenic autoantibodies.
Residues in bold are (part of) natural glycosylation sites of ADAMTS13.
Bold and underlined residues have been shown to contain O-glycans. Residues
indicated in bold and italics are modified by O-fucosylation of Ser (S)
residues or C-mannosylation of Trp (W) residues.

| No. | Domain | Amino acid sequence | Numbering of residues (as shown in FIG. 1) |
|---|---|---|---|
| 56 | TSP type-1 8 (1071-1131)/region between TSP type-1 8 and CUB1 domain (1132-1191) | RGCWAGPCVGQGTPSLVPHEEAAAPGR | 1123-1149 |
| 57 | region between TSP type-1 8 and CUB1 domain (1132-1191) | PAGASLEW | 1154-1161 |
| 58 | region between TSP type-1 8 and CUB1 domain (1132-1191) | RGLLFSPAPQPRRLLPGPQENS | 1165-1186 |
| 59 | CUB1 (1192-1298) | CGRQHLEPTGT | 1192-1202 |
| 60 | CUB1 (1192-1298) | DMRGPGQAD | 1204-1212 |
| 61 | CUB1 (1192-1298) | GRPLGE | 1218-1223 |
| 62 | CUB1 (1192-1298) | PGQAD | 1208-1212 |
| 63 | CUB1 (1192-1298) | PLG | 1220-1222 |
| 64 | CUB1 (1192-1298) | R | 1228 |
| 65 | CUB1 (1192-1298) | SSLNCSAGDMLLLWGRL | 12332-1248 |
| 66 | CUB1 (1192-1298) | NCSAGDMLL | 1235-1243 |
| 67 | CUB1 (1192-1298) | WGRLTWRKMCRKLLDM | 1245-1260 |
| 68 | CUB1 (1192-1298) | WRKMCRKLLDM | 1250-1260 |
| 69 | CUB1 (1192-1298) | TFSSKTNT | 1261-1268 |
| 70 | CUB1 (1192-1298) | KTNT | 1265-1268 |
| 71 | CUB1 (1192-1298) | RQRSGRPGGGV | 1272-1282 |
| 72 | CUB1 (1192-1298) | RCGRPG | 1274-1279 |
| 73 | CUB1 (1192-1298) | RYGSQLAPETFYRE | 1285-1298 |
| 74 | CUB1 (1192-1298) | QLAPETFYRE | 1289-1298 |
| 75 | CUB2 (1299-1427) | DMQLFGPWG | 1300-1308 |
| 76 | CUB2 (1299-1427) | DMQLFGPWGEIVSPSLSPATSNA | 1300-1322 |
| 77 | CUB2 (1299-1427) | SPSLSPATSNAGG | 1312-1324 |
| 78 | CUB2 (1299-1427) | RLFINVAPHARI | 1326-1337 |
| 79 | CUB2 (1299-1427) | APHAR | 1332-1336 |
| 80 | CUB2 (1299-1427) | LA | 1342-1343 |
| 81 | CUB2 (1299-1427) | TNMGAGTEGANASYIL | 1344-1359 |
| 82 | CUB2 (1299-1427) | AGTEGAN | 1348-1354 |
| 83 | CUB2 (1299-1427) | IRDTHSLRT | 1360-1368 |
| 84 | CUB2 (1299-1427) | RDTHSLRTTAF | 1361-1371 |
| 85 | CUB2 (1299-1427) | QQVLYWESESSQ | 1374-1385 |

TABLE 5-continued

Exposed regions on ADAMTS13 that allow for insertion or shifting of N-
glycans to prevent the binding of pathogenic autoantibodies.
Residues in bold are (part of) natural glycosylation sites of ADAMTS13.
Bold and underlined residues have been shown to contain O-glycans. Residues
indicated in bold and italics are modified by O-fucosylation of Ser (S)
residues or C-mannosylation of Trp (W) residues.

| No. | Domain | Amino acid sequence | Numbering of residues (as shown in FIG. 1) |
|-----|--------|---------------------|---------------------------------------------|
| 86 | CUB2 (1299-1427) | WESESSQAE | 1379-1387 |
| 87 | CUB2 (1299-1427) | EFSEGFLKAQAS | 1389-1400 |
| 88 | CUB2 (1299-1427) | SEGFLKAQASLRGQY | 1391-1405 |
| 89 | CUB2 (1299-1427) | LQSWVPEMQDPQSWKGKEGT | 1408-1427 |

Example 7. Mass Spectrometry Based Identification of N-Glycan Modified ADAMTS13

Figure 15:
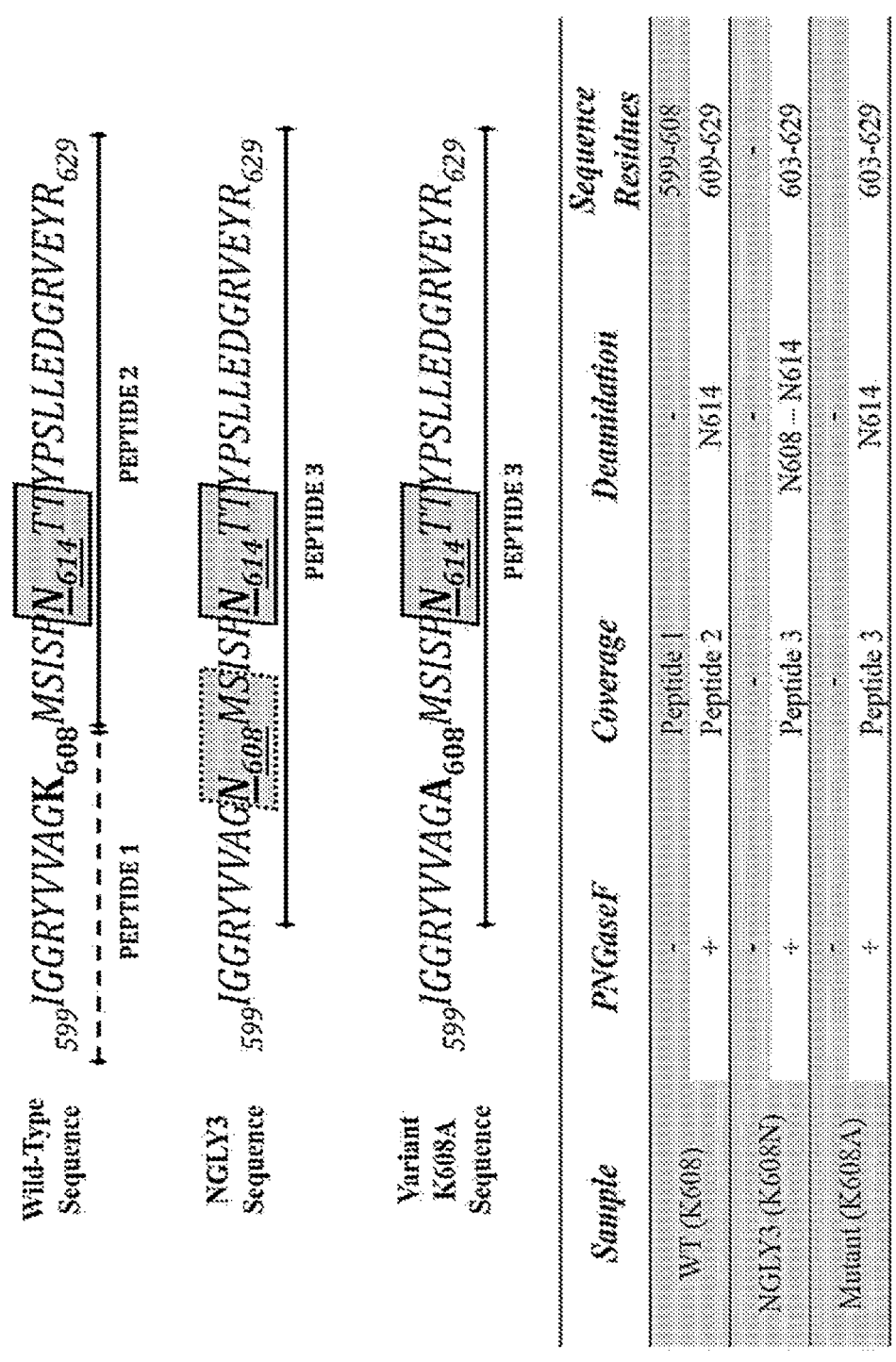
FIG. 15: Mass spectrometry based identification of N-glycan modified ADAMTS13. $_{599}$IGGRYVVAGK$_{608}$ MSISPN$_{614}$TTYPSLLEDGRVEYR$_{629}$: SEQ ID NO: 10; $_{599}$IGGRYVVAGN$_{608}$MSISPN$_{614}$TTYPSLLEDGRV-EYR$_{629}$: SEQ ID NO: 12; $_{599}$IGGRYVVAGA$_{608}$ MSISPN$_{614}$TTYPSLLEDGRVEYR$_{629}$: SEQ ID NO: 14.

In this example we employed mass spectrometry to provide proof of principle for the successful N-glycosylation of newly engineered consensus-sites within ADAMTS13. We selected the NGLY3 variant for this analysis. As outlined in a previous example K608 is replaced by N608 in NGLY3 thereby introducing a consensus site for the addition of N-glycan (see FIG. 15). We also included a variant in which K608 was replaced by an alanine (K608A). This does not introduce a consensus site for N-glycosylation (FIG. 15). Both NGLY3, K608A and wild-type ADAMTS13 were expressed in CHO cells as described in the previous examples. Each of these three ADAMTS13 variants were purified by immunoprecipitation using a mouse anti-V5 antibody coupled to magnetic Dynabeads. Prior to mass spectrometry analysis, these mutants were subjected to PNGaseF digestion (or not, as a control) followed by trypsin digestion on beads. PNGaseF treatment results in deamidation of asparagines in case an N-glycan is attached to this residue. For tryptic digestion of ADAMTS13 prior to mass spectrometry we employed trypsin which cleaves after lysines and arginines.

Figure 2:
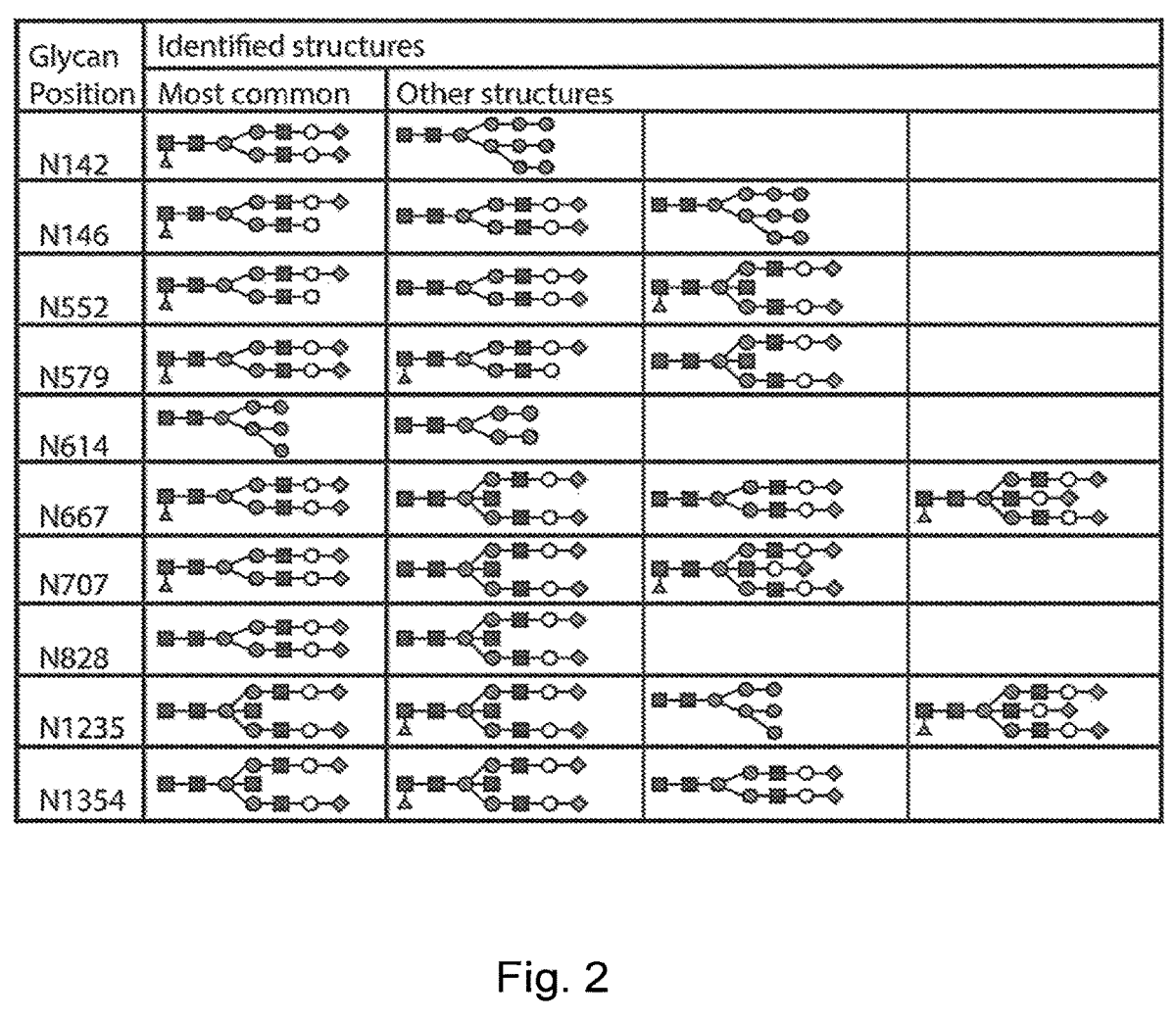

First we analyzed which peptide-sequences were retrieved following mass spectrometry analysis of wild type ADAMTS13. Overall coverage of trypsin-digested purified wild-type ADAMTS13 was 66%. Only peptides corresponding to amino acid sequence 599-629 are displayed in FIG. 15. Following trypsin digestion of wild-type ADAMTS13 a peptide corresponding to 1599-K608 (peptide 1) was identified. Peptides including M609 to R629 (peptide 2) were not identified since the presence of a heterogeneous glycan at N614 precludes mass-based identification of this peptide. Subsequently, we treated wild type ADAMTS13 with PNGaseF. PNGaseF treatment removes the N-glycan and additionally results in deamidation of asparagine resulting in a mass increase of 1 dalton. Analysis of PGNaseF treated ADAMTS13 allowed for the identification of peptide 1599-K608 as well as peptide M609-R629. Due to deamidation of N614 the mass of peptide M609-R629 was increased by 1 dalton. These observations show that peptide M609-R629 contains an N-glycan that is inserted at position N614 (indicated by box in FIG. 15). This is consistent with the previous identification of an N-glycan at N614 (see FIG. 2).

Next we analyzed NGLY3 in a similar manner. Following trypsin-digestion no peptides corresponding to region 1599- R629 were recovered. This observation indicates that one or more N-glycans may be present in this part of NGLY3. Upon treatment with PGNaseF one peptide Y603-R629 was identified (peptide 3: FIG. 15); N608 and N614 were found to be deamidated consistent with the presence of N-glycans at N608 and N614. Due to replacement of K608 by an N in the NGLY3 this variant cannot be cleaved anymore by trypsin at amino acid position 608 (indicated by boxes in FIG. 15). Taken together these results shows that an N-glycan has been successfully introduced at amino acid position 608 due to the replacement of K608 by N608.

As an additional control we analyzed an ADAMTS13 variant in which K608 was replaced by an alanine at this position. Identification of trypsin-cleaved peptides corresponding to this region were not observed in the absence of PGNaseF treatment consistent with the presence of a N-linked glycan in this area. Following digestion with PGNaseF a single Y603-R629 peptide was identified which contained a deamidated N at position 614 (indicated by box in FIG. 15). This analysis shows that A608 did not contain an N-linked glycan attached to A608; only the N-glycan normally present at N614 was identified for this variant.

Overall, the approach outlined in this proposal shows that introduction of a consensus-site for the addition of N-glycan at amino acid position 608 in NGLY3 results in attachment of an N-glycan at this position. Similarly, the presence of other N-linked glycans in NGLY1,2,4,5,6,7,8 and other glycan-modified ADAMTS13 variants including those listed in Example 7 can be successfully determined using the protocol outlined in this example.

REFERENCES

Austin S K, Starke R D, Lawrie A S, Cohen H, Machin S J, Mackie I J. The VWF/ADAMTS13 axis in the antiphospholipid syndrome: ADAMTS13 antibodies and ADAMTS13 dysfunction. Br J Haematol. 2008 May; 141 (4): 536-44. doi: 10.1111/j.1365-2141.2008.07074.x.

Bitsadze V, Bouvier S, Khizroeva J, Cochery-Nouvellon É, Mercier É, Perez-Martin A, Makatsariya A, Gris J C. Early ADAMTS13 testing associates with pre-eclampsia occurrence in antiphospholipid syndrome. Thromb Res. 2021 Apr. 27; 203:101-109. doi: 10.1016/j.thromres.2021.04.021.

Burbelo P D1, O'Hanlon T P. New autoantibody detection technologies yield novel insights into autoimmune disease. Curr Opin Rheumatol. 2014 November; 26 (6): 717-23.

Casina V C, Hu W, Mao J-H, et al. High-resolution epitope mapping by H X M S reveals the pathogenic mechanism and a possible therapy for autoimmune TTP syndrome. Proc. Natl. Acad. Sci. 2015; 112 (31): 9620-9625.

Chauhan A K, Motto D G, Lamb C B, Bergmeier W, Dockal M, Plaimauer B, Scheiflinger F, Ginsburg D, Wagner D D. Systemic antithrombotic effects of ADAMTS13. J Exp Med. 2006 Mar. 20; 203 (3): 767-76. doi: 10.1084/jem.20051732.

Chen X, Cheng X, Zhang S, Wu D. ADAMTS13: An Emerging Target in Stroke Therapy. Front Neurol. 2019 Jul. 17; 10:772. doi: 10.3389/fneur.2019.00772.

Crawley J T, de Groot R, Xiang Y, Luken B M, Lane D A. Unraveling the scissile bond: how ADAMTS13 recognizes and cleaves von Willebrand factor. Blood. 2011 Sep. 22; 118 (12): 3212-21.

De Groot R, Lane D A, Crawley J T B. The Role of the ADAMTS13 Cysteine-Rich Domain in VWF Binding and Proteolysis. Blood 2015; 125 (12): 1968-75.

Ercig B, Wichapong K, Reutelingsperger C P M, Vanhoorelbeke K, Voorberg J, Nicolaes G A F. Insights into 3D Structure of ADAMTS13: A Stepping Stone towards Novel Therapeutic Treatment of Thrombotic Thrombocytopeniaurpura. Thromb Haemost. 2018a January; 118 (1): 28-41.

Ercig B, Wichapong K, Reutelingsperger C P M, Vanhoorelbeke K, Voorberg J, Nicolaes G A F. Insights into 3D Structure of ADAMTS13: A Stepping Stone towards Novel Therapeutic Treatment of Thrombotic Thrombocytopeniaurpura. Thromb Haemost. 2018 January; 118 (1): 28-41.

Graça A G N, Ercig B, Velasquez Pereira L C, et al. Modifying ADAMTS13 to modulate binding of pathogenic autoantibodies of patients with acquired thrombotic thrombocytopeniaurpura. 2019; Haematologica. 2019 Nov. 21. pii: haematol.2019.226068. doi: 10.3324/haematol.2019.226068. [Epub ahead of print].

Hie M1, Gay J, Galicier L, Provot F, Presne C, Poullin P, Bonmarchand G, Wynckel A, Benhamou Y, Vanhille P, Servais A, Bordessoule D, Coindre J P, Hamidou M, Vernant J P, Veyradier A, Coppo P. Preemptive rituximab infusions after remission efficiently prevent relapses in acquired thrombotic thrombocytopeniarpura. Blood. 2014 Jul. 10; 124 (2): 204-10.

Jian C, Xiao J, Gong L, et al. Gain-of-function ADAMTS13 variants that are resistant to autoantibodies against ADAMTS13 in patients with acquired thrombotic thrombocytopeniaurpura. Blood. 2012; 119 (16): 3836-3843.

Kelwick R, Desanlis I, Wheeler G N, Edwards D R. The ADAMTS (A Disintegrin and Metalloproteinase with Thrombospondin motifs) family. Genome Biol. 2015 May 30; 16:113.

Klaus C, Plaimauer B, Studt J D, Dorner F, Lammle B, Mannucci P M, Scheiflinger F. Epitope mapping of ADAMTS13 autoantibodies in acquired thrombotic thrombocytopeniaurpura. Blood. 2004 Jun. 15; 103 (12): 4514-9.

Kokame K, Nobe Y, Kokubo Y, Okayama A, Miyata T. FRETS-VWF73, a first fluorogenic substrate for ADAMTS13 assay. Br J Haematol. 2005 April; 129 (1): 93-100.

Leem J, Dunbar J, Georges G, Shi J, Deane C M. ABody-Builder: Automated antibody structure prediction with data-driven accuracy estimation. MAbs. 2016; 8 (7): 1259-1268.

Levi M, Scully M, Singer M. The role of ADAMTS-13 in the coagulopathy of sepsis. J Thromb Haemost. 2018 April; 16 (4): 646-651. doi: 10.1111/jth. 13953.

De Maeyer B, De Meyer S F, Feys H B, Pareyn I, Vandeputte N, Deckmyn H, Vanhoorelbeke K. The distal carboxyterminal domains of murine ADAMTS13 influence proteolysis of platelet-decorated VWF strings in vivo. J Thromb Haemost. 2010 October; 8 (10): 2305-12.

Mazepa M A, Masias C, Chaturvedi S. How targeted therapy disrupts the treatment paradigm for acquired TTP: the risks, benefits, and unknowns. Blood. 2019 Aug. 1; 134 (5): 415-420.

Miller B R, McGee T D, Swails J M, et al. MMPBSA.py: An efficient program for end-state free energy calculations. J. Chem. Theory Comput. 2012; 8 (9): 3314-3321.

Pos W, Luken B M, Kremer Hovinga J A, et al. VH1-69 germline encoded antibodies directed towards ADAMTS13 in patients with acquired thrombotic thrombocytopeniaurpura. J. Thromb. Haemost. 2009; 7 (3): 421-428.

Pos W, Crawley J T B, Fijnheer R, et al. An autoantibody epitope comprising residues R660, Y661, and Y665 in the ADAMTS13 spacer domain identifies a binding site for the A2 domain of VWF. Blood. 2010; 115 (8): 1640-1649.

Pos W, Sorvillo N, Fijnheer R, et al. Residues Arg568 and Phe592 contribute to an antigenic surface for anti-Adamts13 antibodies in the spacer domain. Haematologica. 2011; 96 (11): 1670-1677.

Ramsi M, Al Ali A S. Thrombocytopenia-associated multiple-organ failure (TAMOF): recognition and management. BMJ Case Rep. 2018 Aug. 27; 2018: bcr2018225594. doi: 10.1136/bcr-2018-225594.

Scully M, Knobl P, Kentouche K, Rice L, Windyga J, Schneppenheim R, Kremer Hovinga J A, Kajiwara M, Fujimura Y, Maggiore C, Doralt J, Hibbard C, Martell L, Ewenstein B. Recombinant ADAMTS-13: first-in-human pharmacokinetics and safety in congenital thrombotic thrombocytopeniaurpura. Blood. 2017 Nov. 9; 130 (19): 2055-2063.

Scully M, Cataland S R, Peyvandi F, Coppo P, Knobl P, Kremer Hovinga J A, Metjian A, de la Rubia J, Pavenski K, Callewaert F, Biswas D, De Winter H, Zeldin R K; HERCULES Investigators. Caplacizumab Treatment for Acquired Thrombotic Thrombocytopeniaurpura. N Engl J Med. 2019 Jan. 24; 380 (4): 335-346.

Sins J W R, Schimmel M, Luken B M, Nur E, Zeerleder S S, van Tuijn C F J, Brandjes D P M, Kopatz W F, Urbanus R T, Meijers J C M, Biemond B J, Fijnvandraat K. Dynamics of von Willebrand factor reactivity in sickle cell disease during vaso-occlusive crisis and steady state. J Thromb Haemost. 2017 July; 15 (7): 1392-1402. doi: 10.1111/jth.13728.

Tao Z, Wang Y, Choi H, Bernardo A, Nishio K, Sadler J E, López J A, Dong J F. Cleavage of ultralarge multimers of von Willebrand factor by C-terminal-truncated mutants of ADAMTS-13 under flow. Blood 2005; 106 (01): 141-143.

Thomas M R, de Groot R, Scully M A, Crawley J T. Pathogenicity of Anti-ADAMTS13 Autoantibodies in Acquired Thrombotic Thrombocytopeni Purpura. EBioMedicine. 2015 Jun. 11; 2 (8): 942-52.

Turecek P L, Peck R C, Rangarajan S, Reilly-Stitt C, Laffan M A, Kazmi R, James I, Dushianthan A, Schrenk G, Gritsch H, Ewenstein B M, Mellgard B, Erdlenbruch W, Jain N, Binder N B, Mumford A D. Recombinant ADAMTS13 reduces abnormally up-regulated von Willebrand factor in plasma from patients with severe COVID-19. Thromb Res. 2021 May; 201:100-112. doi: 10.1016/j.thromres.2021.02.012.

Xiao J, Jin S Y, Xue J, Sorvillo N, Voorberg J, Zheng X L. Essential domains of a disintegrin and metalloprotease with thrombospondin type 1 repeats-13 metalloprotease required for modulation of arterial thrombosis. Arteriosller Thromb Vasc Biol. 2011 October; 31 (10): 2261-9.

The invention claimed is:

1. An ADAMTS13 protein variant having ADAMTS13 activity comprising amino acid residues corresponding to amino acid residues 1 to 685 of the amino acid sequence of SEQ ID NO: 1 and wherein one or more N-linked glycosylation sites are added as compared to a wild-type ADAMTS13 and/or one or more existing N-linked glycosylation sites are shifted as compared to a wild-type ADAMTS13 in a spacer domain comprising amino acid residues corresponding to amino acid residues S556 to A685 of the amino acid sequence of SEQ ID NO: 1.

2. The ADAMTS13 protein variant of claim 1 comprising amino acid residues corresponding to amino acid residues 1 to 1427 of the amino acid sequence of SEQ ID NO: 1.

3. The ADAMTS13 protein variant of claim 1, wherein one or more existing N-linked glycosylation sites are shifted in part of the spacer domain comprising amino acid residues corresponding to amino acid residues R568 to R670 of the amino acid sequence of SEQ ID NO: 1.

4. The ADAMTS13 protein variant of claim 1, comprising an N-linked glycosylation site at an amino acid residue corresponding to amino acid residues selected from the group consisting of 568, 591, 608, 609, 636, 637, 665, 668, and combinations thereof of the amino acid sequence of SEQ ID NO: 1.

5. The ADAMTS13 protein variant of claim 1, comprising an N-linked glycosylation site at amino acid residue corresponding to amino acid residue 608 of the amino acid sequence of SEQ ID NO: 1.

6. The ADAMTS13 protein variant of claim 1, having proteolytic activity against Von Willebrand Factor (VWF) that is at least 10% of the proteolytic activity against VWF of wild-type ADAMTS13.

7. The ADAMTS13 protein variant of claim 1 comprising an N-linked glycosylation site comprising an amino acid residue corresponding to amino acid residues selected from the group consisting of R568, L591, V604, V605, A606, G607, K608, M609, R636, L637, P638, R639, Y665, L668 and combinations thereof of the amino acid sequence of SEQ ID NO: 1.

8. The ADAMTS13 protein variant of claim 1, comprising a mutation selected from the group consisting of 568REY570 to 560NET570 (NGLY1), 591LFT593 to 591NFT593 (NGLY2), 608KMSI611 to 608NMSI611 (NGLY3), 608KMSI611 to 608KNST611 (NGLY4), 636RLPR639 to 636NLSR639 (NGLY5), 636RLPL639 to 636RNAS639 (NGLY6), 665YGNL668 to 665NVTL668 (NGLY7), 667NLTRP671 to 667LNVTA671 (NGLY8), and combinations thereof of the amino acid sequence of SEQ ID NO: 1.

9. The ADAMTS13 protein variant of claim 8, comprising the mutation 608KMSI611 to 608NMSI611 (NGLY3).

10. The ADAMTS13 protein variant of claim 1, further comprising a mutation at one or more amino acid residues.

11. The ADAMTS13 protein variant of claim 10, wherein said mutation at one or more amino acid residues is in the spacer domain comprising amino acid residues corresponding to amino acid residues S556 to A684 of the amino acid sequence of SEQ ID NO: 1.

12. The ADAMTS13 protein variant of claim 1, further comprising a mutation at an amino acid residue corresponding to amino acid residues selected from the group consisting of R568, L591, F592, R636, L637, L668, L591, F592, R636, L637, R660, Y661, Y665, L668 and combinations thereof of the amino acid sequence of SEQ ID NO: 1.

13. The ADAMTS13 protein variant of claim 1, comprising mutations R568A and Y665A or mutations L591A, R636A, L637A, and L668A.

14. The ADAMTS13 protein variant of claim 1, comprising an N-glycan at said one or more N-linked glycosylation sites that are added and/or wherein said one or more existing N-linked glycosylation sites that are shifted comprise an N-linked glycan.

15. A pharmaceutical composition comprising the ADMATS13 protein variant of claim 1 and one or more pharmaceutically acceptable carriers, adjuvants, excipients and/or diluents.

16. A method for treatment of a disorder characterized by aberrant Von Willebrand Factor (VWF) activity and/or VWF processing comprising administering to a subject in need thereof a therapeutically effective amount of the ADAMTS13 protein variant of claim 1.

17. The method of claim 16, wherein said disorder is a thrombotic disease.

18. The method of claim 17, wherein said thrombotic disease is a thrombotic microangiopathy or a disorder selected from the group consisting of thrombotic thrombocytopenia purpura (TTP), including immune-mediated TTP (iTTP), hemolytic-uremic syndrome (HUS), ischemic stroke, systemic thrombosis, COVID19, antiphospholipid syndrome, preeclampsia/HELLP syndrome, sepsis, and sickle cell disease.

19. The ADAMTS13 protein variant of claim 7 comprising a mutation selected from the group consisting of R568N, L591N, V604N, V605N, A606N, G607N, K608N, M609N, R636N, L637N, P638N, R639N, Y665N, L668N and combinations thereof.

20. The ADAMTS13 protein variant of claim 12, further comprising a mutation selected from the group consisting of R568K, R568A, R568N, L591A, F592Y, F592A, F592N, R636A, L637A, R660K, R660A, R660N, Y661F, Y661A, Y661N, Y665F, Y665A, Y665N, L668A, and combinations thereof.

\*    \*    \*    \*    \*